(12) United States Patent
Vecten et al.

(10) Patent No.: US 11,590,271 B2
(45) Date of Patent: Feb. 28, 2023

(54) EASILY MOVABLE BLOOD PURIFICATION SYSTEMS

(71) Applicant: NextKidney SA, Lausanne (CH)

(72) Inventors: Didier Vecten, Lausanne (CH); Ricardo Allendes, Lausanne (CH); Paul Vescovo, Lausanne (CH)

(73) Assignee: NextKidney SA, Lausanne (CH)

(*) Notice: Subject to any disclaimer, the term of this patent is extended or adjusted under 35 U.S.C. 154(b) by 16 days.

(21) Appl. No.: 16/766,757

(22) PCT Filed: Oct. 31, 2018

(86) PCT No.: PCT/IB2018/058539
§ 371 (c)(1),
(2) Date: May 26, 2020

(87) PCT Pub. No.: WO2019/087096
PCT Pub. Date: May 9, 2019

(65) Prior Publication Data
US 2021/0338909 A1    Nov. 4, 2021

(30) Foreign Application Priority Data

Oct. 31, 2017 (EP) .................................... 17199362
Oct. 31, 2017 (EP) .................................... 17199363
(Continued)

(51) Int. Cl.
*A61M 1/16*    (2006.01)
*A61M 1/36*    (2006.01)
(Continued)

(52) U.S. Cl.
CPC ........ *A61M 1/3644* (2014.02); *A61M 1/1603* (2014.02); *A61M 1/1621* (2014.02);
(Continued)

(58) Field of Classification Search
CPC .. A61M 1/1603; A61M 1/1621; A61M 1/267; A61M 1/3424; A61M 1/3627;
(Continued)

(56) References Cited

U.S. PATENT DOCUMENTS 8,029,454 B2    10/2011    Kelly et al.
8,114,276 B2    2/2012    Childers et al.
(Continued)

FOREIGN PATENT DOCUMENTS

EP    2609944 A1    7/2013
EP    2896417 A1    7/2015
(Continued)

OTHER PUBLICATIONS

EPO Search Report dated May 11, 2018 for Application EP17209117.5.
(Continued)

*Primary Examiner* — Dirk R Bass
(74) *Attorney, Agent, or Firm* — Nixon & Vanderhye P.C.

(57) ABSTRACT

A dialysis system may include a blood circuit, a cassette, a subsystem having a processor, a sensor, and a blood pumping mechanism, a housing in which the subsystem is arranged, a movable support arranged in the housing and configured to hold the sensor and/or the blood pumping mechanism of the subsystem, a cassette holder configured to removably receive the cassette, and a loading system. The loading system may be configured to move the movable support, e.g. by an axial movement, to a first position and to a second position relatively to the housing while the cassette holder is fixedly arranged in the housing. The loading system may have an electric motor controlled by the processor, a drive assembly coupled to the electric motor, and a guiding assembly configured to cooperate with the drive assembly.

18 Claims, 35 Drawing Sheets

(30) Foreign Application Priority Data

Dec. 20, 2017 (EP) .................................... 17209117
Dec. 20, 2017 (EP) .................................... 17209126

(51) Int. Cl.
*A61M 1/26* (2006.01)
*A61M 39/10* (2006.01)
*A61M 39/22* (2006.01)

(52) U.S. Cl.
CPC .......... *A61M 1/267* (2014.02); *A61M 1/3627* (2013.01); *A61M 39/10* (2013.01); *A61M 39/22* (2013.01); *A61M 1/3646* (2014.02); *A61M 2205/3337* (2013.01); *A61M 2205/50* (2013.01)

(58) Field of Classification Search
CPC .. A61M 1/3644; A61M 1/3646; A61M 1/365; A61M 2205/3337; A61M 2205/50; A61M 39/10; A61M 39/22
See application file for complete search history.

(56) References Cited

U.S. PATENT DOCUMENTS

| | | | |
|---|---|---|---|
| 8,444,587 | B2 | 5/2013 | Kelly et al. |
| 8,512,553 | B2 | 8/2013 | Cicchello et al. |
| 8,523,799 | B2 | 9/2013 | Biesel et al. |
| 8,585,634 | B2 | 11/2013 | Neftel et al. |
| 9,526,820 | B2 | 12/2016 | Beiriger et al. |
| 9,931,456 | B2 | 4/2018 | Rovatti et al. |
| 2003/0209884 | A1 | 11/2003 | Joie et al. |
| 2009/0012461 | A1 | 1/2009 | Childers et al. |
| 2012/0267291 | A1 | 10/2012 | Coates |
| 2014/0088493 | A1 | 3/2014 | Pan |
| 2014/0216250 | A1 | 8/2014 | Meyer et al. |
| 2015/0122721 | A1 | 5/2015 | Childers et al. |
| 2015/0367062 | A1* | 12/2015 | Brugger ................ A61M 1/365 210/646 |
| 2016/0106906 | A1 | 4/2016 | Buckberry |
| 2020/0179224 | A1 | 6/2020 | Wolf et al. |

FOREIGN PATENT DOCUMENTS

| | | |
|---|---|---|
| EP | 3011984 A1 | 4/2016 |
| EP | 3703775 B1 | 2/2022 |
| EP | 3703776 B1 | 2/2022 |
| GB | 2110564 A | 6/1983 |
| RU | 93276 U1 | 4/2010 |
| WO | WO 2005009511 A2 | 2/2005 |
| WO | WO 2009055639 | 4/2009 |
| WO | WO 2011017215 | 2/2011 |
| WO | WO 2014155137 | 10/2014 |
| WO | WO 2018210926 | 11/2018 |

OTHER PUBLICATIONS

EPO Written Opinion dated May 11, 2018 for Application EP17209117.5.
International Search Report dated Feb. 11, 2019 for Application PCT/IB2018/058539.
International Search Report dated Feb. 18, 2019 for Application PCT/IB2018/058547.
Written Opinion of the ISA dated Feb. 18, 2019 for Application PCT/IB2018/058547.
Written Opinion of the ISA dated Feb. 11, 2019 for Application PCT/IB2018/058539.
Russian Office Action dated Feb. 3, 2022 for Application No. RU 2020-117675.
Russian Search Report dated Feb. 3, 2022 for Application No. RU 2020-117675.
European Opinion dated May 4, 2022 for Application No. EP22151016.7.
European Search Report dated May 4, 2022 for Application No. EP22151016.7.
Decision to Grant a European patent pursuant to Article 97(1)EPC for EP Application No. 18811065.4 / Patent No. 3703775.
Decision to Grant a European patent pursuant to Article 97(1)EPC for EP Application No. 18811066.2 / Patent No. 3703776.
European Grant Certificate for EP Application No. 18811065.4 / Patent No. 3703775.
European Grant Certificate for EP Application No. 18811066.2 / Patent No. 3703776.

* cited by examiner

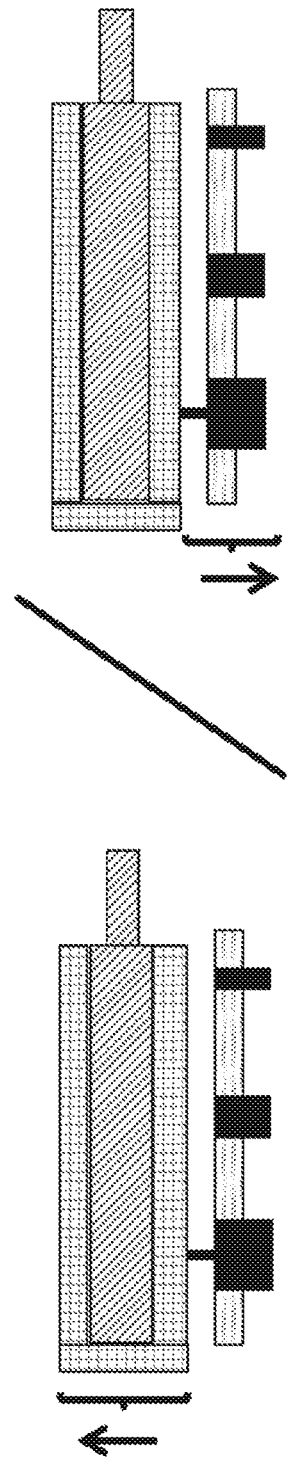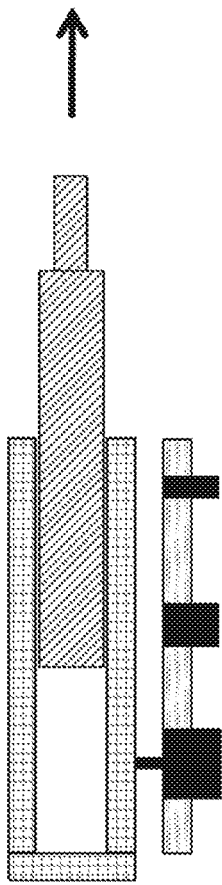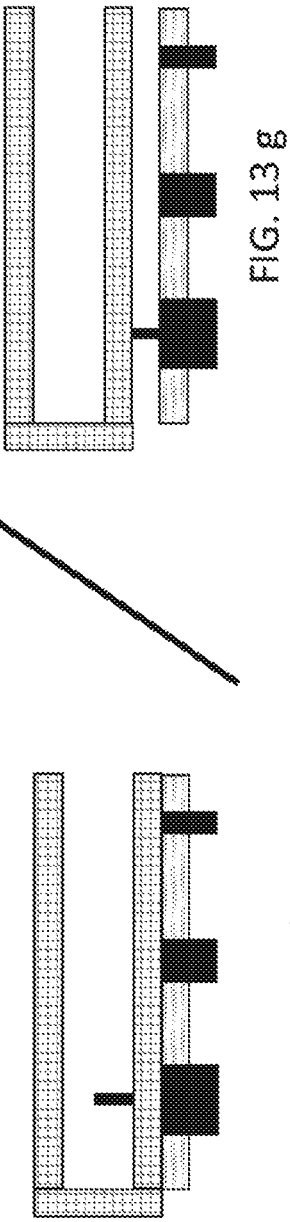

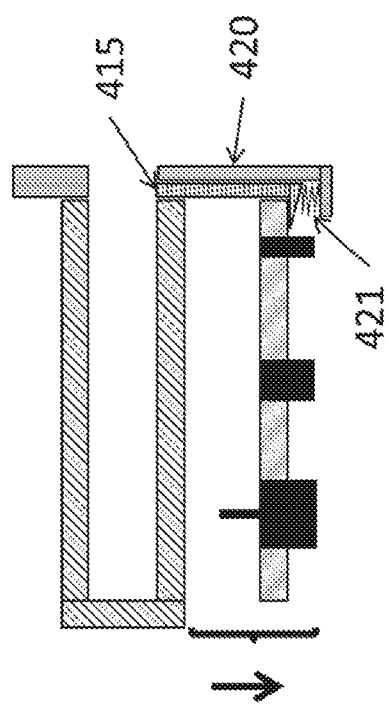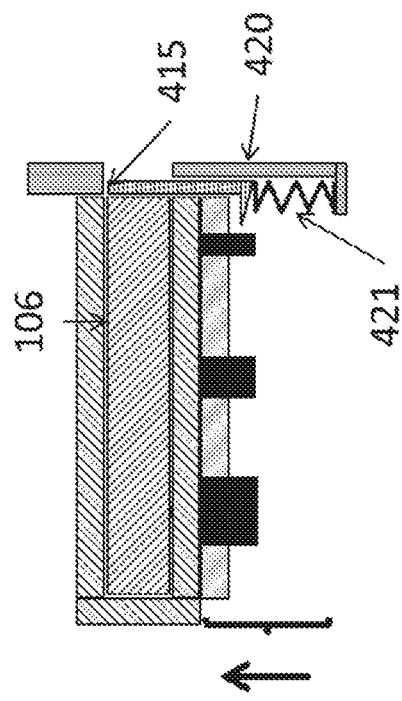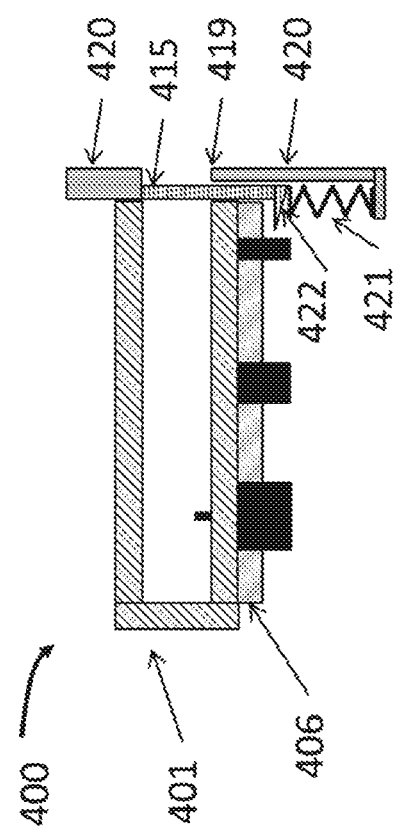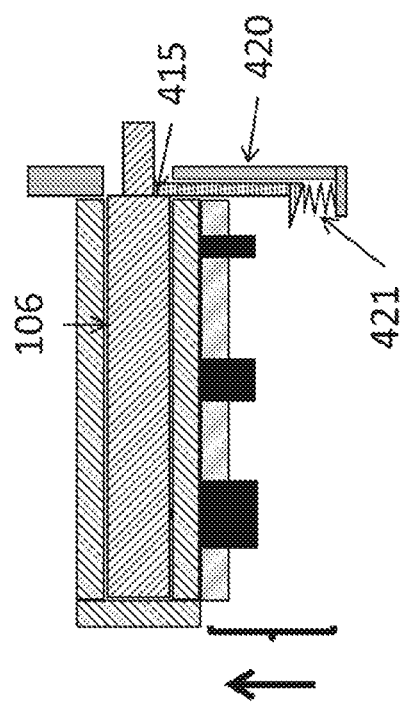

EASILY MOVABLE BLOOD PURIFICATION SYSTEMS

CROSS REFERENCE TO RELATED APPLICATIONS

The present application is a United States national stage application of International patent application PCT/IB2018/058539 filed on Oct. 31, 2018 that designated the United States, and claims foreign priority to four (4) European patent applications EP 17199362.9 filed on Oct. 31, 2017, EP 17199363.7 filed on Oct. 31, 2017, EP 17209117.5 filed on Dec. 20, 2017, and EP 17209126.6 filed in Dec. 20, 2017, the contents of all five (5) documents being herewith incorporated by reference in their entirety.

FIELD OF INVENTION

The present invention relates generally to the field of blood purification systems and methods. For example, the present invention relates to an extracorporeal blood treatment apparatus conducting a dialysis treatment for example hemodialysis treatment.

STATE OF THE ART

Extracorporeal blood treatment is typically used to extract undesirable matter or molecules from the patient's blood and/or add desirable matter or molecules to the blood. Such treatment is used with patients unable to effectively remove matter from their blood, such as when a patient has suffered temporary or permanent kidney failure.

This treatment is typically accomplished by removing the blood from the patient, introducing the blood into a filtration unit (for example a dialyzer) where the blood is allowed to flow past a semipermeable membrane. The semipermeable membrane selectively allows matter in the blood to cross the membrane from a primary chamber into a secondary chamber and also selectively allows matter in the secondary chamber to cross the membrane into the blood in the primary chamber, depending on the type of treatment. A number of different types of extracorporeal blood treatments may be performed:

An ultrafiltration (UF) treatment;
A hemofiltration (HF) treatment;
A hemodialysis (HD) treatment;
A hemodiafiltration (HDF) treatment.

Currently, the most widely used method of kidney dialysis for treatment of end stage renal disease is hemodialysis. In hemodialysis, the patient's blood is cleansed by passing it through the primary chamber and a dialysate solution through the secondary chamber. During dialysis, arterial and venous parts of blood line convey a patients blood to and from the filtration means (for example a dialyzer). Impurities and toxins are removed from the patient's blood by diffusion or convection across a membrane in the filtration means. Hemodialysis is commonly required three times a week with each dialysis requiring up to four to five hours in a dialysis center or at home where treatment may be more frequent (up to daily) and shorter (down to two hours). During the treatment, the patient is connected to a hemodialysis machine and the patient's blood is pumped through the machine. Catheters are inserted into the patient's veins and arteries so that blood can flow to and from the hemodialysis machine. A large amount of a dialysis solution, for example about 120 liters, is consumed to dialyze the blood during a single hemodialysis therapy.

Currently, the trend is for more homecare. The homecare provides a better life and greater privacy to the patient and is less expensive. Nevertheless, the extracorporeal blood treatment apparatus are heavy, large and complex to use.

For example, the size of an extracorporeal blood treatment system may be 1370×480×480 mm and its weight may be 86 kg. Even if some companies try to design smaller system, the smallest apparatus are for example: N×Stage System One: 385×385×385 mm for 34 kg, and Quanta SC+480×370×450 for 30 kg. Thus these apparatus cannot be easily moved and it will be impossible or at least very difficult to travel with such systems. Thus the dimensions (size and weight) are important drawbacks of such systems. As a result, even if systems for home use are available, the patient must still remain at home (in the same way as a person was at the hospital) due to the non-portable nature of such equipment.

In addition, as dialysis equipment employs an amount of dialysis fluid up to 25 or 40 liters per day (in case of home treatment or up to 120 or 200 liter in dialysis center), the patient has to store at home a large volume of fresh dialysate and the patient hands several dialysate bags (fresh and spent) every day for treatment. Other machines allow transforming water into dialysis solution but these machines use a large amount of energy and water, while representing a potential contamination risk. In both cases, the environmental impact is important. Another drawback of these dialysis systems using tap water is the need for a dedicated water treatment system, which includes large and heavy equipment, water connection and drainage. Installing and using those components is a difficult and cumbersome task that can require a patients home to be modified. As a result the water treatment systems make the home hemodialysis system more non-portable.

Another important drawback is that the HD systems comprise several fluid circuits which have been coupled to the apparatus during the treatment. The old systems comprise one cassette dedicated to the dialysate circuit and a set of tube for the blood circuit. These systems are very difficult to use and just experimented nurses can handle such systems. In order to facilitate the use, some companies designed a single cassette adapted to be coupled to the apparatus. Such cassette comprises a part of the blood circuit and a part of the dialysate circuit making it big. The single cassette was designed to simplify the treatment but in reality such cassette is too large, heavy and difficult to use. Furthermore, in numerous cases the patients note a failure of the coupling between the cassette and the apparatus. Thus this makes laborious use.

General Description of the Invention

All or a part of the mentioned drawbacks may be obviated by the device for dialysis system according to the invention.

One of goals is to have a dialysis system which is more compact, more secure and easier to use in order to be used at home while enabling transportation.

A first aspect of the invention provides a blood treatment system which includes a blood line including a blood cassette (which may be discarded after a single use), a dialysate line including a dialysate cassette (which may be discarded after a single use), a dialyzer (which may be discarded after a single use) including a blood compartment in fluid communication with the blood line and a dialysate compartment in fluid communication with the dialysate line, a dialysis unit (which may be reusable for several treatments and which is preferentially portable).

One of advantages to use two cassettes is that the coupling is facilitated and each cassette may be designed as compact as possible. Furthermore, by using two distinct cassettes, the components in the dialysis unit may be arranged in order to make it more compact and improve the tolerance stack-ups.

A second aspect of the invention provides a blood treatment system comprising at least one cassette for the blood circuit and/or for the dialysate circuit and a dialysis unit. The dialysis unit include components for controlling a dialysis treatment for example a processor, a valve actuator, a sensor, a blood pumping mechanism adapted to cooperate with the blood line in order to move blood through blood line when the blood line is in fluid communication with a blood source and/or a dialysate pumping mechanism adapted to cooperate with the dialysate line in order to move dialysate through the dialysate line when the dialysate line is in fluid communication with a dialysate source. The system further includes a housing in which the components of the dialysis unit is arranged. The housing may have a front panel and a pair of lateral panels, a (blood and/or dialysis) cassette holder arranged into the housing and intended to removably receive the (blood and/or dialysis) cassette and an opening (for example a fixed slot) arranged through the housing intended to allow the cassette to be inserted into the housing (for example horizontally).

The cassette may comprise a handle designed such that it can be gripped by the fingers of a hand of a user. The cassette may be inserted into the housing by a horizontal (or vertical) sliding movement. When the cassette has been inserted into the cassette holder, the handle may protrude out of the housing or may be housed in the cassette compartment. Preferentially, the blood circuit comprises a dedicated cassette and the dialysate circuit comprises a dedicated cassette. In this case two distinct openings may be arranged/designed/adapted for each cassette. One opening may be designed in such a manner to accept/to receive/to allow only its dedicated type of cassette.

A third aspect of the invention provides a system which is easy to move. It is not a system fixed to the patient but a system which may be transported/conveyed in order to allow travelling anywhere in the world. For example, this system comprises all elements needed for the treatment and a housing designed to be movable, with a small size and light weight. For example, the housing of the system may be adapted to be stored in a hand luggage during a travel. The housing may be sized in order to fit into or be smaller than a hand luggage (for example for airplane travel), for example at least one dimension smaller than 31 cm, another dimension smaller than 51 cm and/or another dimension smaller than 61 cm. Furthermore, the hand luggage used for travelling the system may be used as a support, thus during the treatment, the system may be placed in, on or lay on its hand luggage. Other example, the system may comprise a movable container holder for solution bag which may be operatively coupled with the housing of the machine (or with the hand luggage, for example, a (retractable) handle of the hand luggage may be used as the movable container holder) in order to provide a first position and a second position. The first position may be adapted to perform a treatment (for example required in operating configuration) and the second position may be adapted to move easily the system or intended to transport the system, for example during a travel.

The movable container support may comprise a pole fixed to the system by a rotating fixing element adapted to move the pole from the first position to the second position and/or vice versa. The movable container support may comprise a receiver part having a concave shape designed to receive and to store at least one solution bag.

The system may comprise container receiver designed to receive and to store at least one solution bag arranged in an upper portion of the housing. The movable container support may be arranged on a upper portion of the system. A movable container support may be arranged above the container receiver.

A fourth aspect of the invention provides a dialysis system with an easy loading device. For example, the system may comprise a loading device with a drive mechanism of a cassette holder adapted to move the cassette holder until a first position and a second position. The first position may be adapted to allow inserting or removing a cassette (into or form the cassette holder) and the second position may be adapted to perform the treatment. In this case the second position may be adapted to prevent the user from removing and/or from inserting a cassette from or to the cassette holder. This loading system may be operatively coupled to the opening described above.

A fifth aspect of the invention provides a hemodialysis system comprising a priming container (for example a bag) which is in fluid communication with at least one of the blood circuit and the dialysate circuit. In one embodiment, the bag may store a (single) solution (for example dialysate solution or saline solution or other compatible solution) which may be provided to the system for both circuits in order to prime all or a part of the system. The priming container may comprise a first (removable) fluid connection and a second (removable) fluid connection intended to be connected to at least one of the dialysate circuit and the blood circuit.

A sixth aspect of the invention provides a blood treatment system including at least one of:
- a fluid (blood and/or dialysate) line including a fluid cassette,
- a dialysis unit, which may include components for controlling a dialysis treatment including at least one of a processor, a valve actuator, a sensor, and a fluid pumping mechanism adapted to cooperate with the fluid line in order to move the fluid through fluid line when the fluid line is in fluid communication with a fluid source,
- a housing in which the components of the dialysis unit may be arranged, the housing may have a front panel and a pair of lateral panels,
- a component support adapted to hold at least one of the valve actuator, the sensor, the fluid pumping mechanism, and
- a fluid cassette holder arranged into the housing and intended to removably receive the fluid cassette.

The dialysis unit further comprises a loading system comprising a first position required in operating configuration and a second position allowing the insertion or the removal of the fluid cassette. Preferentially, the loading system comprises a drive mechanism controlled by the processor and adapted to enable reaching the first and the second position.

In one embodiment the fluid cassette holder is configured to move relatively to the housing (or the component support) while the component support is fixedly secured to a non-moving part of the system (such as the housing and/or the frame of the system).

In one embodiment the component support is configured to move relatively to the housing (or the fluid cassette holder) while the fluid cassette holder is fixedly secured to a non-moving part of the system (such as the housing and/or the frame of the system).

In one embodiment the component support and the fluid cassette holder are configured to move relatively to the housing (or a non-moving part of the system).

The drive mechanism may adapted to move the cassette holder(s) and/or the component support substantially perpendicularly according to the main plan of the cassette and/or the to the surface on which the system is placed.

The system may further comprise an indicator device adapted to inform the user about the current position of the loading system.

The system may comprise an alignment mechanism configured to align the fluid cassette with the components of the dialysis unit. The alignment mechanism may comprise a part of the fluid pumping mechanism (for example the shaft of the pump which may cooperate with the pump part of the fluid cassette)

The system may further comprise a opening configured to allow the fluid cassette to be inserted into the housing. The opening may be dedicated to a type of fluid cassette. The opening may comprised a fixed slot. The opening may comprise an element having an anti-pinch function.

A seventh aspect of the invention provides a blood treatment system including at least one of:
 a blood line intended to receive a blood of patient,
 a dialysate line intended to receive a dialysate solution,
 a dialyzer including a blood compartment in fluid communication with the blood line and
  a dialysate compartment in fluid communication with the dialysate line,
 a first cassette comprising a part of the blood line,
 a dialysis unit, which includes components for controlling a dialysis treatment including at least one of:
  a processor,
  a first valve actuator,
  a first sensor, and
  a blood pumping mechanism adapted to cooperate with the blood line in order to move blood through blood line when the blood line is in fluid communication with a blood source,
 a housing in which the components of the dialysis unit is arranged, the housing having a front panel and a pair of lateral panels,
 a movable support of components arranged into the housing and adapted to hold at least one of the first sensor and the blood pumping mechanism, and
 a first cassette holder is configured to removably receive the first cassette.

The dialysis unit may further comprise a loading system configured to move the movable support of components to a first position and a second position relatively to the housing while the first cassette holder is fixedly arranged into the housing (for example to a non-moving part of the system (such as a frame)). The first position may be required in operating configuration and the second position may allow the insertion and/or the removal of the first cassette.

The blood pumping mechanism may comprise a shaft and the first cassette may comprise a roller assembly configured to be operatively coupled with the shaft and to align at least in part the cassette relatively to the movable support of components such that at least one of the first valve actuator and the first sensor is aligned to a dedicated area of the cassette, when the movable support of components is in the first position.

The system or the housing may comprise at least one of a fixed slot configured to insert the first cassette into or through the housing and a sliding door. The sliding door may be mechanically coupled to at least one of the movable support components and the loading system in order to open the sliding door when the movable support component is moved to second position.

The first valve actuator may be fixedly arranged into the housing. The first valve actuator may comprise a movable shaft configured to close and open the blood line and the movable shaft may comprise a position configured to allow the insertion and/or the removal of the first cassette.

Preferentially, the first cassette holder comprises a detection sensor configured to send a signal to the processor when the first cassette is inserted into the first cassette holder. The processor may be configured to initiate a displacement of the movable support of components depending on the signal of the detection sensor.

The system (for example the opening and/or the cassette holder) may comprise a coding element configured to prevent the insertion of other type of cassette.

The system (for example the opening and/or the cassette holder) may comprise a lock system configured to cooperate with the first cassette in order to prevent the withdrawal of the first cassette when the movable support of components is in first position.

One embodiment the system further comprise at least one of:
 a second cassette distinct from the first cassette and comprising a part of the dialysate line,
 a dialysate pumping mechanism adapted to cooperate with the dialysate line in order to move dialysate through the dialysate line when the dialysate line is in fluid communication with a dialysate source,
 a second sensor, and
 a second valve actuator.

One embodiment the system further comprise at least one of:
 a second cassette holder distinct from the first cassette holder and configured to removably receive the second cassette and
 an additional movable support of components distinct from the movable support of components arranged into the housing and adapted to hold at least one of the second sensor, the second valve actuator, and the dialysate pumping mechanism, The loading system may configured to move the additional movable support of components to a third position and a fourth position relatively to the housing while the second cassette holder is fixedly arranged into the housing (for example to a non-moving part of the system (such as a frame)). The third position may be required in operating configuration and the fourth position may allow the insertion and/or the removal of the second cassette.

LIST OF FIGURES

The present invention will be better understood at the light of the following detailed description which contains non-limiting examples illustrated by the following figures:
 FIG. 1 shows a schematic view of the fluid circuits;
 FIGS. 2a, to 2f illustrate different views of embodiments of the blood circuit;
 FIG. 3 illustrates a dialysate circuit according to one embodiment;
 FIG. 3a illustrates a dialysate circuit with sensors according to one embodiment;
 FIG. 4 shows the interaction between the disposable part and the reusable part;
 FIGS. 5a to 5c' illustrate cross-sectional views of cassette;
 FIG. 6 shows the elements of the fluid pump;

FIGS. 30a to 30h illustrate several positions of the door device.

Figure 1:
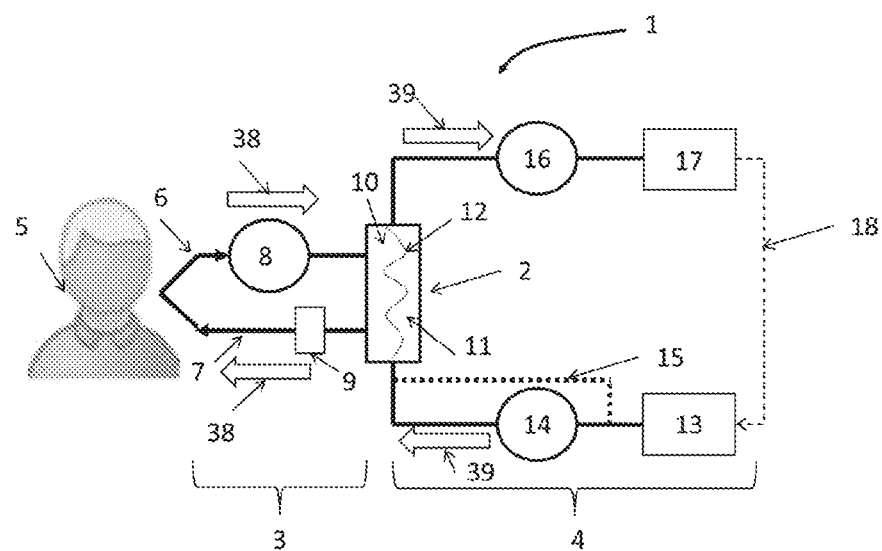

Some figures do not show all features so as to render the figure clearer.

LIST OF ELEMENTS 1 extracorporeal blood treatment system
2 dialyzer
3 blood circuit
4 dialysate circuit
4' additional circuit/line for example (concentrate or initial supply circuit)
5 patient
6 arterial line
7 venous line
8 blood pump
9 drip chamber
10 first chamber
11 second chamber
12 membrane
13 bag/container
14 first dialysate pump
15 dialysate line
15' by pass line
16 second dialysate pump
17 element for receiving the solution from the dialyzer
18 loop line
19 container (blood return container)
19' drain container or drain compartment
20 line
21 valve
22 line
23 valve
24 arterial valve
25 venous valve
26 arterial connector
27 venous connector
28 initial supply container
29 weight balance
30 pump
31 supply container (for example concentrate supply bag)
32 supply container
33 single priming container
34 first connector
35, 35' second connector
36 third connector
37 dialysate circuit connector
38 normal flow direction (blood circuit)
39 normal flow direction (dialysate circuit)
40 potential limit of the cassette
41 supply container
42 normal pumping direction
42 reversed pumping direction
43 sorbent connector
44 first spike
45 second spike
100 blood purification system
101 disposable part
102 reusable part/apparatus
103 dialyzer
104 sorbent
105 bag
106 cassette
107 rigid frame
108 membrane
109 handle
110 processor
111 screen (device for example tablet with a touch screen)
112 other element such as button
113 sensor
114 actuator
115 other elements connected to the processor and operatively and removably coupled to the disposable part
116 tube
120 cavity
121 port
122 handle
123 valve seat
124 fluid pathway
200 cassette with a part of a pump
201 flexible tube
202 fluid pathway of the cassette
203 inlet port of the pump
204 outlet port of the pump
205 roller assembly
206 roller support
207 shaft
208 roller
300 apparatus (reusable part)
301 housing 302 display device
303 screen support
304 container support
305 additional screen
306 power button
307 emergency button
308 dialyzer support
309 drip chamber support
310 first opening
311 second opening
312 pole
313 hook
314 rotating fixing element
315 movable container support
316 container receiver
317 fixing element
318 recess
319 first portion
320 second portion
321 front panel
322 side panel
323 side panel
324 opening of the first side
325 opening of the second side
326 insertion direction
327 first side of the housing
328 second side of the housing
400 loading system
401 cassette holder
402 dedicated active element (for example sensor)
403 dedicated active element (for example valve actuator)
404 dedicated active element (for example motor of the pump)
405 shaft of the motor
406 support of the dedicated active elements
407 movement of the cassette holder
408 movement of the dedicated active element
409 drive mechanism
410 motor
411 drive assembly
412 guiding assembly
412' guiding or sliding element
413 support of guiding element
414 pin
415 door
416 door actuator
417 housing interior
418 lock system
419 opening
420 part of housing
421 elastic element
422 coupling element
423 flexible element
500 drip chamber support
501 drip chamber
502 body
503 lock
504 mechanical coding system
600 dialysis system
601 apparatus
602 blood cassette
603 dialysate cassette
604 first door
605 second door
606 dialyzer
607 housing
608 dialyzer support
609 pole
610 display device
611 weighting scale
612 sorbent device
613 tubes
614 weighting bag
615 apparatus support
700 dialysis system
701 apparatus
702 blood cassette
703 dialysate cassette
704 door
705 heating compartment
706 dialyzer
707 housing
708 dialyzer support
709 pole
710 display device
711 weighting scale
712 sorbent device
713 tubes
714 weighting bag
715 apparatus support

DETAILED DESCRIPTION OF THE INVENTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. It is to be understood that even if the document describes a haemodialysis system, some embodiments described therein may also be used for or arranged in a peritoneal dialysis system or other blood treatment purification systems such as for example continuous renal replacement therapy (CRRT). The following detailed description, therefore, is not to be taken in a limiting sense.

All scientific and technical terms used herein have meanings commonly used in the art unless otherwise specified. The definitions provided herein are here to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and orientations.

As used herein, "have", "having", "include", "including", "comprise", "comprising" or the like are used in their open ended sense, and generally mean "including, but not limited to.

As used herein, "at least one of A, B, and C", "at least one of A, B or C", "selected from the group consisting of A, B, C, and combinations thereof" or the like are used in their open ended sense including "only A, or only B, or only C, or any combination of A, B and C" unless the content clearly dictates otherwise.

As used in this specification and the appended claims, the term "or" and "/" are generally employed in its sense including "and/or" unless the content clearly dictates otherwise.

As used herein, "compatible solution with blood" or the like generally means "a physiologically compatible solution for contacting blood, a physiologically compatible solution for infusion to a subject or a solution for blood rinse back to a subject".

The texts or terms written in brackets have to be understood as an optional feature, a synonym, the similar terms or an example.

Fluid Circuit(s)

Referring to the FIG. 1, the extracorporeal blood treatment system 1 may comprise a dialyzer 2, a blood circuit 3 and a dialysate circuit 4.

The blood circuit 3 (also called extracorporeal circuit) connects the patient 5 to the dialyzer 2. More specifically, the blood circuit 3 comprises an arterial (blood) line 6 and a venous (blood) line 7 which connect the patient 5 to the dialyzer 2. The arterial line 6 may comprise a removable arterial connector 26 intended to be connected to a patient and the venous line 7 may comprise a removable venous connector 37 intended to be connected to a patient. The blood circuit 3 comprises at least one pump 8 for pumping fluid through the blood circuit, for example blood to or from the dialyzer 2. The blood pump 8 may be, for example, a peristaltic pump, a pumping chamber, . . . . Further, a clamp may be arranged and located in the blood circuit 3, for example a valve. Still further, an air sensor may be located within the extracorporeal circuit. The air sensor may, for example, detect the presence of air within the extracorporeal circuit. A drip chamber may be arranged and located within the extracorporeal circuit, for example in the venous line 7. The drip chamber may, for example, remove the air bubbles present in the blood circuit. An air sensor may be arranged downstream a drip chamber and/or upstream at least one of a valve and the removable venous connector 27. Air (or other fluid or gas) may be present in the blood circuit 3 prior to the treatment. As a result, the patient or other health professional may need to prime the extracorporeal circuit 3 by removing it, as described thereafter.

The dialyzer 2 has a first chamber/compartment 10 in which the blood is moved through, an arterial (blood) port by which the blood is entered and a venous (blood) port by which the blood is exited from. The dialyzer 2 has a second chamber/compartment 11 in which a dialysate solution is moved through, a first (dialysate) port by which the dialysate solution (more particular a fresh dialysate or regenerated dialysate) is entered and a second (dialysate) port by which the dialysate solution (more particular an used dialysate) exits the dialyzer. The used dialysate is a dialysate solution which exits from the second dialysate port and may comprise ultra-filtrate (mixed to other liquids). The ultra-filtrate is a liquid which comprises the excess water of the patient. The dialyzer 2 has a membrane 12 separating the first chamber from the second chamber. The membrane may be adapted (for example, the membrane may be semi permeable) to allow passage of fluid or components from the first chamber to the second chamber (and/or inversely from the second to the first chamber).

The dialysate circuit 4 comprises at least one pump adapted to convey a fluid through the dialysate circuit 4, for example a dialysate solution to or from the dialyzer 2. Preferentially, the dialysate circuit 4 may have a first dialysate pump 14 adapted to pump a solution (for example, a solution stored in the bag 13) to the dialyzer 2. The bag 13 may store a dialysate solution as a fresh dialysate or other solution as a priming solution. The bag 13 may be initially empty. The bag 13 may be in fluid communication with the dialyzer 2 via a fluidic line. This fluidic line may include the first dialysate pump 14 or may be a by-pass adapted to by-pass the fluidic line including the first dialysate pump 14. The fluidic line may comprise a valve in order to open or close the fluidic communication between the bag 13 and the dialyzer 2. The dialysate circuit 4 may have a second dialysate pump 16 adapted to pump the solution exiting from the dialyzer 2, such as the used dialysate and/or the ultra-filtrate. This solution may be moved up to an element 17 which is adapted to receive for example the used dialysate and/or ultratfiltrate. This element may be a bag (adapted to store the solution) or a sorbent device (adapted to clean or to regenerate the solution). The dialysate circuit may comprise a loop line 18 adapted to allow a fluid communication between the bag 13 and the element 17 (in particular when the element 17 is a sorbent). In this case the bag 13 comprises an outlet in fluidic communication with the dialyzer 2 and an inlet in fluidic communication with the element 17 (for example a sorbent device). The dialysate circuit may comprise at least one of valve and sensor such as a pressure sensor, level sensor, weight scale, flow meter, blood sensor, ammoniac sensor, . . . . The dialysate pump may be, for example, a peristaltic pump, a pumping chamber, . . . . Air (or other fluid or gas) may be present in the dialysate circuit prior to the treatment. As a result, the patient or other health professional may need to prime the dialysate circuit by removing it, as described thereafter. A by-bass may be arranged between the second dialysate pump 16 and the bag 13 in order to by pass the element 17 (for example the sorbent device when the sorbent is no longer usable).

Blood Circuit

Turning now to the FIG. 2, the blood circuit may comprise a bag 19 adapted to receive and/or to store a solution and to be in direct fluid communication with the arterial line and/or with the venous line. The term "direct fluid communication" is employed here as "physically and fluidly connected to and in fluid communication at least temporarily with" without passing by another fluid pathway, filter, dialyzer, sorbent or pump. A valve may be used in order to control (by the apparatus, automatically or not) the direct fluid connection. The bag 19 may be empty at the start of the treatment. The bag 19 may be filled with a saline solution or other compatible solution with blood. The bag 19 may be used to prime the blood circuit and/or to push the blood back to the patient, as described thereafter.

Preferentially, the bag 19 may be initially substantially empty (of liquid and/or of gas) and sterilised. During the priming process of the blood circuit, the bag 19 may be filled with a priming solution (which may be a saline solution or a dialysate solution or other) and/or with the fluid (for example the gas) initially stored in the fluid pathway of the blood circuit before the treatment. The bag 19 may comprise a degassing device such as a vent with a hydrophobic membrane in order to expel the gas (for example air) which may be stored or injected into the bag (the storing compartment of the bag). The bag 19 may be sized in order to store a volume of fluid which is substantially equivalent or superior (for example more or less twice the volume defined thereafter) to a volume defined by the interior wall of the blood circuit (for example the volume defined by the interior of the tube, of the cassette, of the blood compartment of the dialyzer and/or of the drip chamber . . . ). The bag 19 may be advantageously filled with the priming solution during the priming process, then the bag stores this solution during the treatment and at the end of the treatment, this solution may be used to push the blood back to the patient.

A volume fraction of the solution stored in the bag 19 may be injected into the blood circuit in the event of blood pressure reduction of the patient during the treatment. Thus, the system limits the amount of fluid necessary for the priming and the rinsing back process, even more when the priming solution is a dialysate solution or saline solution. Thus only one liquid solution (or a limited number of distinct solutions) may be prepared or added or used for the treatment (or at least a limited number of bags). In case where the system uses a sorbent and a concentrate solution(s), only two (or less than three) types of solution may be used a dialysate solution (and/or saline solution) and one or more concentrate solutions for the overall treatment.

A solution stored in a bag connected 28 or 33 (in direct fluid communication with) (for example shown by the FIG. 20 or 21) to the dialysate circuit (and optionally to the blood circuit) may be used to prime the blood circuit and/or to fill the bag 19. This solution may be a saline solution or a dialysate solution.

Figure 2A:
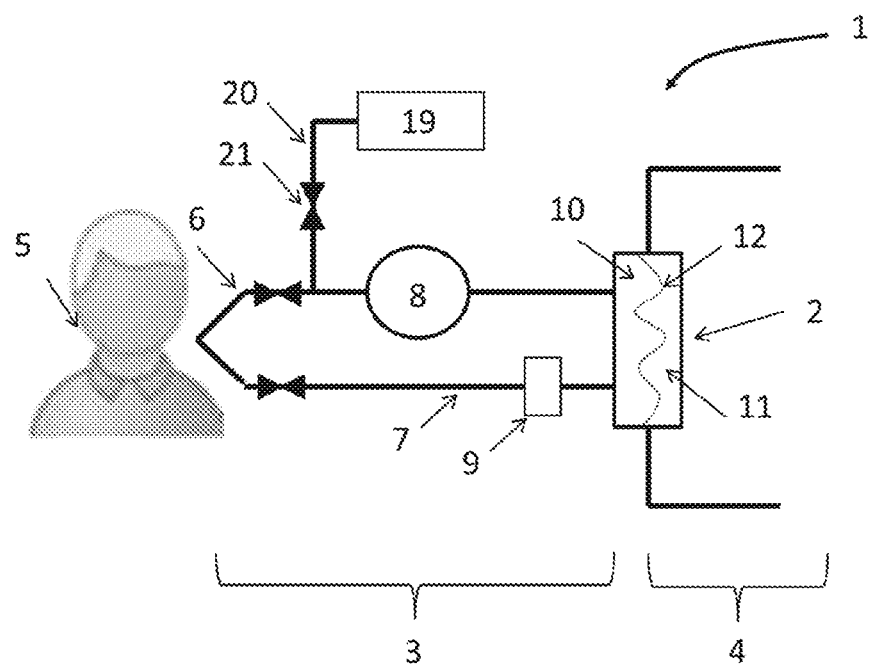

According to the FIG. 2a, the blood circuit comprises a line 20 which is in direct fluid communication with the arterial line and with the interior (for example storing compartment) of the bag 19. The connection between the line 20 and the arterial line 6 is arranged or located upstream ("upstream" according to the normal flow direction) of the pump 8 and preferentially downstream the arterial connector 26. The normal flow direction is indicated in FIG. 1 by arrow 38 for the blood circuit and arrow 39 for the dialysate circuit. The line 20 may comprise a (removable) connector and/or a valve 21 (V3) which may be controlled in order to open or to close the fluid communication by a controller device for example a processor.

Figure 2B:
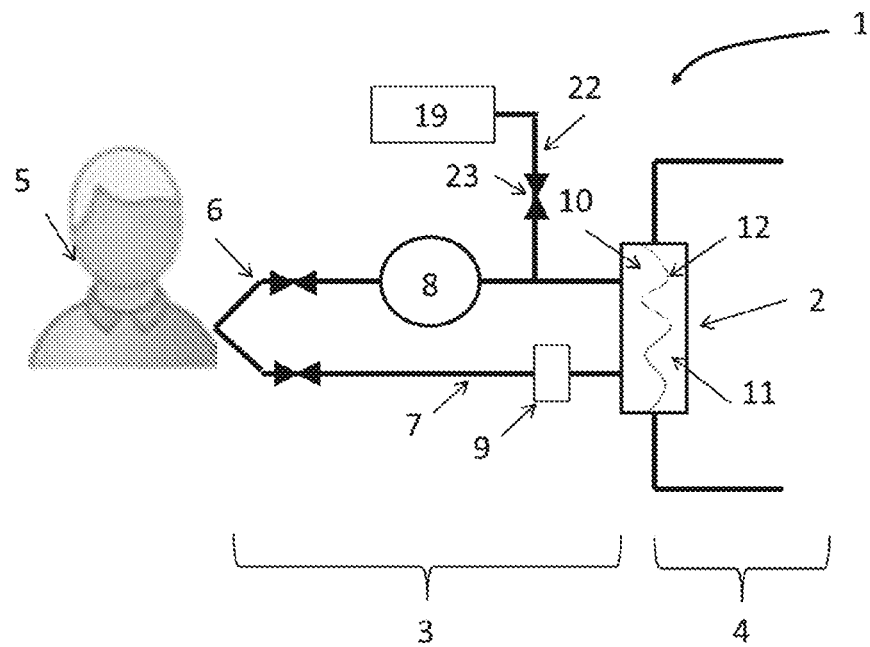
Figure 2C:
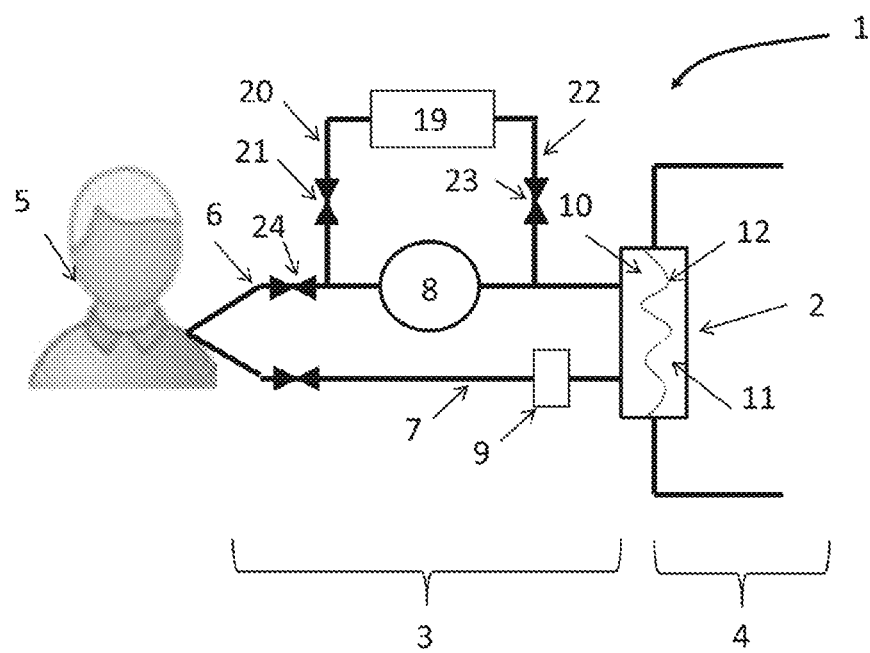

According to the FIG. 2b, the blood circuit comprises a line 22 which is in direct fluid communication with the arterial line and with the interior (for example storing compartment) of the bag 19. The connection between the line 22 and the arterial line 6 is arranged or located downstream the pump 8 ("downstream" according to the normal flow direction) and preferentially upstream to the venous connector 27 (for example upstream of at least one of the venous valve, the drip chamber and the dialyzer). The line 22 may comprise a (removable) connector and/or a valve 23 (V4) which may be controlled in order to open or to close the fluid communication by a controller device for example a processor. In another embodiment as partially described by the FIG. 2d, the blood circuit may comprise a line 22 which is in direct fluid communication with the venous line 7 and with the interior (for example storing compartment) of the bag 19. The connection between the line 22 and the venous line 7 is arranged or located downstream the pump 8, for example upstream or downstream of the dialyzer (according to the normal flow direction). The line 22 may comprise a valve 23 (V4) which may be controlled in order to open or to close the fluid communication by a controller device for example a processor According to the FIG. 2c, the blood circuit comprises a line 20 which is in direct fluid communication with the arterial line and with the interior (for example storing compartment) of the bag 19. The connection between the line 20 and the arterial line 6 is arranged or located upstream ("upstream" according to the normal flow direction) the pump 8. The line 20 may comprise a valve 21 (V3) which may be controlled in order to open or to close the fluid communication by for example a processor. The blood circuit further comprises a line 22 which is in direct fluid communication with the arterial line and with the interior (for example storing compartment) of the bag 19. The connection between the line 22 and the arterial line 6 is arranged or located downstream the pump 8 but upstream the dialyzer. The line 22 may comprise a valve 23 (v4) which may be controlled in order to open or to close the fluid communication.

Figure 2D:
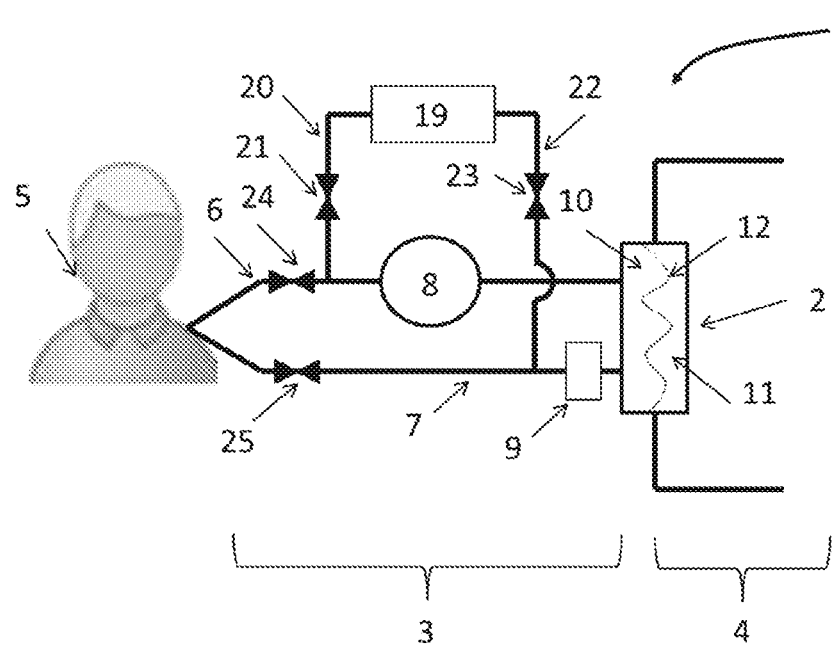

According to the FIG. 2d, the blood circuit comprises a line 20 which is in direct fluid communication with the arterial line and with the interior (for example storing compartment) of the bag 19. The connection between the line 20 and the arterial line 6 is arranged or located upstream ("upstream" according to the normal flow direction) the pump 8. The line 20 may comprise a valve 21 (V3) which may be controlled in order to open or to close the fluid communication by for example a processor. The blood circuit further comprises a line 22 which is in direct fluid communication with the venous line 7 and with the interior (for example storing compartment) of the bag 19. The connection between the line 22 and the venous line 7 is arranged or located downstream the pump 8 (and/or the dialyzer and/or the drip chamber). The line 22 may comprise a valve 23 (v4) which may be controlled in order to open or to close the fluid communication.

The blood circuit may comprise an arterial valve 24 (V1) arranged and located in the arterial line 6. The arterial valve 24 may be controlled in order to open or close the arterial line. The arterial valve may be arranged/located upstream the pump 8 and/or upstream the line 20 and/or the line 22. The blood circuit may comprise a venous valve 25 arranged and located in the venous line 7. The venous valve 25 may be controlled in order to open or close the venous line 7. The venous valve may be arranged/located downstream the pump 8 and/or downstream the line 20 and/or the line 22 and/or downstream the drip chamber 9. The arterial valve 24 and/or the venous valve 25 may be arranged into the blood cassette and may comprise flexible tube which may be pinched by a pinch valve.

Figure 2E:
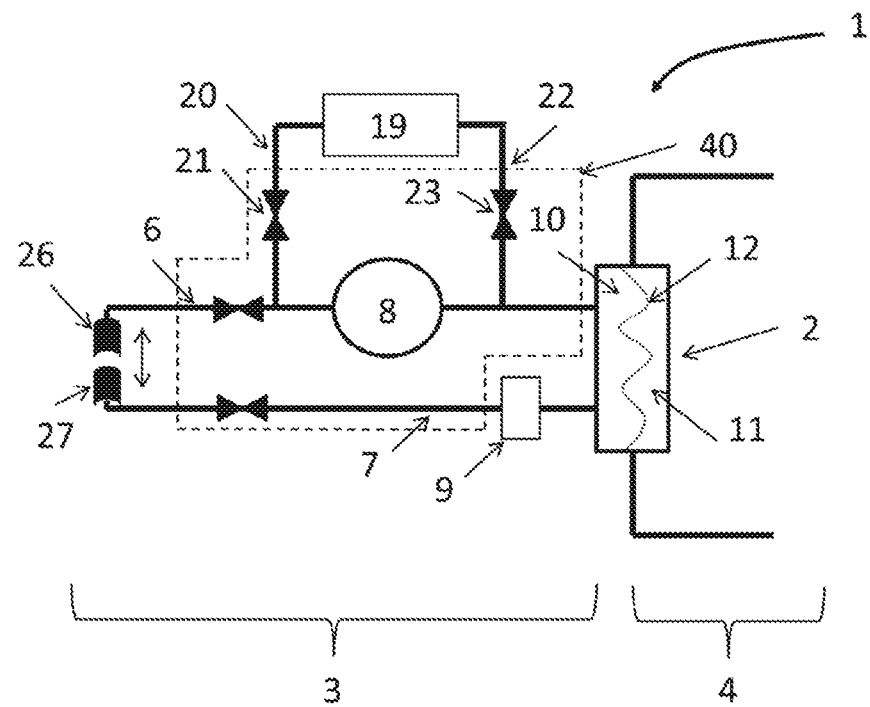

According to the FIG. 2e, the blood circuit comprises an arterial connector 26 arranged/located at an end of the arterial line 6. The arterial connector 26 is adapted and intended to be connected to a catheter of the patient. And the blood circuit comprises a venous connector 27 arranged/located at an end of the venous line 7. The venous connector 27 is adapted and intended to be connected to a catheter of the patient.

The arterial connector 26 and the venous connector 27 may be adapted to be connected together in order to allow a fluid communication between the arterial line 6 and the venous line 7 (without requiring to pass through the dialyzer) and to create a (closed) loop of the blood circuit. If the arterial connector 26 and the venous connector 27 cannot be directly connected together, the system may comprise an interconnector device comprising a first end adapted and intended to be connected to the arterial line 6 and a second end adapted and intended to be connected to the venous line 7. The interconnector device allows a fluid communication between the arterial line 6 and the venous line 7 and creates a (closed) loop of the blood circuit.

Figure 2F:
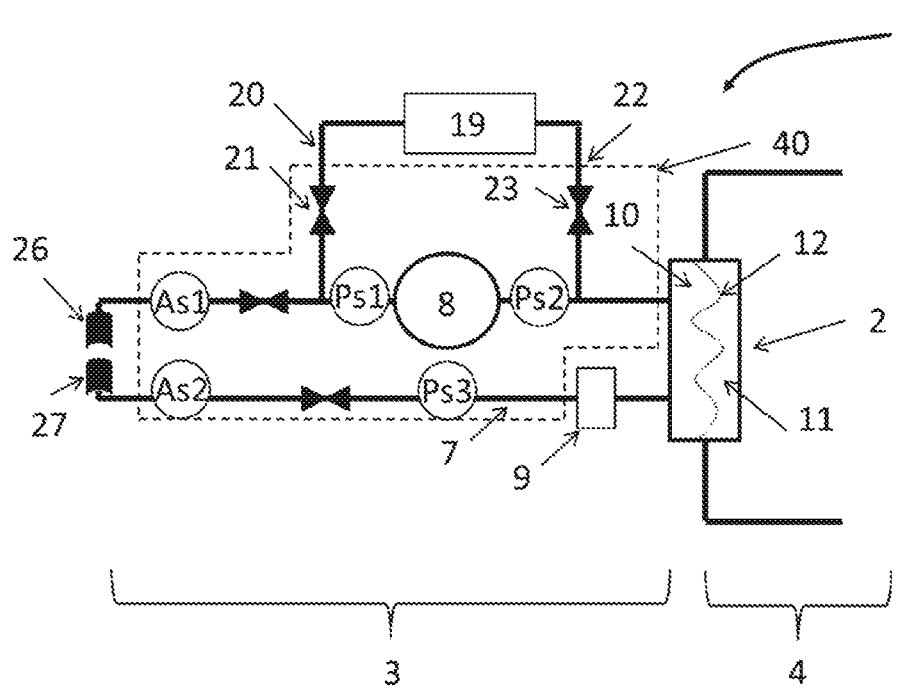

According to the FIG. 2f, the blood circuit may further comprise at least one of an air sensor (As1, As2) and a pressure sensor (Ps1, Ps2, Ps3). Preferentially, a first air sensor may be configured to cooperate with the arterial line 6 and a second air sensor may be configured to cooperate with the venous line 7. The air sensor may be configured to cooperate with the fluid pathway of the blood cassette. The first air sensor may be arranged downstream the arterial connector but preferentially upstream the arterial valve. The second air sensor may be arranged upstream the venous connector but preferentially downstream the venous valve. Preferentially, a first pressure sensor and a second pressure sensor may be configured to cooperate with the arterial line 6 and a third pressure sensor may be configured to cooperate with the venous line 7. The pressure sensor may be configured to cooperate with the fluid pathway of the blood cassette. The first pressure sensor may be arranged upstream the blood pump 8 but preferentially downstream the connection with the line 20. The second pressure sensor may be arranged downstream the blood pump 8 but preferentially upstream the connection with the line 22. The third pressure sensor may be arranged upstream the venous valve but preferentially downstream the drip chamber.

Dialysate Circuit

Figure 3:
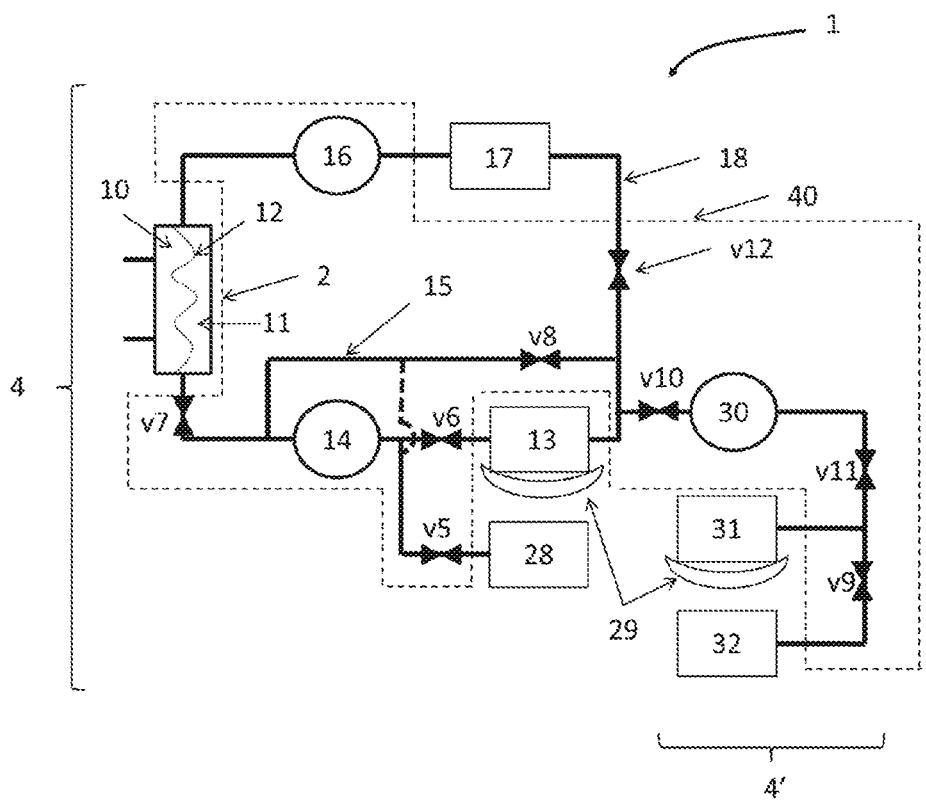

Referring now to the FIG. 3, the dialysate circuit may have a bag 28 which may store a solution for example a dialysate solution (such as an initial supply of dialysate) or a priming solution (which may be dialysate solution, a saline solution or other). This bag 28 may be used to add liquid solution into the loop circuit of dialysate or to initially fill the bag 13 (if the bag is initially empty for example before starting the treatment) or to prime at least a part of the circuit(s). The bag 28 may be in direct fluid communication with the first dialysate pump 14 via a line which may comprise a valve v5. The bag 28 may be in direct fluid communication with the by-pass line 15 via a line which may comprise a valve v5, in this case, the bag 28 may be used so as to remove a volume fraction of the solution from the dialysate loop circuit, for example from the bag 13 (close V8 and V7, open V6 and V5 and actuate the first dialysate pump). The by-pass line 15' may comprise a valve v8. The loop line 18 may comprise a valve v12. The bag 13 may be in direct fluid communication with the first pump via a line comprising a valve v6.

The dialysate circuit may have a supply circuit/line 4' (also called an additive circuit or concentrate circuit). This supply circuit 4' may comprise at least one supply pump (for example a concentrate pump 30) in fluid communication with the loop circuit of dialysate for example to the loop line 18 or to the bag 13 in order to add a solution (for example concentrate or saline or dialysate or other fluid different from dialysate) into the loop circuit of the dialysate upstream of the bag 13 or directly into the bag 13. This supply circuit may have a flow meter or a balance chamber in order to control or to monitor the concentrate adds to the loop circuit of the dialysate. The supply pump may be adapted to control and/or to monitor the amount of concentrate added to the loop circuit of dialysate. The supply circuit may comprise a valve v10 located downstream the supply pump 30 and/or upstream to the connection with the loop circuit of the dialysate. The supply circuit 4' may comprise one or more bag (31, 32) which may store a solution such as a concentrate solution (also called diluted solution or additive solution), a saline solution and/or a dialysate solution for example an initial supply of dialysate or other solution different from dialysate. This supply circuit may be also used so as to remove a volume fraction of the solution from the dialysate loop circuit. In this case the supply pump 30 is accurate in reverse mode the bag 32 may receive the removed solution. The bag 32 may be weight in order to monitor the volume of removed solution.

In one embodiment, the supply bag 32 stores a saline solution or pure water and the system does not comprise any initial supply bag of dialysate. Thus the dialysate is prepared from the saline solution or pure water and concentrate solution before starting the treatment into the bag 13 which may be initially empty. The processor may take into account the fact that the prepared dialysate solution will be regenerated/recycled through the sorbent device multiple times during the treatment and thus prepare a predetermined initial volume of dialysate solution before starting the treatment. In particular, the volume of dialysate solution initially prepared may be smaller than the volume of dialysate solution used at the end of the treatment due to the UF and/or the volume of added concentrate accumulated during the treatment.

The dialysate circuit 4 may be adapted to allow flowing, pumping, circulating a fluid in two opposite directions for example through the by-pass line 15. The dialysate pump may be adapted to pump in two directions for example in a first direction from the bag 13 to the dialyzer and a second direction which is a direction opposite to the first direction.

The bag 28 may be used to fill the bag 13 by actuating the dialysate pump in the first direction (if the bag 28 is connected to the line of the pump), in this case the solution initially stored in the bag 28 passed through the pump 14, then through the line 15 and reach the bag 13. V6 and V7 are closed and V5 and V8 are opened. If the bag 28 is connected to the line 15 (via the dash line), the bag 28 may be used to fill the bag 13 by actuating the dialysate pump in the second direction, the solution initially stored in the bag 28 is passed through the line 15, then through the pump 14 and reach the bag 13. V7 and V8 are closed and V5 and V6 are opened.

The system may comprise one or more balance (weight scale) and/or a heater 29 adapted to weigh or heat the solution store in at least one of the bag 13 13, 28, 31 and 32.

Preferentially, the dialysate circuit comprises a sorbent device adapted to clean the used dialysate, in order to use the dialysate solution several times. In this case, the concentrate solution may be added into the dialysate circuit over the course of treatment. Thus, a treatment may be performed with less than 10 liters of initial dialysate, preferentially less than 5 liters of initial dialysate, and more preferentially less than 4 liters of initial dialysate.

Figure 3A:
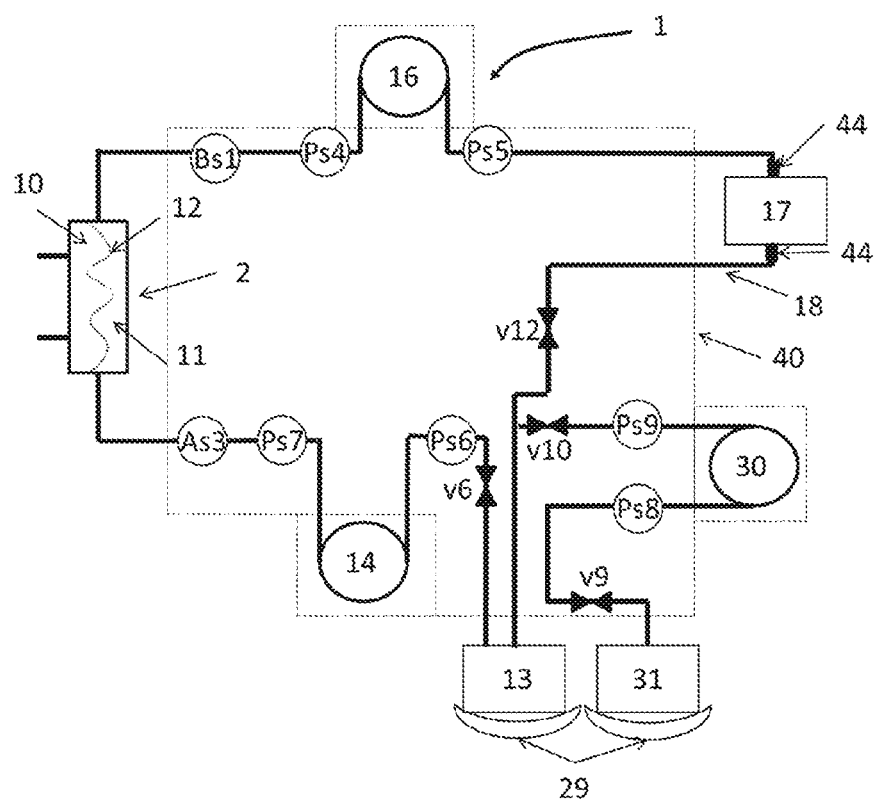

According to the FIG. 3a, the dialysate circuit may further comprise at least one of an air sensor (As3), a pressure sensor (Ps4, Ps5, Ps6, Ps7, Ps8, Ps9) and a blood sensor (Bs1). Preferentially, a third air sensor (As3) may be configured to cooperate with the dialysate line. The air sensor may be configured to cooperate with the fluid pathway of the dialysate cassette. The third air sensor may be arranged upstream the dialyzer 2 but preferentially downstream the bag 13.

Preferentially, at least one pressure sensor of the dialysate circuit may be configured to cooperate with the fluid pathway of the dialysate cassette and more particularly with at least pumping device of the dialysate circuit (or connected line). Thus, each pumping device may comprise a pressure sensor located upstream the pumping device and another pressure sensor located downstream the pumping device.

Preferentially, a blood sensor (Bs1) may be configured to cooperate with the dialysate line. The blood sensor may be configured to cooperate with the fluid pathway of the dialysate cassette. The blood sensor may be arranged downstream the dialyzer 2 but preferentially upstream the pump 16.

Single Priming Container

The system may comprise a (single) priming container 33 (for example shown by the FIGS. 20 and 21) in fluid communication with at least one of the blood circuit and the dialysate circuit during the priming process in order to prime at least a part of both circuits. As the other bag of the system, the single priming container 33 may be a bag having one or more flexible wall sealed to a rigid wall another flexible wall.

The system may comprise a dialysate circuit having a dialysate connector 37, a blood circuit having an arterial connector 26 and a venous connector 27 and a priming container having a storage compartment. The system may be adapted to provide a fluid connection (only during the priming process of the system before starting the treatment) between the storage compartment of the priming container 33 and the connectors (dialysate connector, arterial connector and venous connector).

The system may further comprise at least one of a first pump dedicated to the blood circuit, a second pump dedicated to the dialysate circuit, a memory having computer-executable instructions dedicated to the priming process, a processor connected to the memory and the pumps. Both pumps may be adapted to move the priming solution (initially stored in the priming container) through the fluid circuits. The processor is adapted to control the pumps (successively or simultaneously) according to the computer-executable instructions in order to automatically perform all or a part of the priming process.

The single priming container may store a saline solution, a dialysate solution or other compatible solution (compatible with blood and/or dialysate).

If the single priming container stores a saline solution or other compatible solution to prepared dialysate solution (for example pure water, . . . ), at least a part of the dialysate solution (used for the treatment) may be automatically prepared from this stored solution. In this case, a volume fraction of the solution initially stored in the single priming container is added to the bag 13 in order to prepare a dialysate solution before starting the treatment and a concentrate solution may be also added to the bag 13. In this case, the processor may be programmed in order to automatically move a predetermined volume fraction of the solution (initially stored in the container 33) to the bag 13 and a predetermined volume fraction of concentrate solution (initially stored in the container 31) to the bag 13. The processor may take into account the fact that the prepared dialysate solution will be regenerated/recycled through the sorbent device multiple times during the treatment and thus prepare a predetermined initial volume of dialysate solution before starting the treatment. In particular, the volume of dialysate solution initially prepared may be smaller than the volume of dialysate solution used at the end of the treatment due to the UF and/or the volume of added concentrate accumulated during the treatment. Furthermore, the priming solution may be also added to the bag 19 (of the blood circuit) and used at the end of the treatment as described above.

If the single priming container stores a dialysate solution or other compatible solution with the blood, a volume fraction of the solution initially stored in the single priming container may be added to the bag 13 (for example if the bag 13 is empty at the beginning of the treatment). Furthermore, the priming solution may be also added to the bag 19 and used at the end of the treatment as described above.

Thus, a (the single) priming container may be used to supply a solution to the bag 19 and/or to the bag 13 and/or to prime the blood circuit 3 and/or the dialysate circuit 4. In other terms, the volume of the storage compartment of the single priming container may take into account a required volume for the bag 13, a required volume for the bag 19 and/or a required volume for priming the fluid pathway of both circuits (for example the pathway, the dialyzer, the sorbent, . . . ).

The single priming container may comprise one, two or three outlets.

Figure 20:
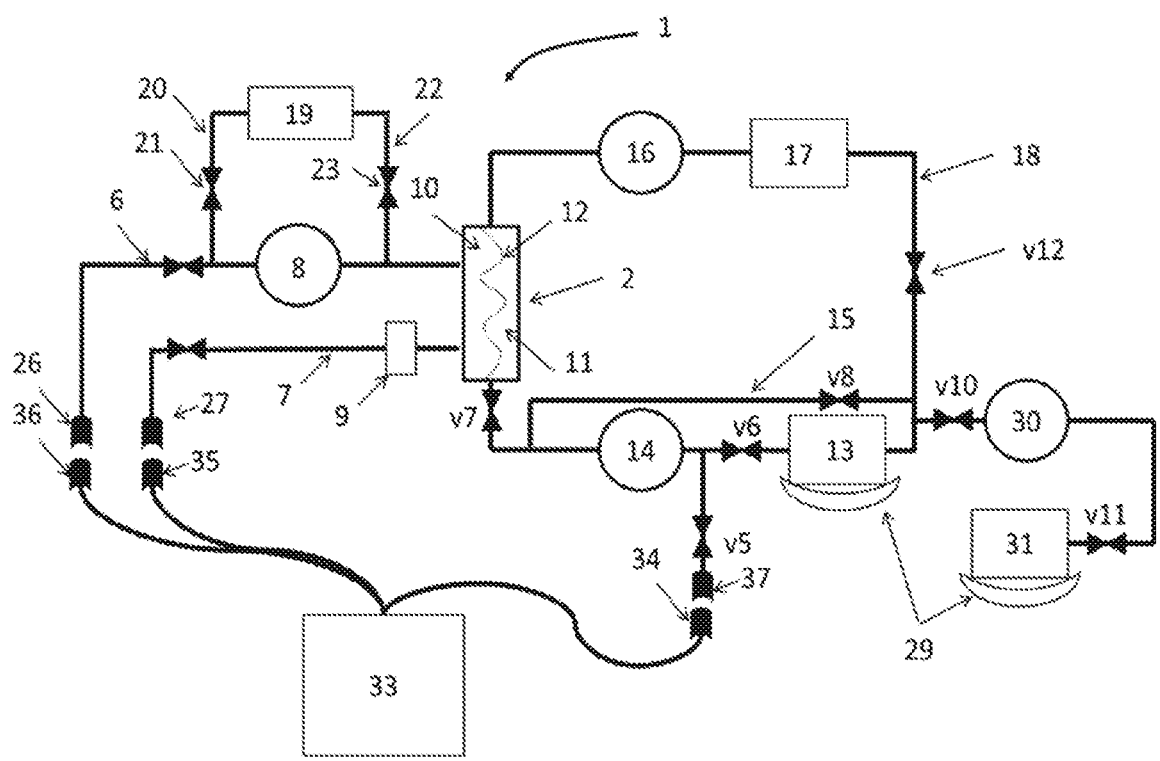
FIGS. 20 and 21 show an illustration of the system using a priming container.

Referring now to the FIG. 20, the single priming container 33 comprises three outlets, for example three tubes and/or three connectors. Each outlet is in fluid communication with the solution stored in the container and may comprise a dedicated connector. A first connector 34 may be adapted or intended to be connected to a dialysate circuit connector 37. This dialysate circuit connector may be connected to a tube which may extend up to the dialysate cassette. A clamp or a valve V5 may be used to clamp or to close this fluid pathway. In the cassette, this fluid pathway may be in fluid connection with the dialysate circuit for example to the fluid pathway between the bag 13 and the pump 14 (as the bag 28 which is used in an other embodiment). A second connector 35 may be adapted or intended to be connected to the venous connector 27 and a third connector 36 may be adapted or intended to be connected to the arterial connector 26.

Figure 21:
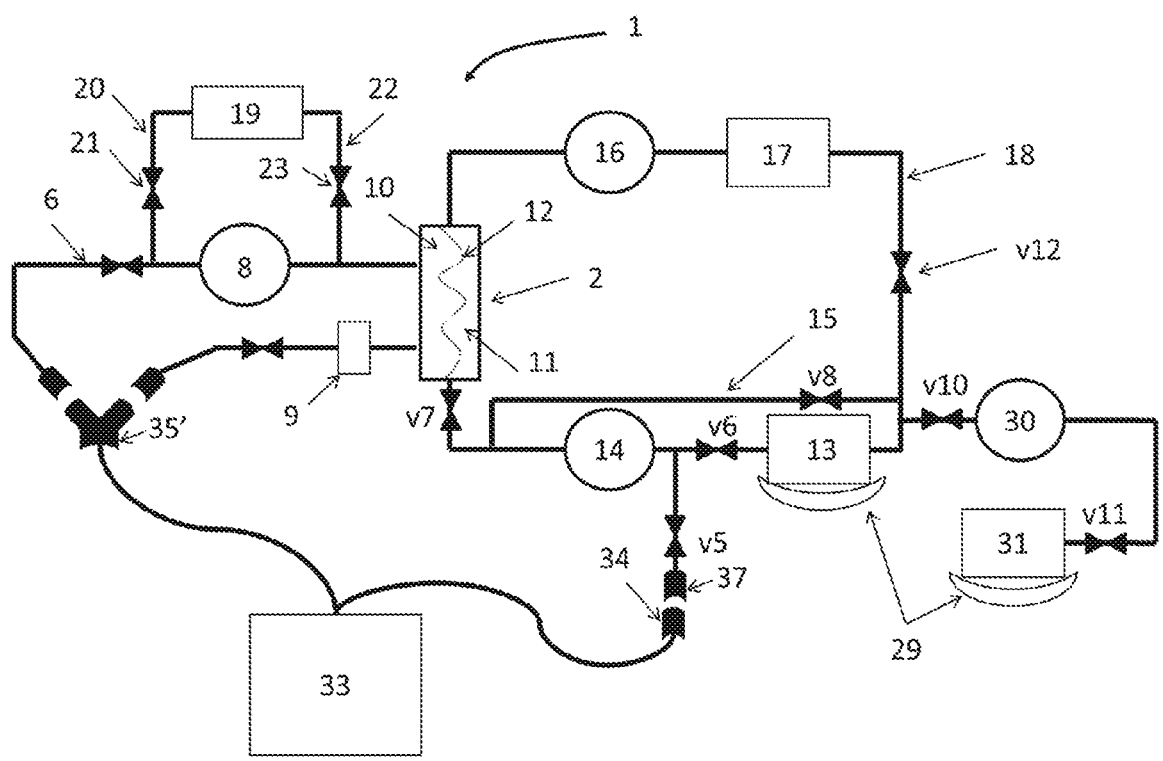

Referring now to the FIG. 21, the single priming container comprises two outlets, for example two tubes and/or two connectors. Each outlet is in fluid communication with the solution stored in the container and may comprise a dedicated connector. A first connector 34 may be the same of the connector 34 described above via the FIG. 20. A second connector may have one or two ports. If the second connector 35 has only one port, the system needs to have an adapter so as to connect the second connector to the arterial connector 26 and to the venous connector 27. If the second connector 35 has two ports, a first port may be is adapted or intended to be connected to the venous connector 27 and a second outlet port may be adapted or intended to be connected to the arterial connector 26.

If the single priming container comprises only one outlet for example one tube and/or one connector, this connector may have three ports (one for the dialysate circuit and two for the blood circuit as described above) or the system may use an adapter having one inlet port and three outlet ports as the concept described above.

Overall System

The overall system may have a reusable part and a disposable part. The disposable part comprises the elements which have to be discarded after a predetermined number of uses, for example, after a single use. The working life of the disposable part may directly depend on the number of treatment. These elements may be the elements which have been wetted by the dialysate or by the blood, for example, at least part of the blood circuit and/or at least a part of the dialysate circuit and/or the dialyzer.

The disposable part of the blood circuit may comprise at least one of a tube, a connector, a port, a cassette, a valve, . . . . The disposable part of the dialysate circuit may comprise at least one of a tube, a connector, a port, a cassette, a valve, . . . .

Preferentially, the reusable part comprises the expensive elements for example the sensor, the electronic part, the screen, the actuator of the valve or of the pump, the processor, the memory. The reusable part is successively used with several disposable parts. The reusable part may comprise components which may be replaced when the components are too worn, become broken or after a predetermined period of time, but much longer than a single treatment. The change of the reusable part may depend on the component wear.

Figure 4:
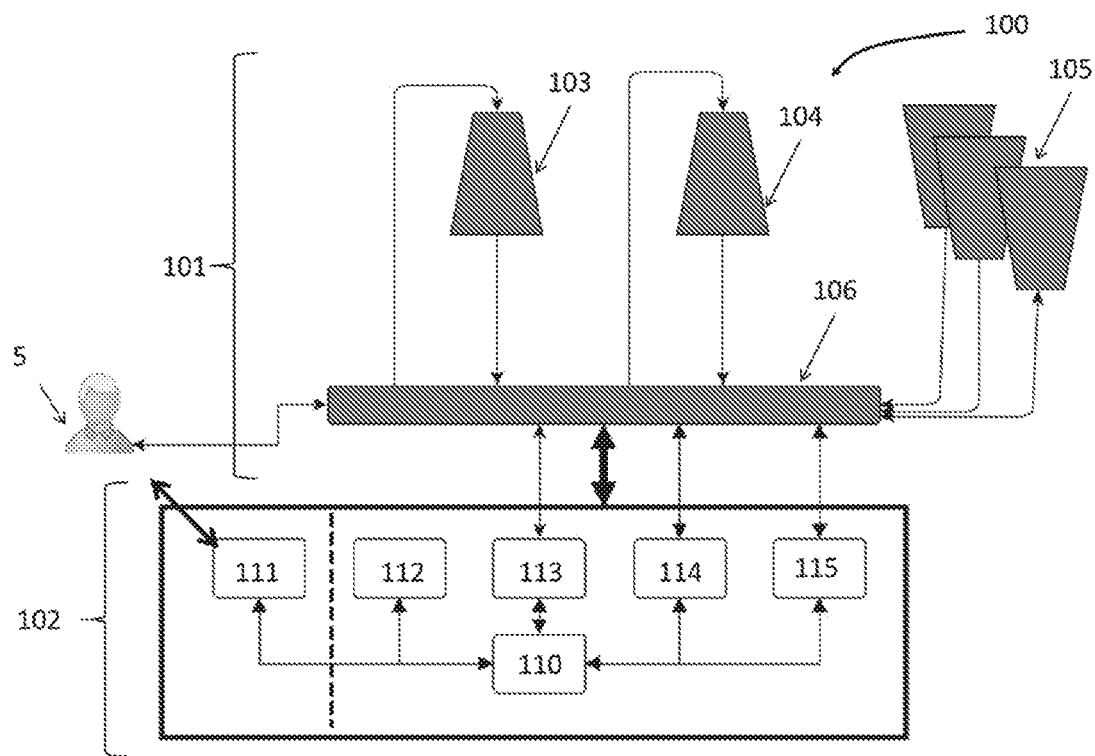

According to the FIG. 4, the overall system 100 may comprise a disposable part 101 and a reusable part 102 (also called apparatus). The disposable part 101 may comprise at least one of a dialyzer 103, a sorbent 104, a bag 105 and a cassette 106. The reusable part 102 may comprise at least one of one or more processors 110, one or more screens 111, other elements 112 connected to the processor such as one or more buttons, one or more sensors 113, one or more actuators 114 and other elements 115 connected to the processor 110 and operatively and removably coupled to the disposable part. The elements (111, 112, 113, 114, 115, 110) may be arranged into the housing of the reusable part. The screen 111 may be touch screen and may be removably coupled to the housing comprising the other elements of the reusable part 102. All or a part of the elements may be connected or coupled to the processor in order to control or monitor the treatment. The processor 110 may execute computer-executable instructions stored in a memory of the system. The sensor 113 may be adapted and intended to be operatively coupled to the disposable part 101.

The active part of the sensor 113 (for example the part which senses) may be located in the reusable part. In this case, the disposable may comprise a coupling element adapted to removably couple the sensor with the disposable part 101. The active part of the sensor (such as probe) may be located/arranged in the disposable part, in this case, the sensor part located into the reusable part may be the connection element allowing the communication between the processor 110 and the active part of the sensor located in the disposable part.

The actuator 114 may be operatively coupled with the disposable part in such a manner that the actuator may act on the disposable part, for example open/close a valve, actuate the pump, . . . .

The element 115 may be a weight scale or a heater controlled by the processor.

Cassette(s)

The system may comprise one or more cassettes which define at least a part of the fluidic pathway of the blood circuit and/or of the dialysate circuit. A cassette is preferentially a part of the disposable part 106 (as shown in the FIG. 4). The system may comprise a single cassette comprising a part of the blood circuit and a part of the dialysate circuit. Preferentially, the system comprises two distinct cassettes: a first cassette dedicated to the blood circuit, adapted and intended to receive blood (and optionally a priming solution, saline solution, pure water solution, dialysate solution or other blood compatible solution) and a second cassette dedicated to the dialysate circuit, adapted and intended to receive a dialysate solution or other compatible solution for the treatment. The FIGS. 2e and 3 show a potential limit 40 of the cassette (blood cassette and dialysate cassette). The pumping device(s) may be a part of the cassette or may be arranged outside of the cassette.

The (blood and/or dialysate) cassette 106 comprises at least one valve adapted and intended to be operatively coupled with an actuator 114 of the reusable part. The (blood and/or dialysate) cassette 106 may comprise at least a part of a pump adapted and intended to be operatively coupled with an actuator 114 of the reusable part.

The cassette 106 comprises a rigid frame 107 adapted to receive a part of the fluid pathway of the circuit (blood or dialysate). As shown by the FIG. 5, the cassette includes a fluid cavity 120 (arranged into the rigid frame for example), one or more port 121 and/or one or more flexible membrane 108 adapted to cover the fluid cavity 120.

The flexible membrane may comprise a coupling area adapted to be operatively coupled with a valve actuator and/or a measurement area adapted to be operatively coupled with a sensor of the reusable part of the system.

The cassette (the blood and/or dialysate cassette) may further comprise a handle 122 adapted to be gripped by the fingers of a user hand.

The membrane may comprise a valve portion adapted to close and open the fluid pathway of the cassette. In this cassette, a lug/head of the valve actuator of the reusable part of the system may push the valve portion against the rigid part (for example the internal wall of the cavity of the rigid frame) in order to close the fluid pathway. The membrane may be formed/molded/structured so as to have a determined shape at the contact portion 124 with the valve seat 123 in order to improve the tightness of the valve. The membrane (in particular the coupling area) may be formed/molded/structured so as to have a determined shape such as a clip element adapted to be removably coupled to a head of a valve actuator (not show).

Figure 5A:
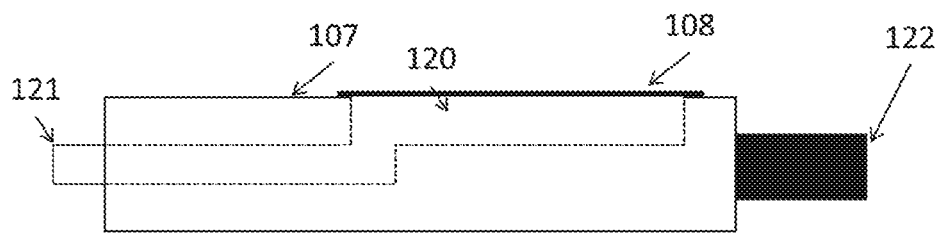
Figure 5B:
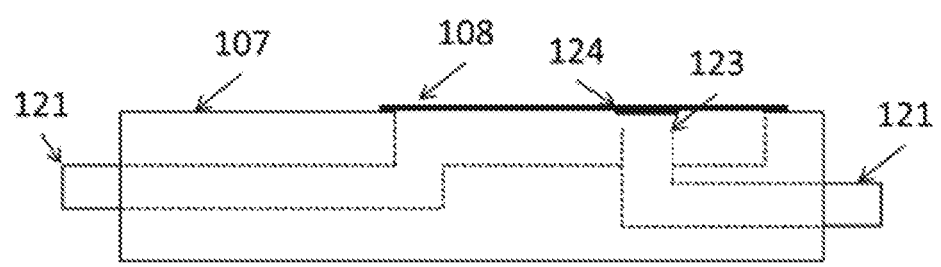
Figure 5B:
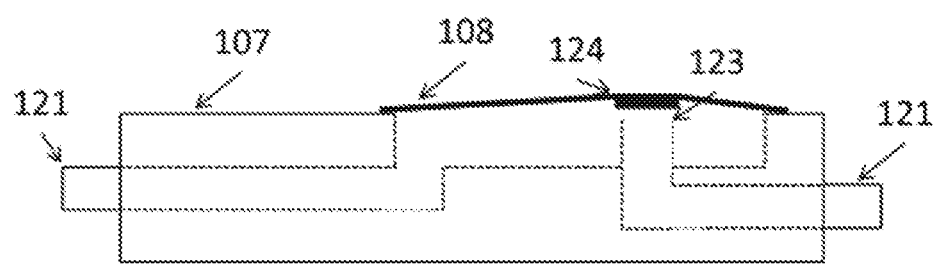

The FIGS. 5b and 5b' show a schematic view (cross section) of the cassette 106 wherein the valve is in an open position. The membrane (in particular the contact 124) is spaced apart from the valve seat 123. In the FIG. 5b, the membrane and the valve seat of the rigid frame are designed in order to have a rest position of the valve which is an open position. In the FIG. 5b', the membrane and the valve seat of the rigid frame are designed in order to have an open position when the membrane is pulled (for example by the valve actuator).

Figure 5C:
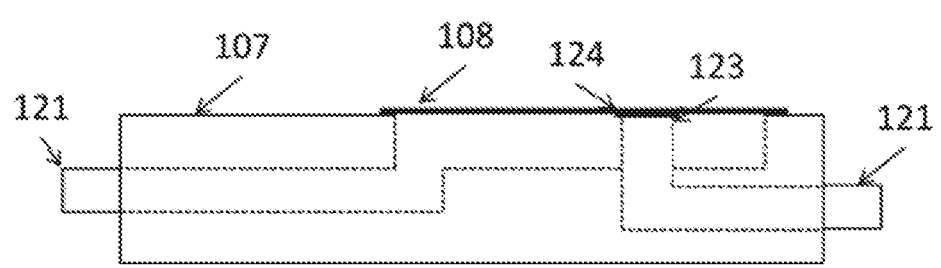
Figure 5C:
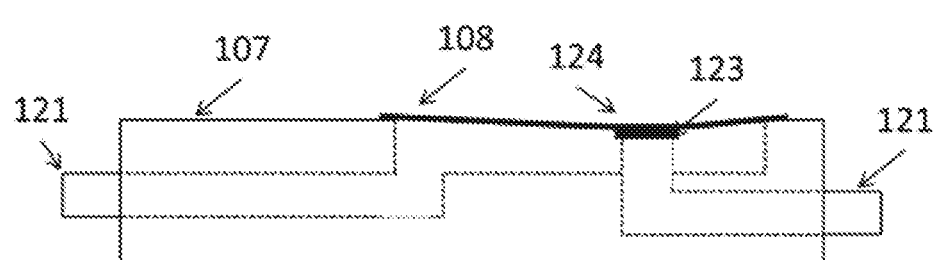

The FIGS. 5c and 5c' show a schematic view (cross section) of the cassette 106 wherein the valve is in a closed position. The membrane is in contact with the valve seat 123. In the FIG. 5c, the membrane and the valve seat of the rigid frame are designed in order to have a rest position of the valve which is a closed position. In the FIG. 5c', the membrane and the valve seat of the rigid frame are designed in order to have a closed position when the membrane is pushed (for example by the valve actuator) against the valve seat 123.

In one embodiment, the cassette may comprise one or more flexible tube secured in the cassette by a frame. In order to limit the hemolysis, the valve actuator may be a pinch valve actuator comprising a lug configured to pinch the flexible tube through the blood cassette.

The (blood and/or dialysate) cassette may comprise a part of the pump. In one embodiment, the pump is a peristaltic pump. In this case, the cassette comprises a flexible tube in fluid communication with a first fluid pathway and a second fluid pathway of the cassette via dedicated ports. The flexible tube is intended to be pressed by at least two roller of the pump against a rigid wall for example a part of the rigid frame of the cassette. The cassette may further comprise a roller assembly including at least two rollers, a roller support device, a coupling device intended to be operatively coupled with a pump actuator of the reusable part of the system.

Figure 6:
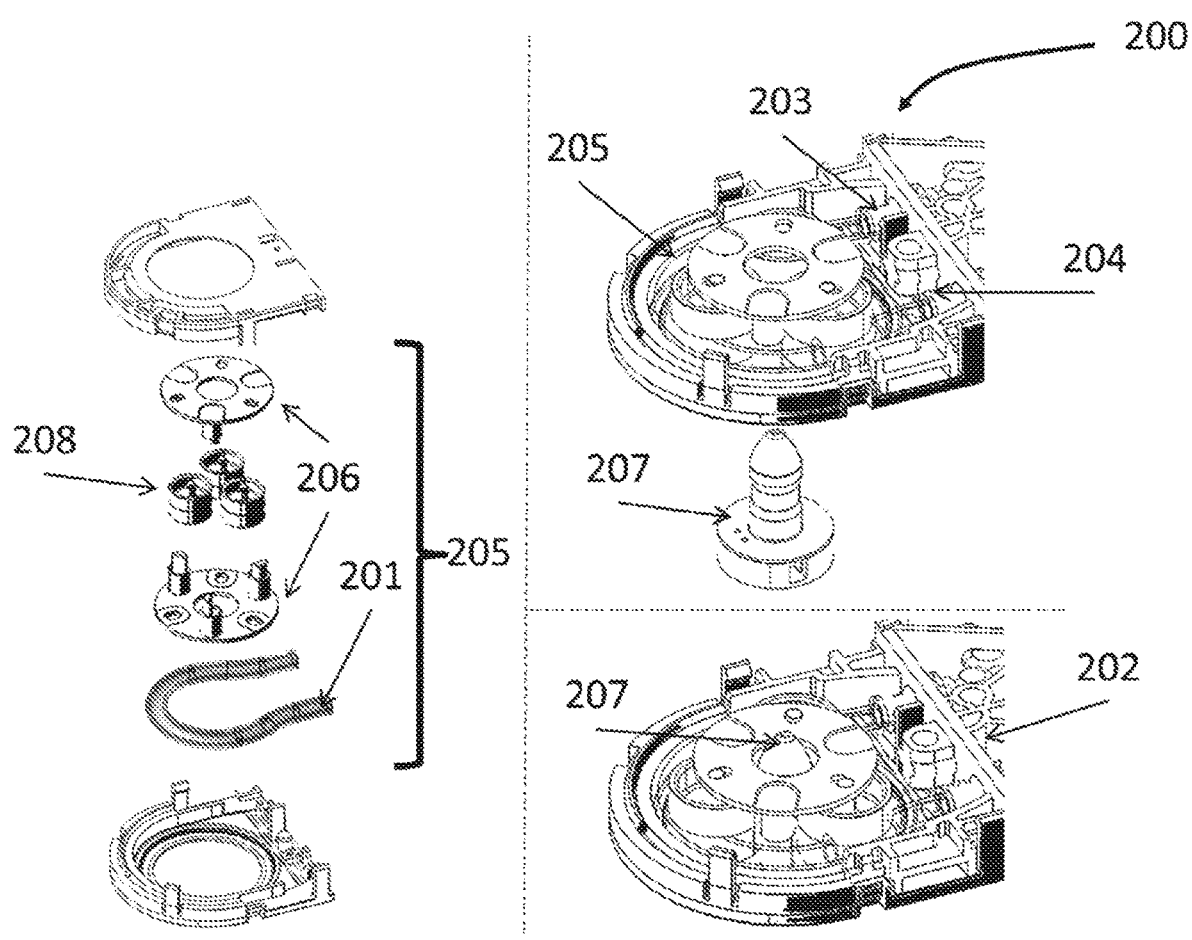

Referring to the FIG. 6, the cassette comprises a flexible tube 201 which is connected to the fluid pathway 202 of the cassette 200, for example via an inlet port 203 and an outlet port 204. A roller assembly 205 is movably (by rotation) disposed into a cavity of the rigid frame of the cassette. The roller assembly 205 comprises at least two rollers 208 maintained by at least one support 206. The FIG. 6 further shows a shaft 207 which is a part of the pump actuator of the reusable part. The shaft 207 is intended to actuate the roller assembly 205. In this embodiment, the roller support 206 comprises a through hole in which the shaft 207 of the pump actuator is intended to be inserted when the cassette is loaded. The roller 208 may be drive by friction and/or may comprise a coupling device (coupled with the roller support 206) such as lug and hole or toothed gear. When the cassette is fully loaded the pump part of the cassette is operatively coupled to the pump actuator of the reusable part.

The roller 208 may be movable relative to its support, for example when the shaft of the pump actuator is inserted into the roller support 206, the external wall of the shaft pushes the roller 208, urging the roller in direction of the peripheral end of the support.

The cassette may be adapted to be inserted into an opening of the reusable part (apparatus) as described thereafter. In order to prevent any finger pinching between the cassette and the opening of the reusable part, the cassette may be adapted to be substantially fitted to the opening (so as to at least partially or fully obstruct or block the opening when a cassette is inserted). The handle and/or the tube(s) (of the cassette) may protrude from the cassette and from the housing of the apparatus when the cassette is fully inserted into the opening. Preferentially, the opening and the cassette are designed in such a manner as to never present any opening having any dimensions larger than 25 mm preferentially larger than 10 mm more preferentially larger than 8 mm or 5.6 mm when the cassette is fully inserted into the opening. For example, the cassette may comprise an edge which substantially obstructs the opening when the cassette is fully inserted into the opening (as described thereafter with the FIGS. 22 and 23). One goal of such design is to avoid the penetration of any patient's finger or object of a similar size into the lodging of the cassette when a cassette is present.

The blood circuit comprises at least two tubes (arteria line and venous line) but preferentially the blood circuit comprises a dedicated cassette and five or six tubes (or more) which extend from the (blood) cassette. A first tube connected to the patient (arterial line), a second tube connected to the patient (venous line), a third tube connected to the blood return bag 19, a fourth (optional) tube connected to the blood return bag 19, a fifth tube connected to the dialyzer 2 (arterial line) and a sixth tube connected to the dialyzer 2 (or drip chamber 9) (venous line).

The dialysate circuit comprises at least two tubes (downstream and upstream of the dialyzer) but preferentially the dialysate circuit comprises a dedicated cassette and at least seven tubes which extend from the (dialysate) cassette: a first tube to the dialyzer 2, a second tube from the dialyzer 2, a third tube to the sorbent device 17, a fourth tube from the sorbent device 17, a fifth tube from the concentrate container 31, a sixth tube to the weighting container 13 and a seventh tube from the weighting container 13. Optional tubes and connection may be: from an initial supply container 28 or priming container 33, from additional supply container 32, from an (in line) heating system . . . .

Other fluid pathway may be arranged into the cassette and at least a part of the fluid pathway comprising a valve may be arranged into the cassette. The FIG. 3 shows the potential limit 40 of the dialysate cassette. The FIG. 2e shows the potential limit 40 of the blood cassette. The shape and/or the size of these limits are just an illustration and are not to be taken in a limiting sense.

Apparatus (Reusable Part)

The apparatus (also called dialysis unit) is a reusable part of the system. The apparatus is designed to be portable by a user; nevertheless this apparatus is not designed to be fixed to the patient. As used in this specification and the appended claims, the term "portable" is generally employed in its sense including "light and small enough to be easily carried or moved" or "possible to take with you if you move to a different place" or "easily carried or conveyed by hand".

Figure 35:
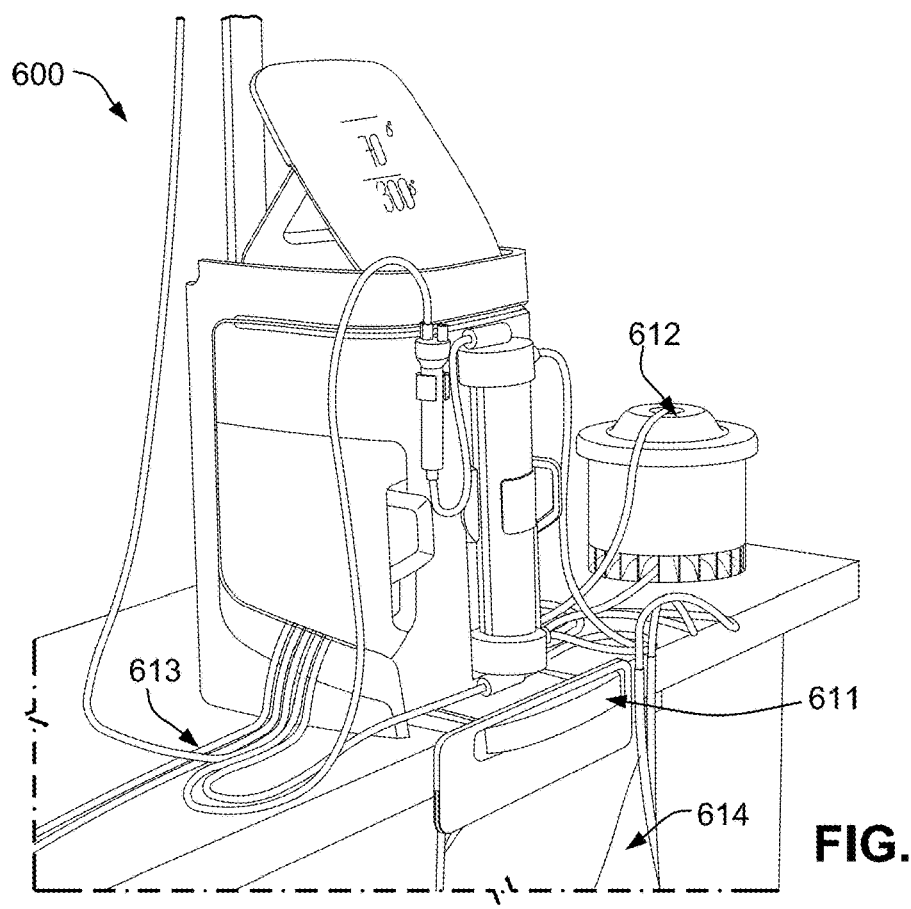
Figure 36:
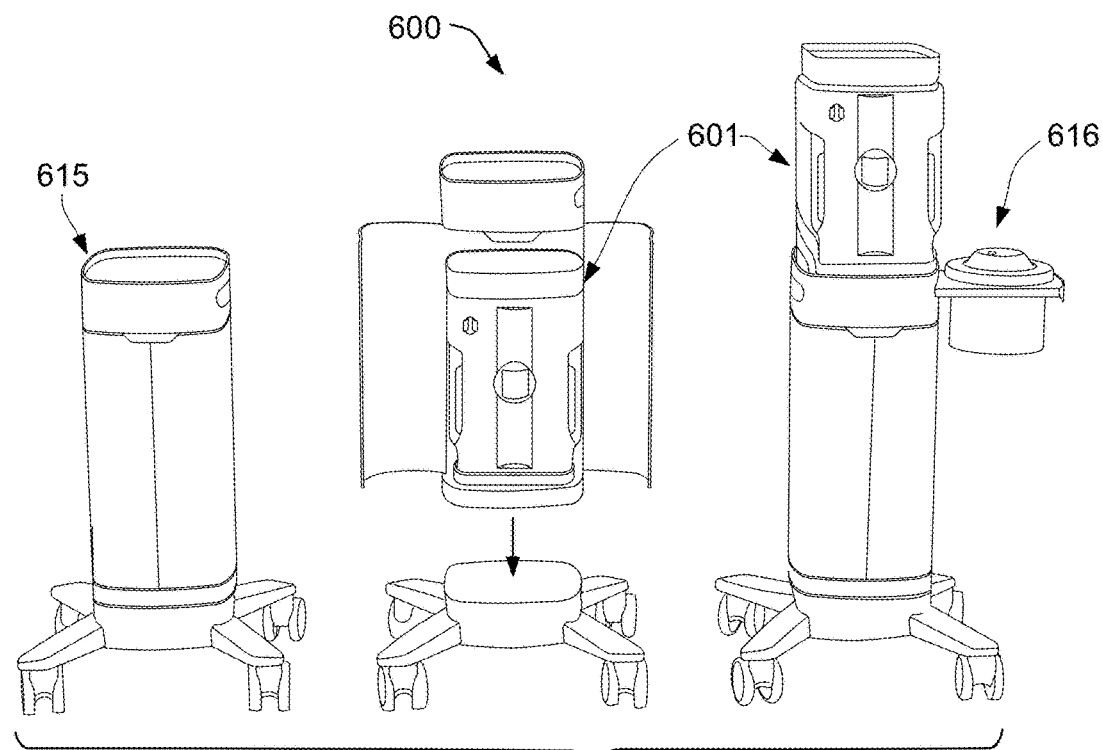
Figure 37:
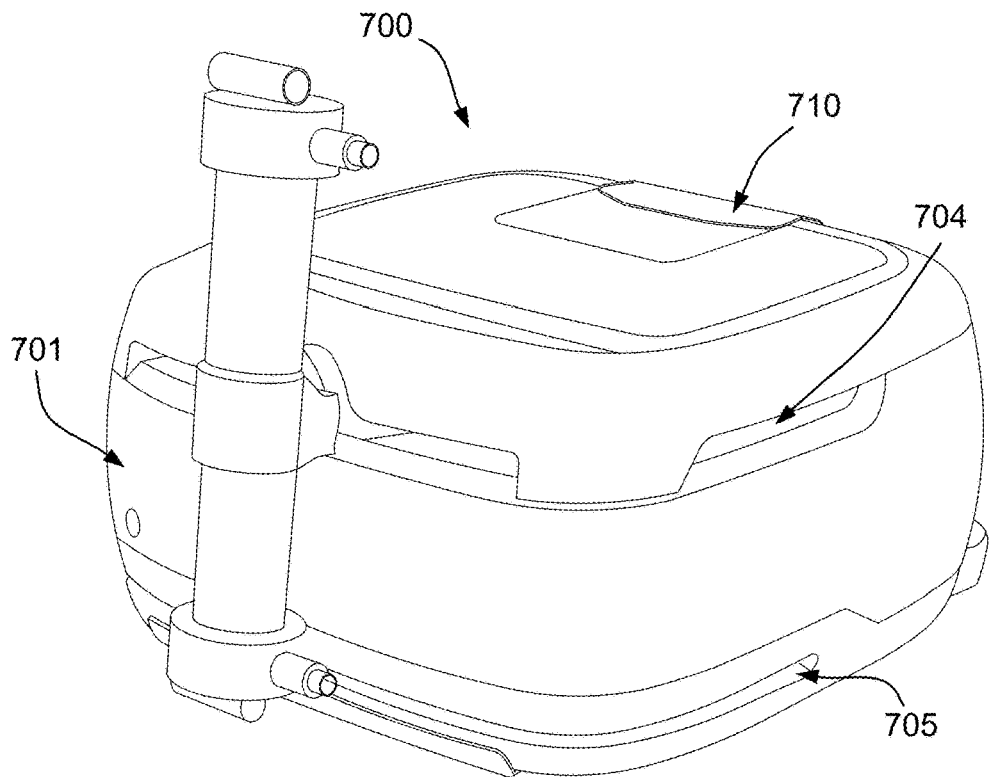
FIGS. 37, 38 and 39 show different views of a potential embodiment 700.
Figure 38:
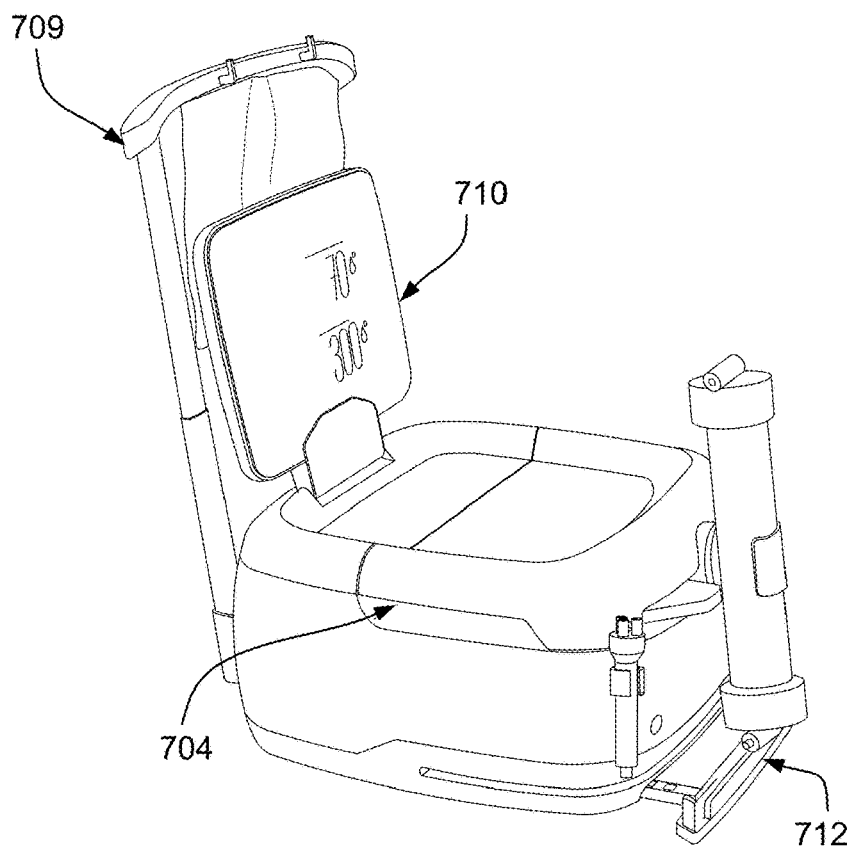
Figure 39:
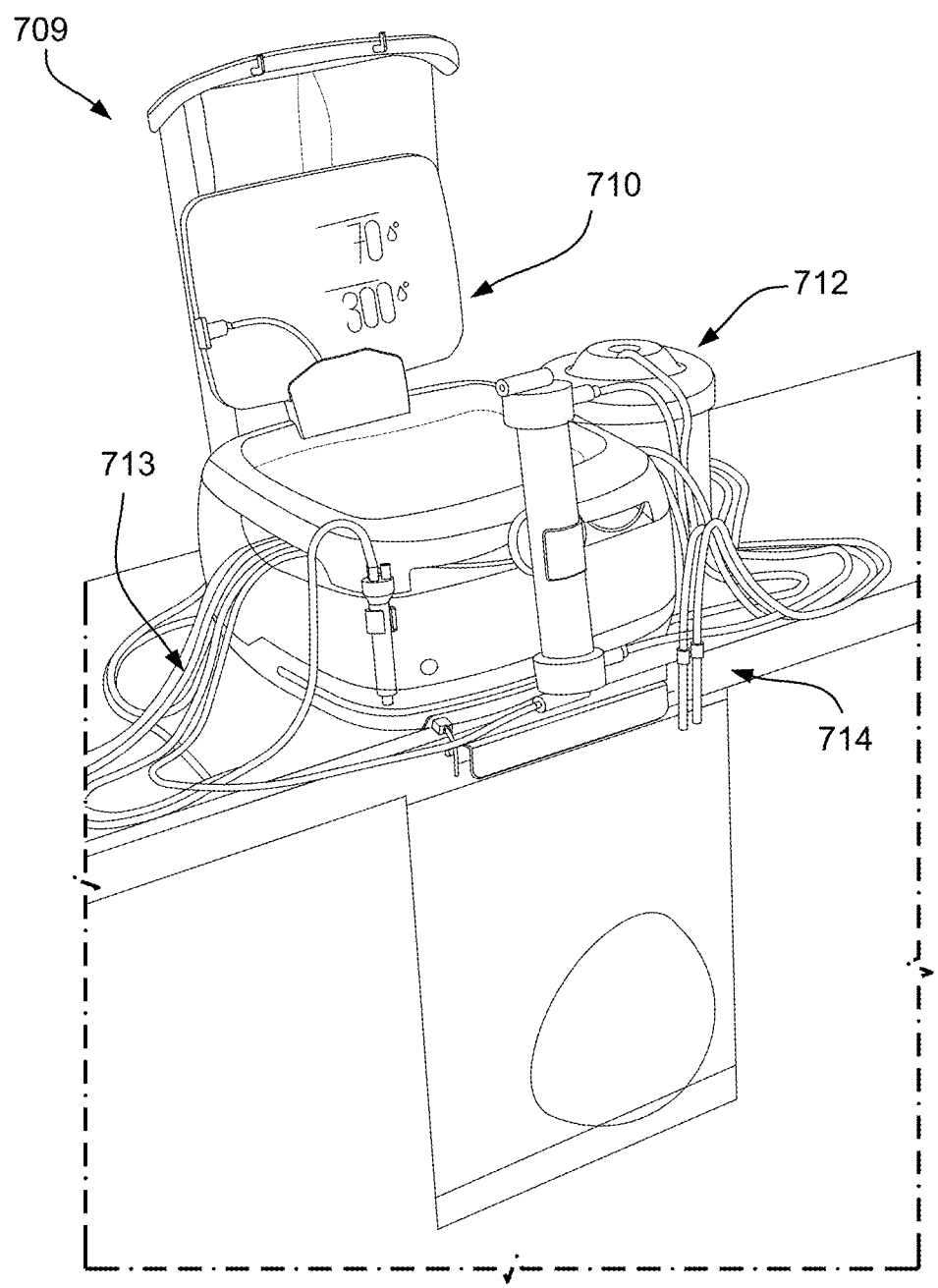

The FIGS. 7 to 12 show a first potential embodiment of the dialysis system, the FIGS. 33 to 36 show a second potential embodiment of the dialysis system and the FIGS. 37 to 39 show a third potential embodiment of the dialysis system. Even if each embodiment has a specific shape, these embodiments may comprise the same or substantially the same assemblies or sub-assemblies (such as pole, container support, scale, sensor, loading system, door device, cassette, support, fluid circuit, container receiver, functional element, electronic device, handle, display device, . . . ) described in this document.

Figure 7:
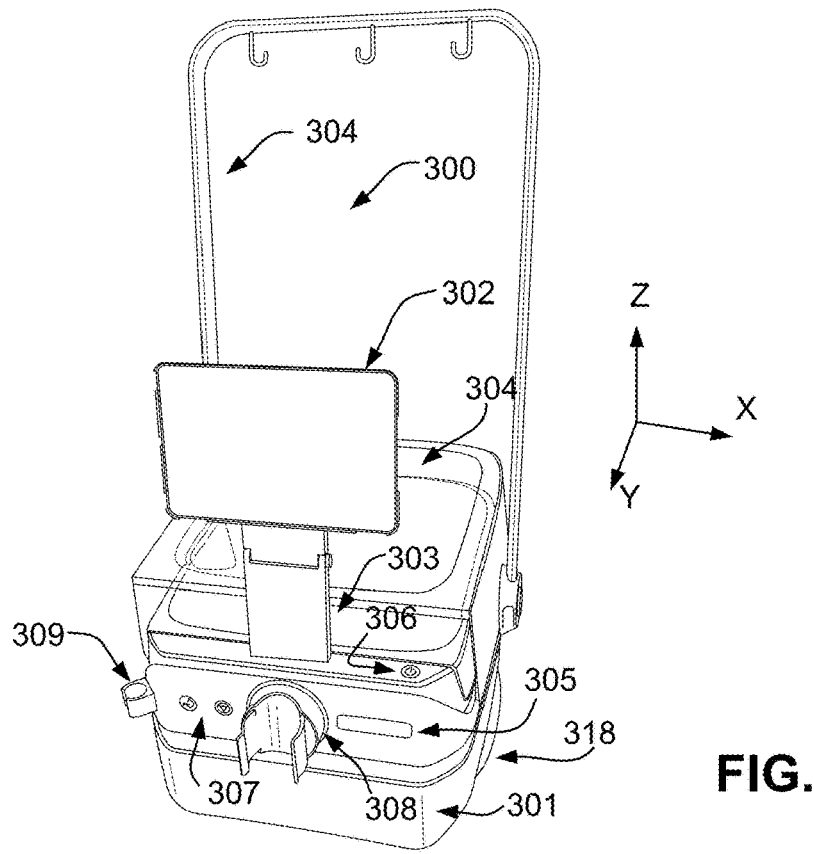
FIG. 7 shows the system in operating configuration without the disposable part.

Referring now to the FIG. 7, the apparatus 300 comprises a housing 301 in which are arranged components for controlling a dialysis treatment. For example: a processor, a valve actuator, a sensor, at last a part of a blood pump adapted to cooperate with the blood line in order to move blood through blood line when the blood line is in fluid communication with a blood source (the patient) and at last a part of a dialysate pump adapted to cooperate with the dialysate pump in order to move dialysate through the dialysate line when the dialysate line is in fluid communication with a dialysate source. The housing 301 have a front panel and side panels.

The housing may have at least one recess 318 (see FIG. 11a) designed to be grasped by the hand of a user, the at least one recess may have a gripping element (for example a shape or a structure which is easy to be grasped by the hand). Preferentially, the apparatus comprises two recesses with gripping element arranged on two opposite side panels of the housing. The recesses may be located at a lower portion of the housing.

Preferentially, the apparatus comprises a display device 302 which may be a movable screen (such as a tablet) removably fixed to the apparatus via a screen support 303. The display device may comprise several screens showing a current status of the treatment, a setting screen, a text and video instruction, patient data, treatment data, . . . . The display device may comprise a processor connected to a memory which comprises a text and video instruction, patient data, treatment data, sound files, video files, . . . . The display device 302 may be removably attached to at least one of a container support 304 (for example a pole 312 (not shown)), the housing 301 and the pole 312. The display device may comprise a display communication unit with a receiver and emitter wirelessly coupled to an apparatus communication unit arranged into the housing 301. Thus, the electronic part arranged into the housing 301 of the apparatus may wirelessly communicate with the display device. A link wire may provide the communication between the apparatus and the display device or use to recharge a battery of the display device. This link wire may comprise an USB connector or other standard connector (for example Apple standard connector). The use of a USB connector or standard connector allows using a standard tablet (I-Pad, Android tablet, . . . ) as display device. Thus, in case of failure of the original display device, the user can change with a standard tablet.

The display device 302 may be used as an electronic health booklet for the treatment. The patient brings to the doctor his display device and the doctor may monitor the treatment history and other health data of the patient. The doctor may change the treatment parameters via the display device. Furthermore the doctor may download the treatment parameters or other data from his computer (PC or other computing device of the doctor) to the display device wirelessly or via a wire connection (for example an USB connection). Furthermore, the display device may comprise an application or computer-executable instructions adapted to download data from and/or upload data to the doctor's computer and an internal memory configured to record the treatment history, the patient data (weight, blood pressure, alarm, UF, executed treatment, . . . ), the new treatment parameter, . . . .

The apparatus may comprise a standard connection port (for example USB port) connected to the electrical supply management device of the apparatus and/or connected to a processor of the apparatus, and the display device may comprise a standard connection port (for example USB port) connected to the electrical supply management device of the display device (connected to the battery of the display device) and/or connected to a processor of the display device.

The apparatus may further comprise an additional screen 305, a power button 306 or an emergency button 307. The additional screen 305 is designed to bring information to the user in a concise manner.

The display device provides more detail (videos, instructions, advises, . . . ) than the additional screen (alarms, failures, current treatment, progress bar, . . . ). The power button 306 may be designed to turn on or off the apparatus or to turn off all or a part of apparatus lights. The emergency button 307 may be designed to be activated during the treatment for example to command a premature end of treatment (for example to launch the blood return process before the end of the treatment). These buttons and screen are preferentially connected (via a wire connection) to the processor of the apparatus. In one embodiment, similar buttons may be arranged on and may be enable via the display device (via the touch screen for example).

The apparatus may comprise a dialyzer support 308 (configured and intended to removably secure the dialyzer) and a drip chamber support 309 (configured and intended to removably secure the drip chamber) which may be arranged on the front panel of the housing 301, on a lateral panel of the housing 301 or on a container support 304 (for example fixed to the pole).

Figure 8:
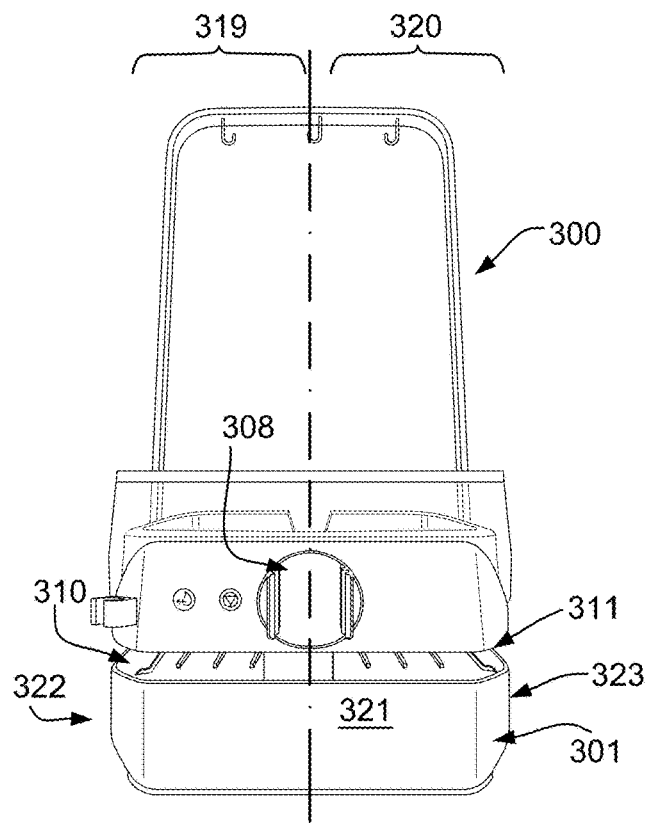
FIG. 8 shows the system in operating configuration without the disposable part.
Figure 33:
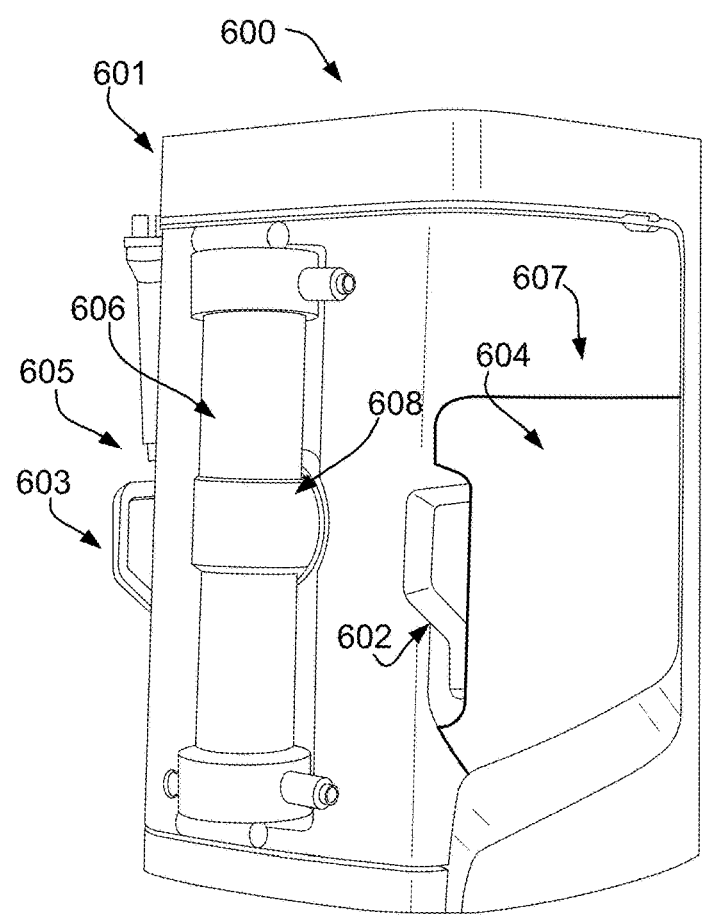
FIGS. 33, 34, 35 and 36 show different views of a potential embodiment 600.

Preferentially the housing comprises at least one opening (slot or groove) adapted to allow inserting one or two cassettes of the disposable part into the apparatus. The FIG. 7 shows a single opening and the FIG. 8 shows two distinct openings. The opening may be substantially horizontally (or vertically or inclined) extended on the front panel and/or a lateral panel of the housing 301. The FIG. 33 shows two vertical (and preferentially lateral) openings closed by vertical doors (such sliding door, retractable door, revolving door or swing door). The FIG. 37 shows horizontal opening(s) closed by door(s) (a single door or two doors) (such sliding door, retractable door, revolving door or swing door) which may be adapted or configured to be used as a container receiver.

In case where the disposable part comprises two distinct cassettes, a single opening may be adapted for both cassettes or two openings may be arranged through the housing. In case where the apparatus comprises two distinct openings for inserting the cassettes through the housing, a first opening may be arranged in a first portion of the housing and the second opening may be arranged in a second portion (which may be opposite to the first portion).

For example, the FIG. 8 shows a housing 301 with a first opening 310 and a second opening 311. The first opening is horizontally extended through a first portion 319 of the housing 301. For example, the first opening 310 is horizontally extended from a part of the front panel 321 to a part of the side panel 322 of the first portion 319. The second opening 311 is horizontally extended through the second portion 320 of the housing 301. For example, the second opening 311 is horizontally extended from a part of the front panel 321 to a part of the side panel 323 of the second portion 320.

Between the both openings, the apparatus may comprise a rigid structure adapted to support the weight of the elements arranged above the openings so as not to deform the general structure of the apparatus.

The first opening 310 may be dedicated to the blood cassette and the second opening may be dedicated to the dialysate cassette. The FIG. 8 shows a first opening smaller than the second opening. The apparatus and/or the cassette may further comprise a mechanical coding in order to prevent the insertion of a cassette in a non-dedicated opening. Thus, the user cannot insert a blood cassette in the second opening and/or a dialysate cassette in the first opening. Preferentially the dialyzer support 308 is arranged between both openings and the drip chamber support at the first portion 319. The dialyzer support is configured in order not to obstruct any opening when the dialyzer is secured on its support, such that the cassette may be loaded to or unloaded from the apparatus.

The first portion may be called the blood side of the apparatus because this side receives the opening dedicated the blood cassette. The second portion may be called the dialysate side of the apparatus because this side receives the opening dedicated the dialysate cassette.

Figure 9:
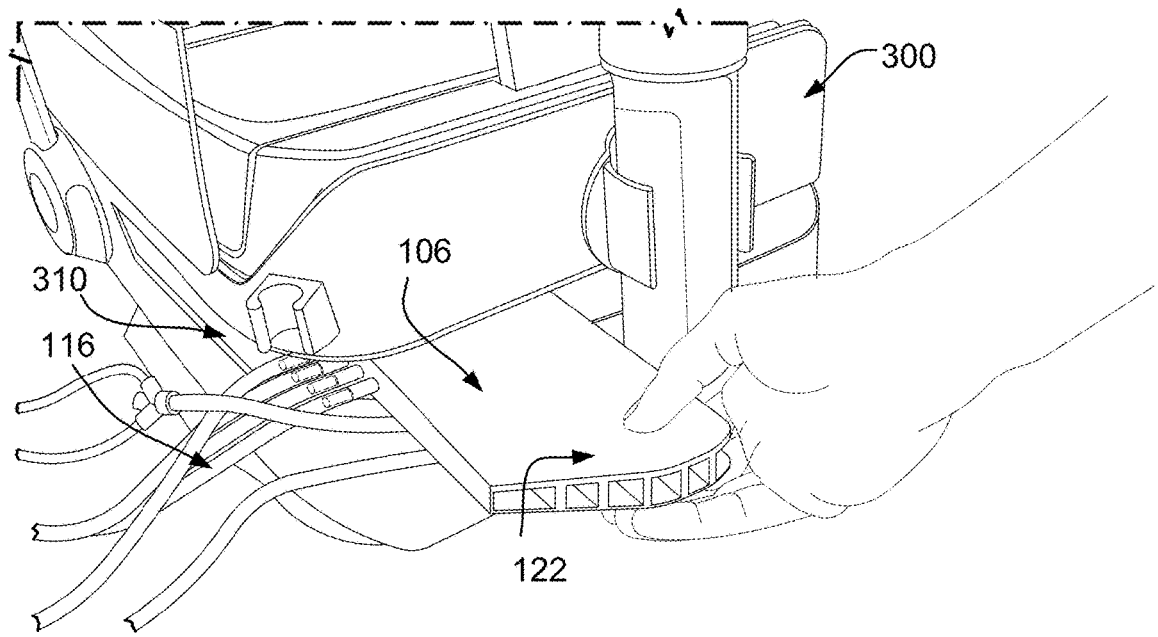
FIG. 9 shows the insertion of a blood cassette into a dedicated opening of the system.

Referring now to the FIG. 9, the user inserts a blood cassette through the first opening. In this embodiment, the blood cassette comprises a handle 122 by which the user grasps the blood cassette. The blood cassette is engaged and slid into the apparatus according to an axe defined by the apparatus 300 (Y or X axes). The cassette 106 further comprises at least one tube 116 which extends from a side of the cassette (preferentially a side which is perpendicular to the side comprising the handle or other side than the side of the handle or same side than the handle). At least one opening is adapted to allow the passage of the tube outside the apparatus through the opening of the side panel of the first portion (for example). To insert the blood cassette, the user manipulates the blood cassette by the handle, enters the cassette through the opening (for example of the front panel or of the side panel) and slides the cassette until the end of the path. At the end of the path, a sensor is adapted to detect the presence of the inserted cassette. This sensor sends (to the processor) data in order to inform the processor that the cassette is inserted.

Figure 10:
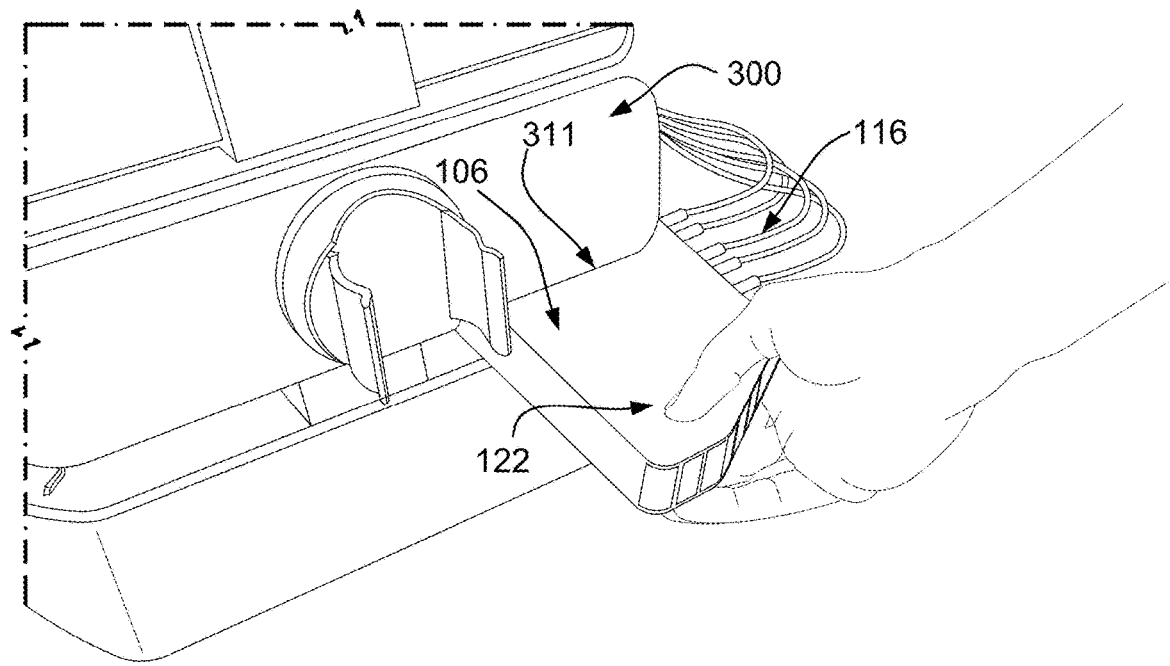
FIG. 10 shows the insertion of a dialysate cassette into a dedicated opening of the system.

Referring now to the FIG. 10, the user inserts a dialysate cassette through the second opening. In this embodiment, the dialysate cassette comprises a handle 122 by which the user grasps the dialysate cassette. The dialysate cassette is engaged and slid into the apparatus 300 according to an axe defined by the apparatus (Y or X axes). Said insertion axe of the dialysate may be the same of or opposite to the insertion axe of the blood cassette. The cassette 106 further comprises at least one tube 116 which extends from a side of the cassette (preferentially a side which is perpendicular to the side comprising the handle or other side than the side of the handle or same side than the handle). At least one opening is adapted to allow passage of the tube outside the apparatus 300 through the opening of the side panel of the second portion (for example). To insert the dialysate cassette, the user manipulates the dialysate cassette by the handle, enters the cassette 106 through the opening (for example of the front panel or of the side panel) and slides the cassette until the end of the path. At the end of the path, a sensor is arranged adapted to detect the presence of the cassette 106. This sensor sends to the processor the data in order to inform the processor that the cassette is inserted.

When the cassette is inserted a loading system may be automatically activated/launched. During the treatment, the opening may be closed by a door and/or a lock mechanism may bloc the cassette in an operating position. One or both may be activated by the loading system or at the start of the treatment. The lock mechanism may be a rod inserted through a hole arranged into the cassette during the loading process (for example by the loading system).

Figure 22:
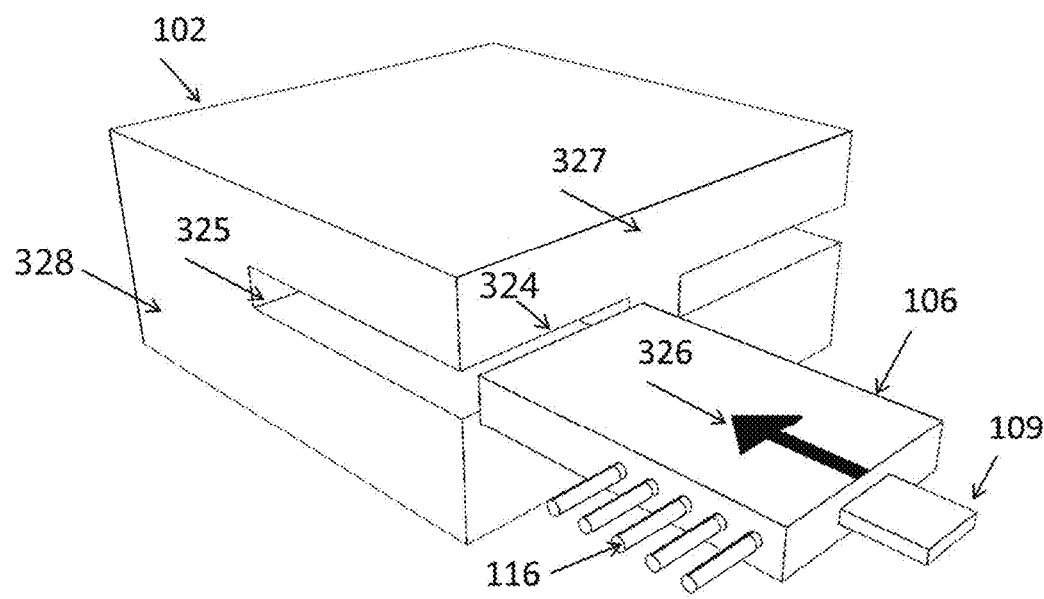
FIGS. 22, 23a to 23c, 24, 25 and 26 show several embodiments of openings and cassettes according to the invention.
Figure 23A:
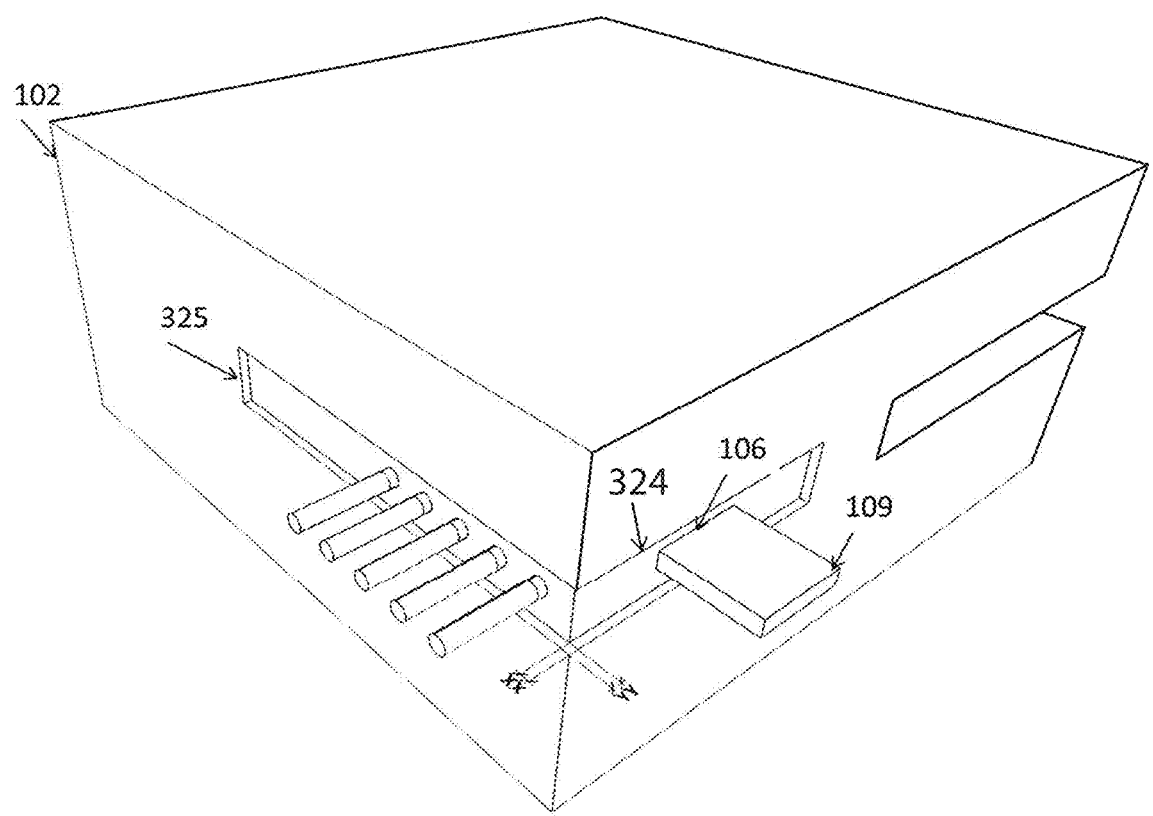
Figure 23B:
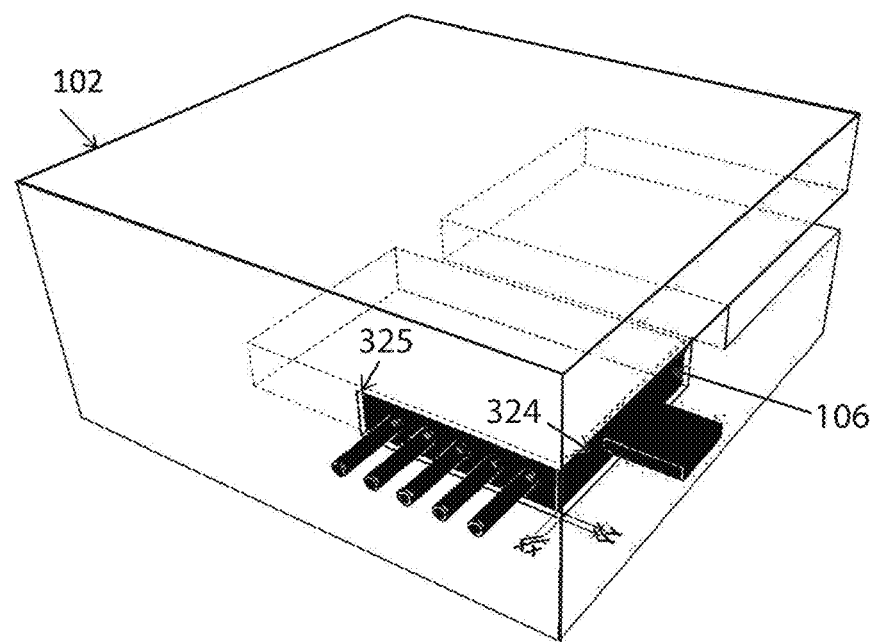
Figure 23C:
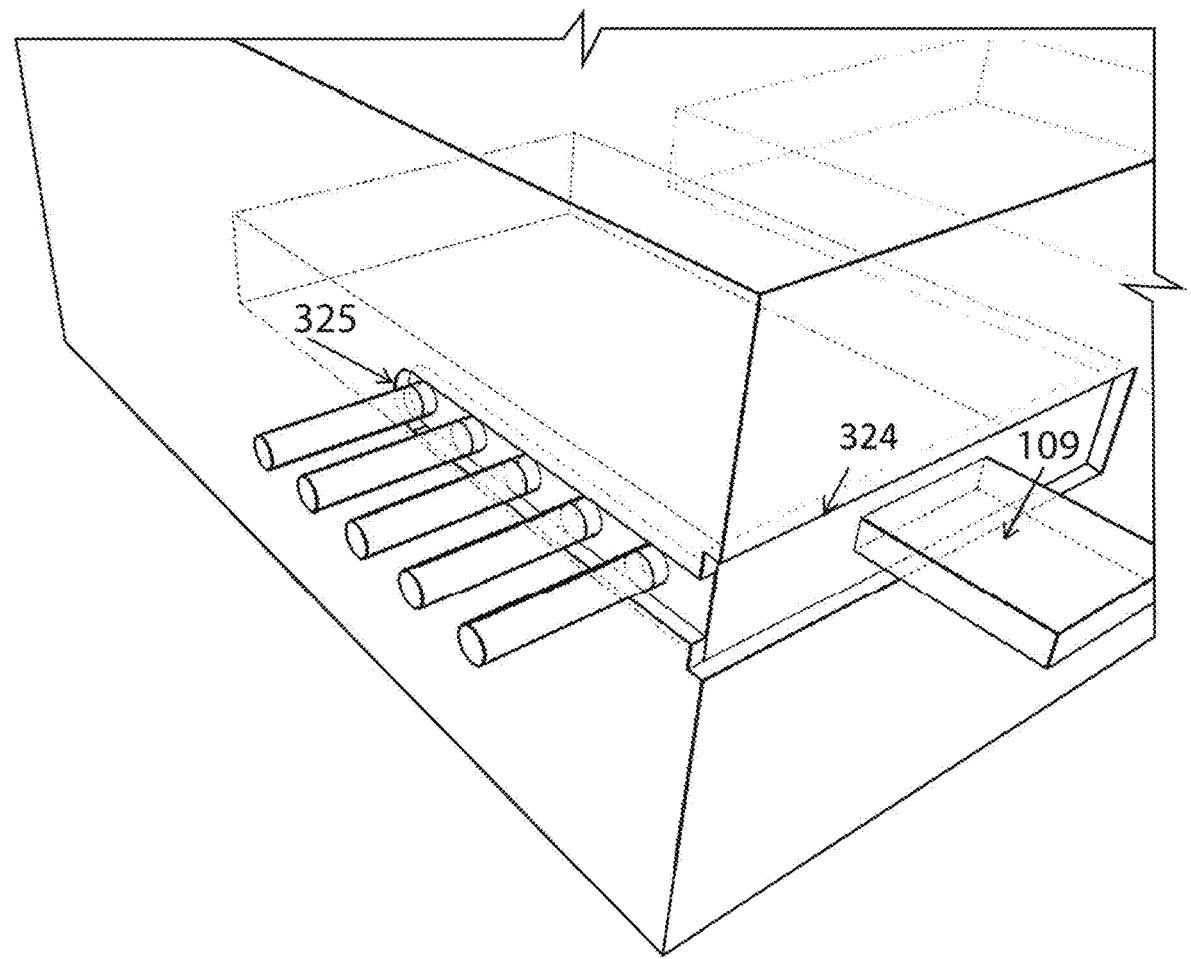

Referring now to the FIGS. 22 and 23, a cassette 106 comprises tubes 116 and an optional handle 109. The apparatus 102 comprises an opening 324 arranged on a first side 327 of the housing and an additional opening arranged on a second side 328 of the housing. Preferentially, the first side 327 is substantially perpendicular to the second side 328. The opening 324 and the additional opening 325 provide an access to a cassette holder (at least for inserting or removing the cassette). The opening 324 and the additional opening 325 provide a continuous aperture so that a part of the apparatus is cantilevered above the cassette compartment. The opening 324 and the additional opening 325 define a horizontal, inclined or vertical plan (in respect of the apparatus) in which the cassette will be inserted during at least a part of the loading process or during the treatment.

The opening 324 is adapted to allow inserting and removing the cassette, thus the opening 324 may be larger than at least the side of cassette by which the cassette is inserted. At least during the insertion phase or withdrawn phase (of the cassette), guiding elements (of the cassette holder, for example tracks) are aligned with the opening(s) and arranged along with the plan defined by the openings.

The additional opening 325 is adapted to allow at least one element to protrude from the housing, for example the tubes, handle, . . . . The additional opening 325 may be smaller than the side of the cassette by which the elements protrude. For example, the opening 324 (shown at the FIGS. 23a, b and c) has substantially the same size than the side of the cassette which comprises the handling element 109 while the additional opening (the side opening) 325 (as shown in the FIG. 23c) is shorter than the corresponding side of the cassette. The dashed line shows the limits of the cassette in the apparatus.

The FIGS. 23a and b show the references "XX" and "YY", these references illustrate the recess formed by the cassette and the housing of the apparatus when the cassette is fully inserted. The size of XX and/or YY may be as small as possible (for example depending on the manufacturing tolerances) in order to provide an area substantially plane of at least one side (comprising the opening) of the apparatus when the cassette is fully inserted.

Figure 24:
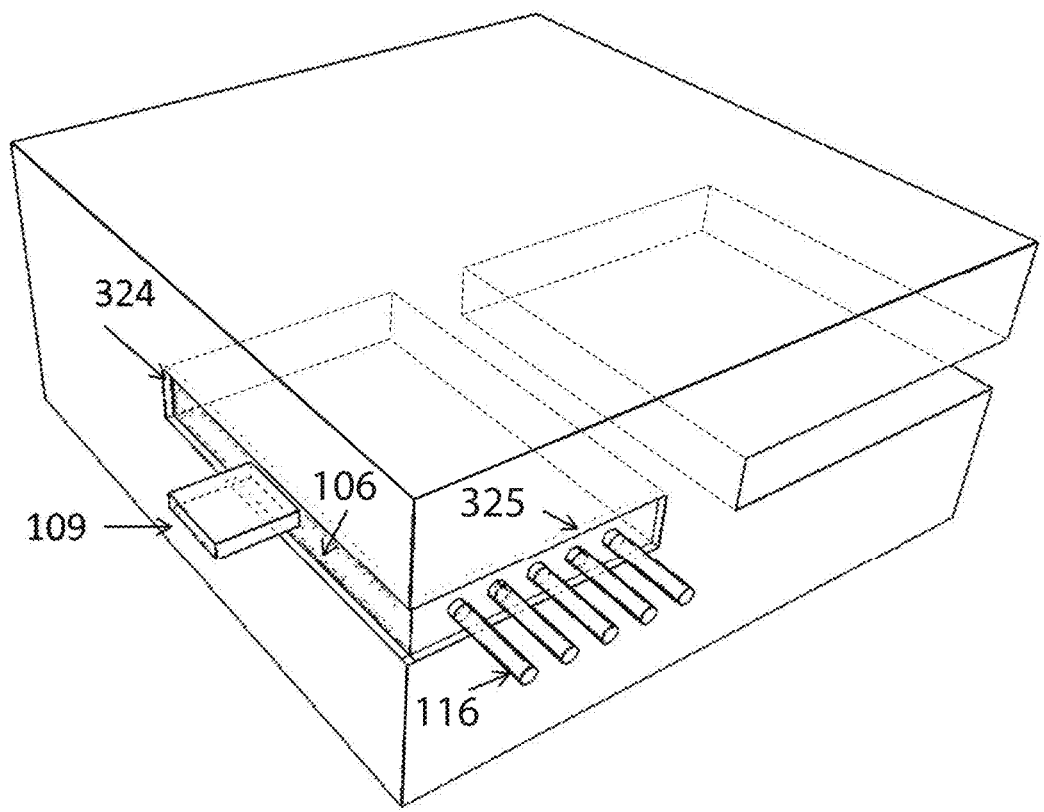
Figure 25:
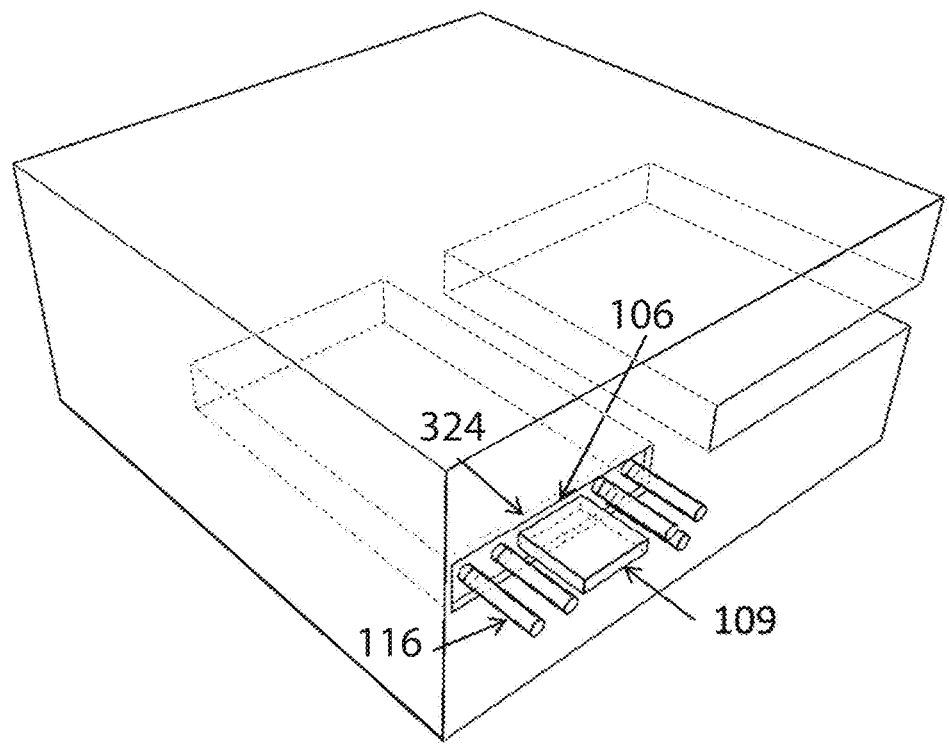
Figure 26:
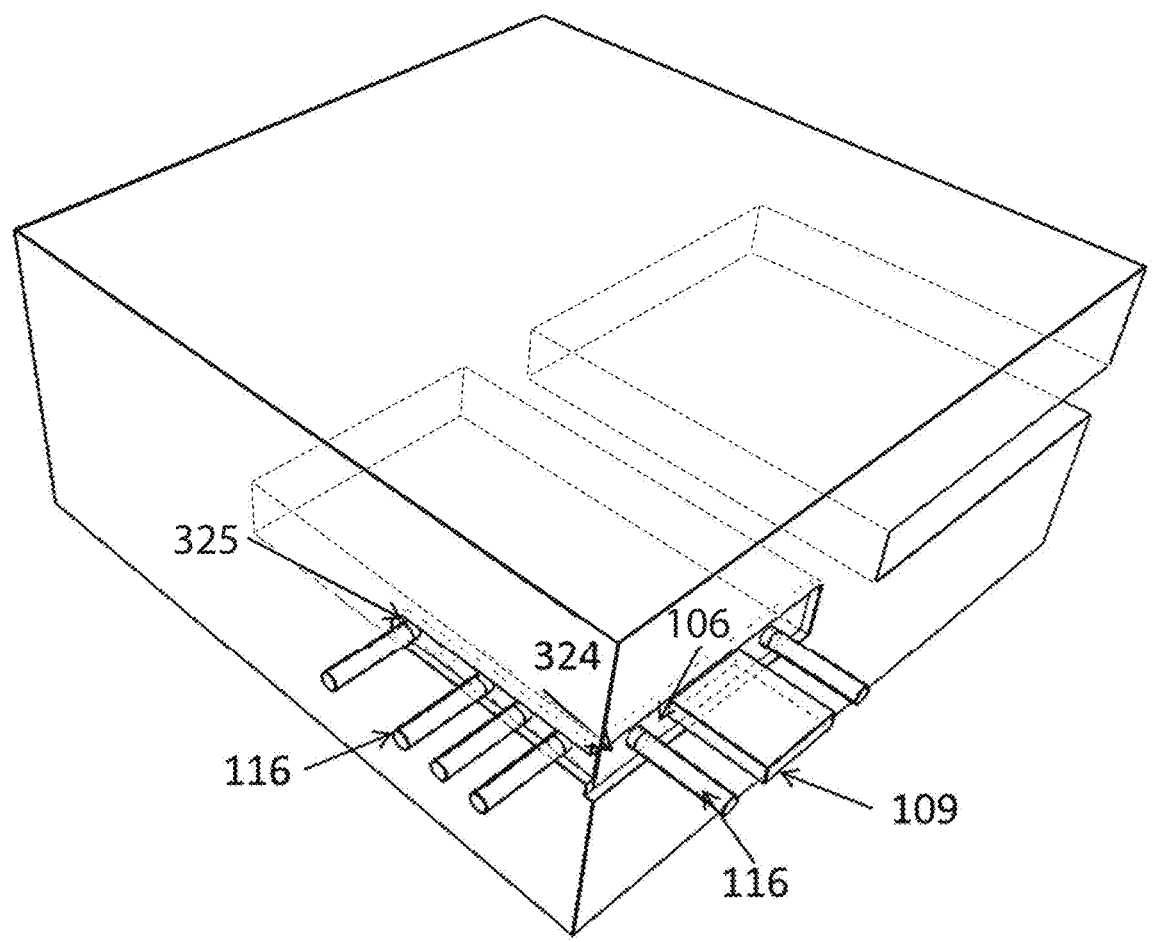
Figure 27:
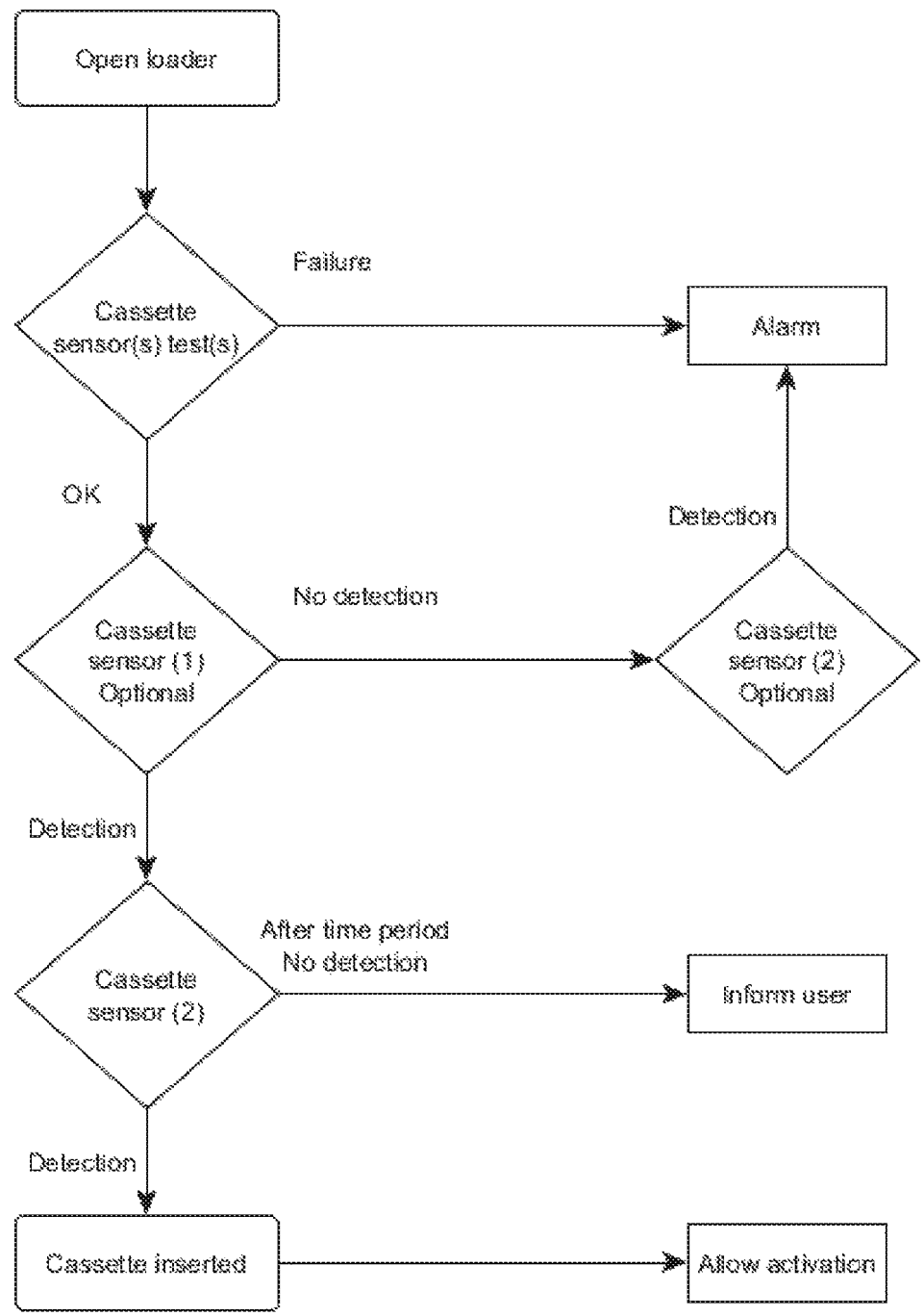
FIG. 27 shows a flowchart of cassette detection process.
Figure 28:
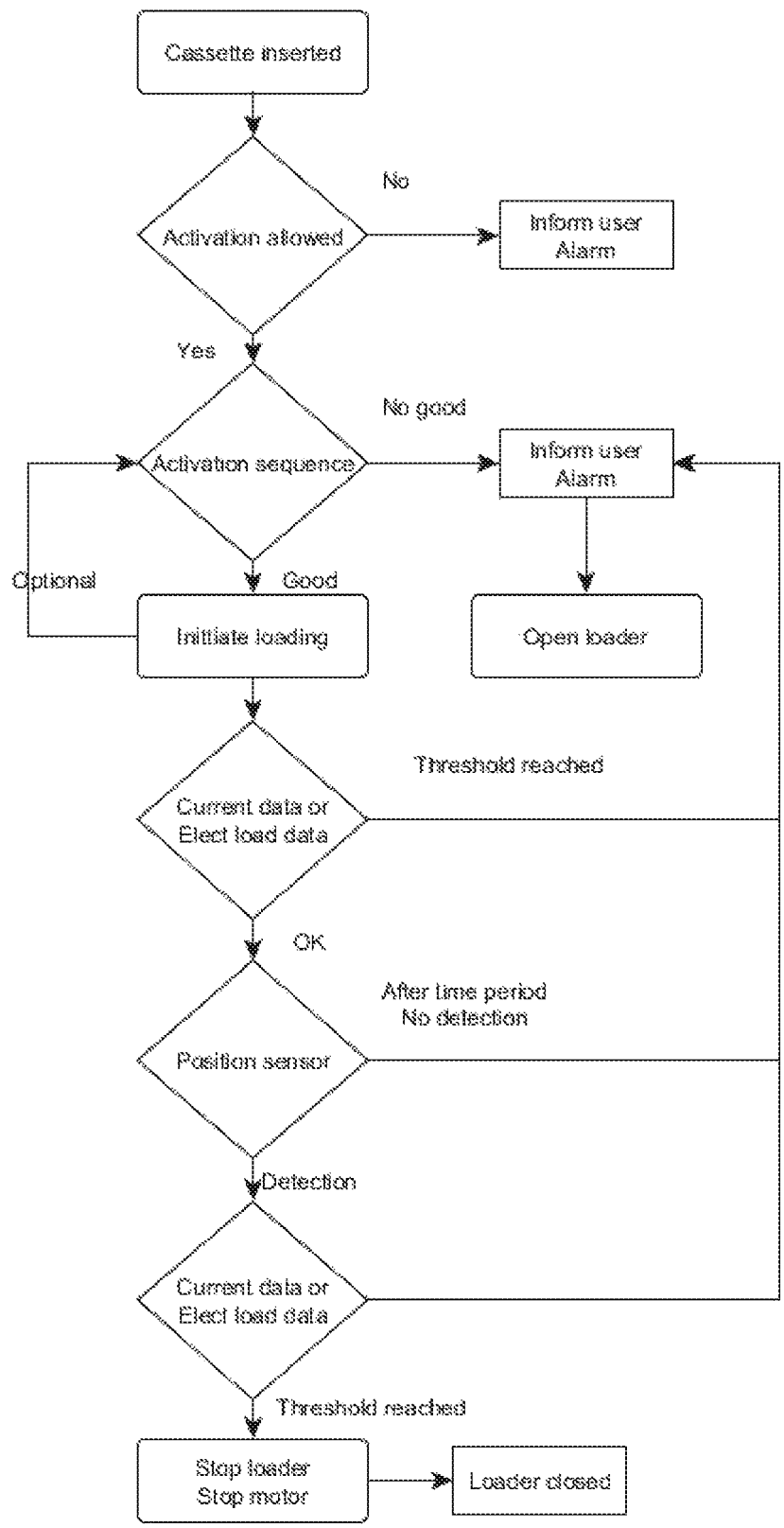
FIG. 28 shows a flowchart of loader position detection process.
Figure 29:
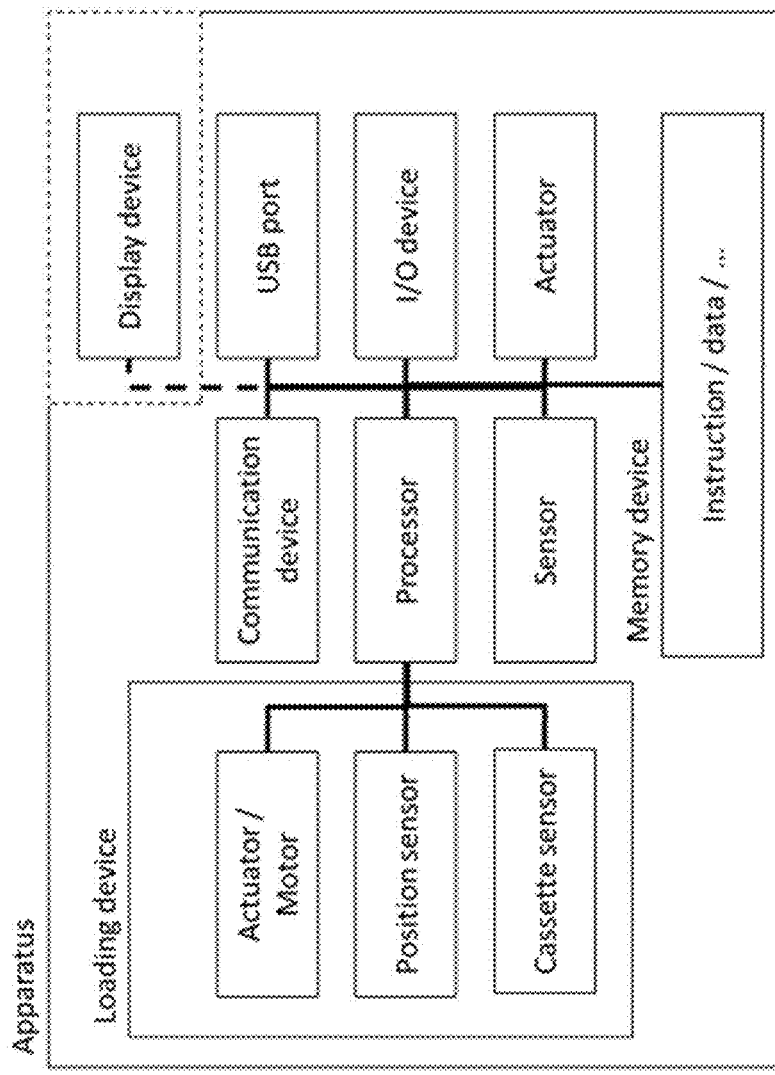
FIG. 29 shows a schematic view of an electronic device of the apparatus.

Other possible designs are shown by the FIGS. 24, 25 and 26. The FIG. 25 shows a single opening 324 (no opening 325) for the cassette and a cassette comprising tubes and optionally a handle arranged on the same side. In another embodiment, a part of the tubes are arranged on the same side of the handle and another part of the tubes are arranged on an other side of the cassette as disclosed at the FIG. 26.

All features illustrated through the FIGS. 22, 23, 24, 25 and 26 may be implemented to the blood cassette and/or the dialysate cassette and there dedicated opening(s) of the apparatus.

The apparatus may comprise container support 304 (such as a pole or a receiver) (for example as shown by the FIG. 7) intended to receive one or more container (such as bag, syringe, . . . ) during the treatment. The containers may be a part of the disposable part and the container support 304 may be a part of the reusable part. At least one container stored at least one of dialysate solution, saline solution, concentrate solution and other solution (heparin, calcium, pure water, . . . ).

As described above, the apparatus may comprise a container support 304 which is intended to receive or hold a solution bag during the treatment. The container support may be adapted to have a first position and a second position (and an optional third position). The first position is required during treatment and the second position may be required during the transport of the apparatus or when the apparatus is stored or when the apparatus does not perform any treatment. The second position allows having a compact apparatus with optimized size.

Figure 11A:
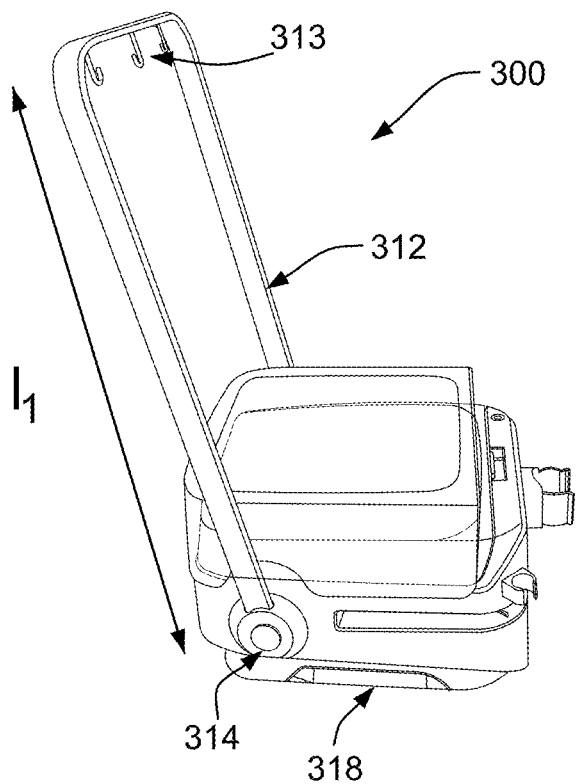
FIGS. 11a to 12c show the apparatus in a first configuration (required for the treatment), a second configuration (enabling saving space) and a third configuration (optional 12b) (enabling the preparation of the treatment for example to access the container receiver)
Figure 11B:
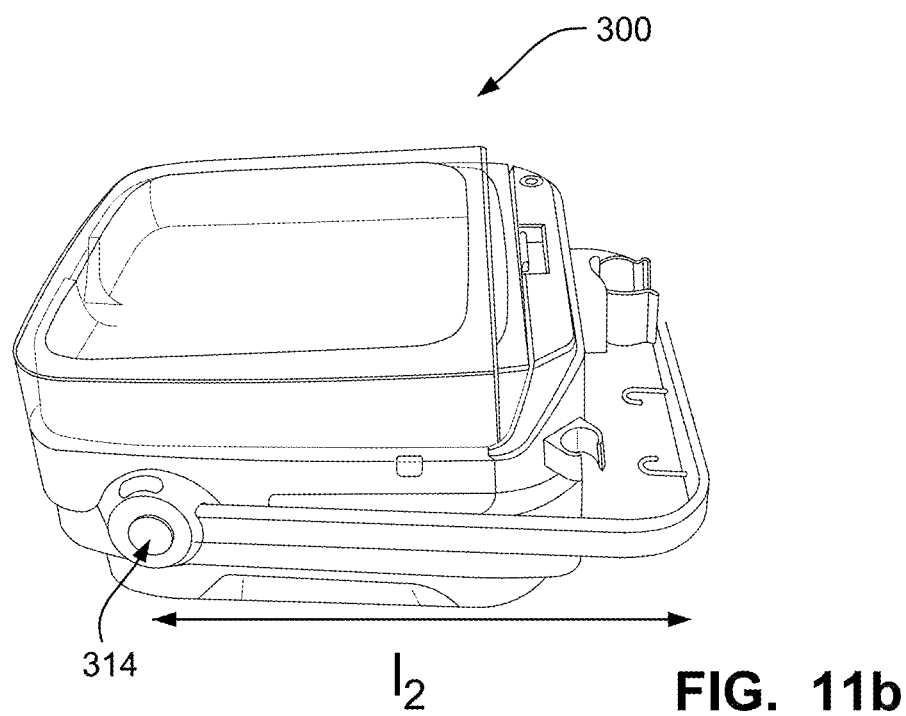

Referring to the FIGS. 11a and 11b, the apparatus 300 comprises a pole 312 adapted to hold at least one solution bag (for example: dialysate, concentrate, saline, empty bag, UF bag, drain bag, . . . ). The solution bag may be removably fixed to the pole 312 via one or more hook 313. The pole 312 comprises a first position allowing supporting the bag during treatment. The pole 312 may be telescopic in such a manner that the length (h) of the pole 312 (when is placed in the first position) may be greater than the length (12) of the pole 312 (when is placed in the second position). When the pole 312 is placed in a second position, the user may move the apparatus 300 by taking by the hand the pole 312 as a handle. The pole 312 may comprise a rotating fixing element 314 adapted to fix the pole to housing of the apparatus and to move the pole from a first position to a second position and/or vice versa. A lock device (not shown) may be adapted in order to block the pole in a predefined position. Preferentially the container 19, 28, 32 and/or 33 (for example shown by the FIG. 3, 20 or 21) is/are removably fixed to the pole 312 in preparation, priming and/or treatment configuration. The pole may comprise an electronic scale.

Figure 12A:
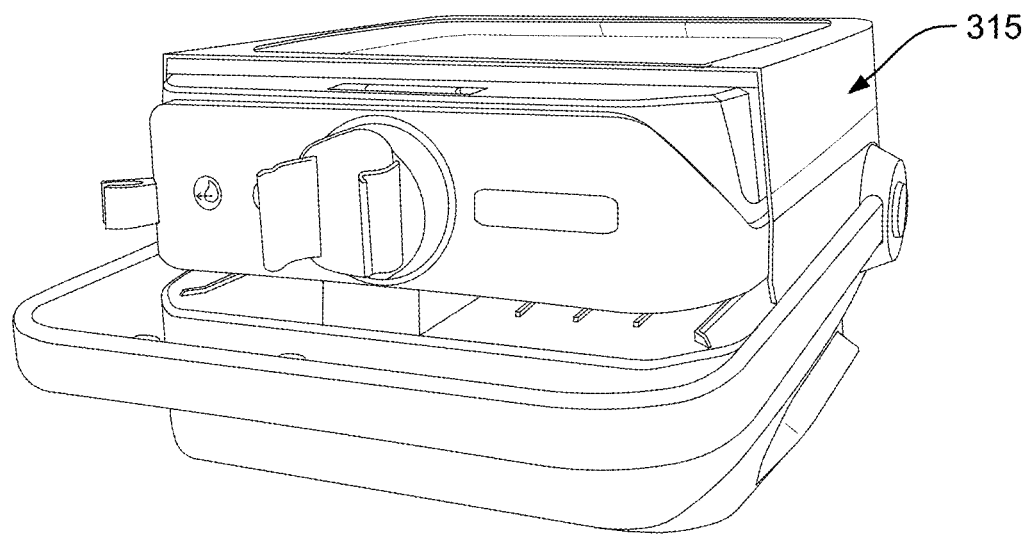

Referring to the FIGS. 12a, b and c, the apparatus may comprise a movable container support 315 adapted to receive a solution bag (for example: dialysate, concentrate, saline, empty bag, UF bag, drain bag, . . . ). The movable container support may comprise a receiver part having a concave shape designed to receive and to store at least one solution bag during the treatment. The apparatus 300 may comprise a fixing element 317 adapted to removably secure or to removably position or remobaly lay on the movable container support to/against the housing 301. The movable container support 315 comprises three positions, a first position required during treatment, a second position which may be required during the transport of the apparatus or when the apparatus is stored or when the apparatus does not perform any treatment and a third position providing an access to a container receiver 316 arranged below. The fixing element 317 may be a protrusion. The protrusion may comprise a protruded position allowing placing the movable container support in a first position and a retracted position allowing placing the movable container support in a second position.

The FIG. 12a shows the movable container support 315 in a second position. The movable container support is designed to optimize the size. The shape of the movable container support 315 and the shape of the container receiver 316 are designed in such a manner that the container receiver 316 may receive at least a part of the movable container support, for example the receiver part of the movable container support 315. Another part of the movable container support may be designed in such a manner to surround a part of the housing 301 when the movable container support is in second position.

Figure 12B:
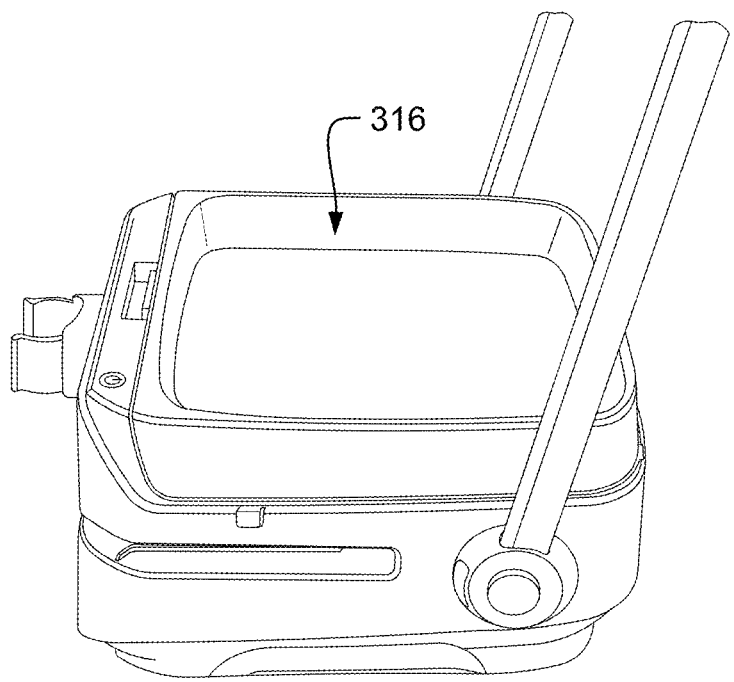

The FIG. 12b shows the movable container support in a third position so as to have an access to the container receiver 316. The movable container support may be removed from the apparatus (for example from the housing).

Figure 12C:
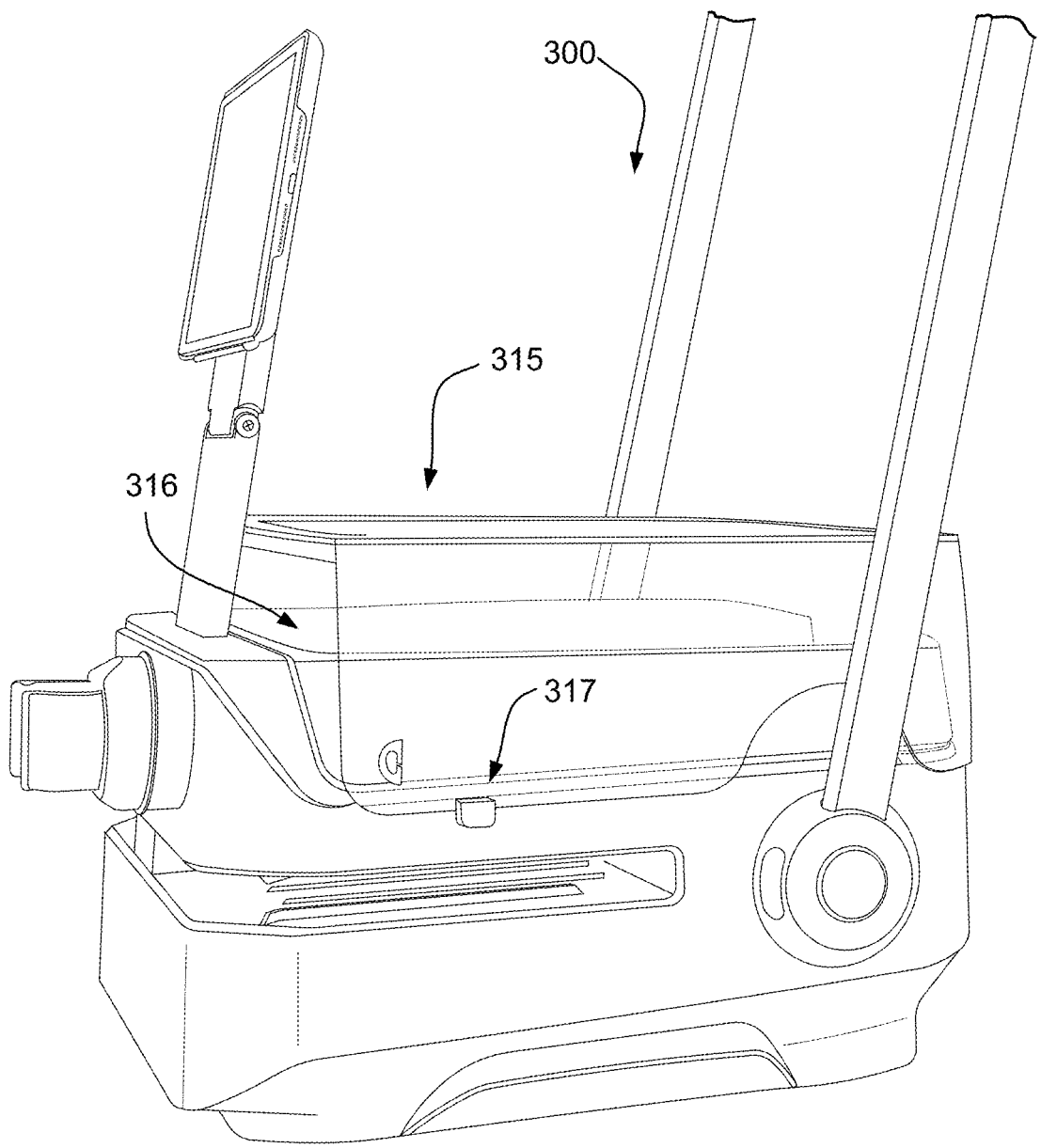
Figure 13:
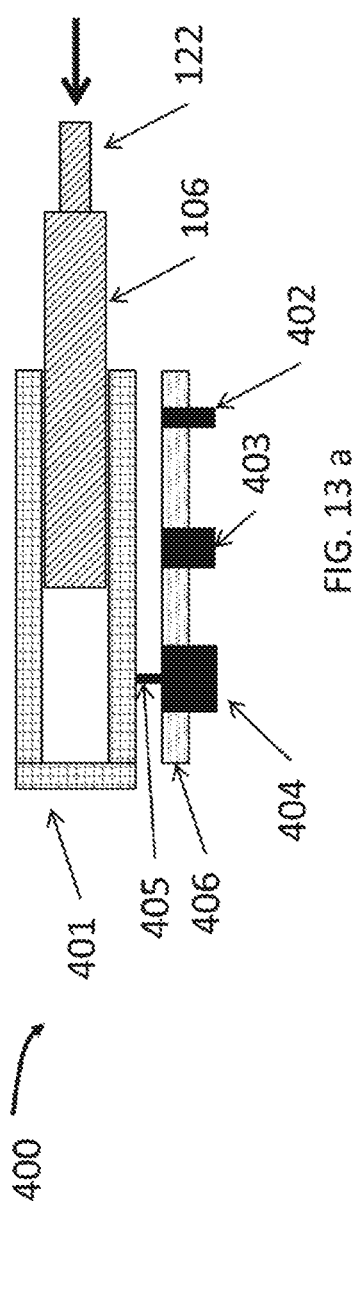
FIGS. 13a to 13g illustrate different views of the loading process of the cassette.
Figure 13:
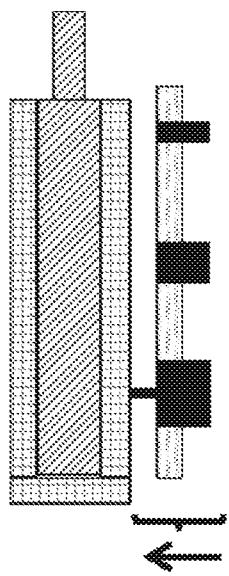
Figure 13:
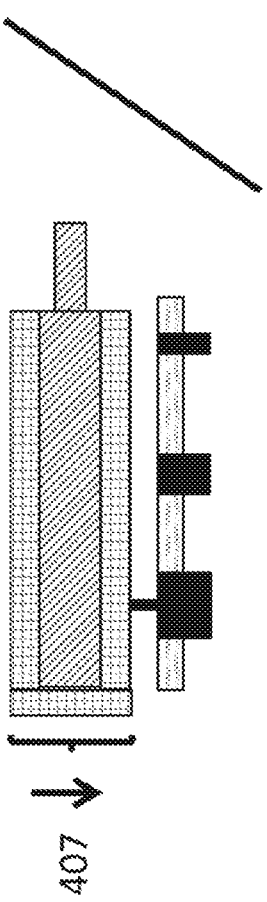
Figure 13:
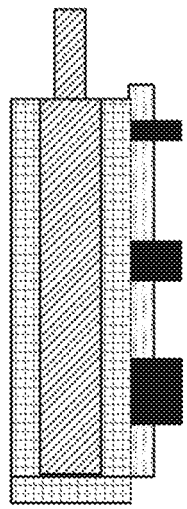

The FIG. 12c shows the movable container support 315 laid on or positioned on or secured to the fixing element 317 (for example the protrusion) when the movable container support is placed in a first position. In this position, a first solution bag may be stored in the movable container support 315 (for example a concentrate solution bag) and a second solution bag (different from the first, for example a dialysate solution bag or a saline solution bag) may be stored in the container receiver 316 (arranged below the movable container support). The container receiver 316 may comprise a heating element adapted to heat the bag stored in the container receiver. As the movable container support is placed above the heated bag, the bag stored in the movable container support can receive residual heat. The container receiver may be firmly secured to the apparatus.

This container receiver 316 may further comprise a weight scale in order to weigh the bag stored in the container receiver. The movable container support 315 may be designed in such a manner that the weigh scale is not disturbed by the movable container support or by the weight of the bag stored in the movable container support. In other terms, when the movable container support is in first position, (for example thanks to the fixing element and the shape of the container support or container receiver) the receiver part of the movable container support 316 is spaced far enough apart from the receiver part of the container receiver 316 in order to store a predetermined volume of fluid stored in the bag (received by the container receiver 316). In case where the system comprises a sorbent device and the container receiver stores the bag 13 of the FIG. 3, this volume of fluid is determined by taking into account a dialysate volume and the ultrafiltration resulting from the treatment. The dialysate volume may be a quantity commensurate with being recycled through the sorbent cartridge multiple times.

Preferentially the movable container support 315 receives a supply solution bag (for example a concentrate supply bag 31 or other) and the container receiver 316 receives a dialysate solution bag 13 (also called the weighing bag) used to mix and/or to weigh the cleaned dialysate (cleaned by the sorbent and comprising ultrafiltration) and a volume fraction of concentrate (progressively added during the treatment).

Figure 34:
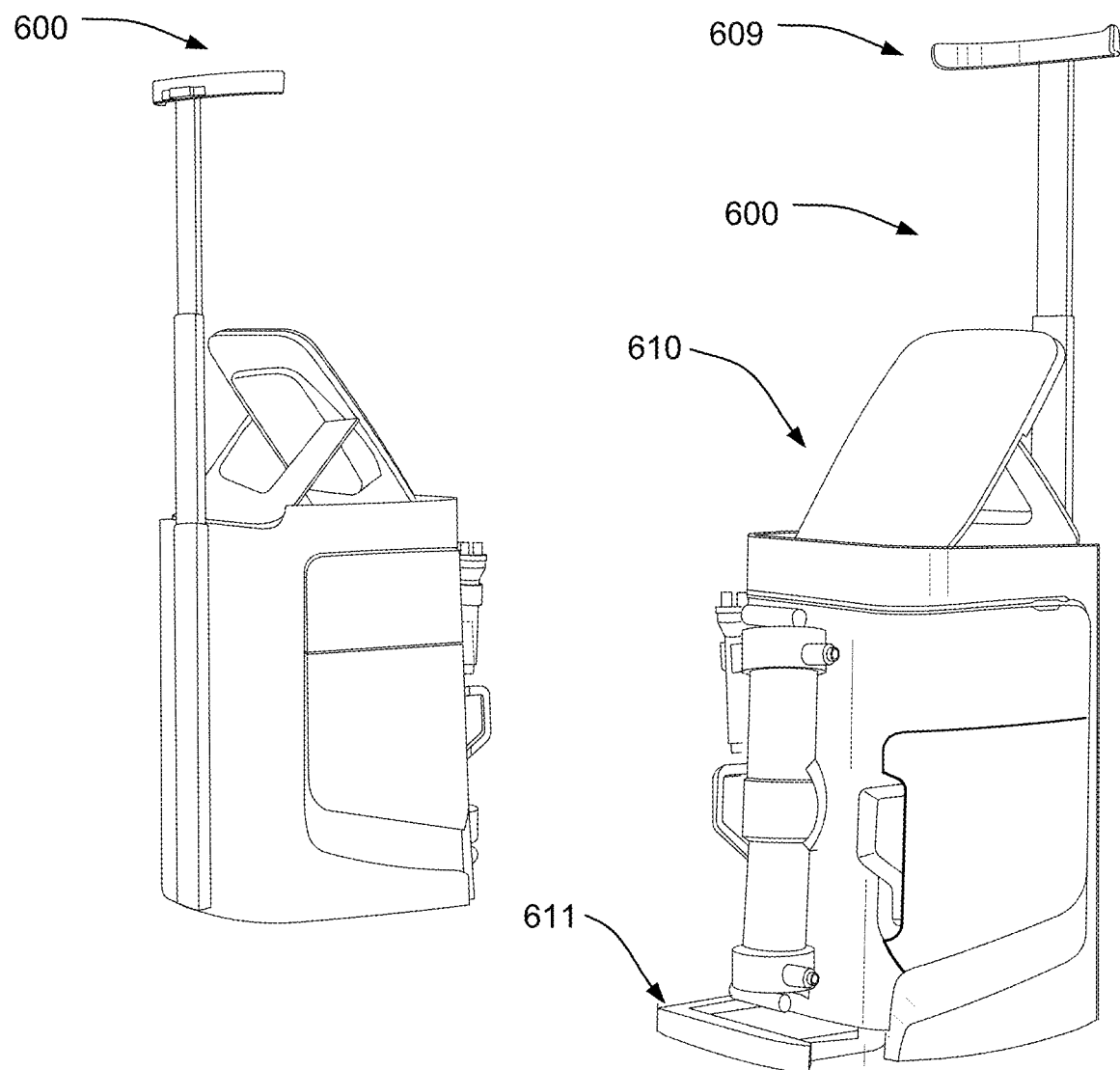

Referring now to the FIG. 33, the dialysis system 600 comprises an apparatus 601 having a housing 607, a first door 604 and a second door 605. The first door 604 is configured to allow accessing the cassette holder of the blood cassette 602 (for example). The second door 605 is configured to allow accessing the cassette holder of the dialysate cassette 603 (for example). The dialysis system 600 may comprise a loading system as described thereafter. The loading system may horizontally move the cassette holder (with or without the door) or the functional element support The FIG. 34 shows two views of the dialysis system 600 having a (extended and preferentially retractable) pole 609, a removable display device 610 and a weighting scale 611. The FIG. 35 shows the system 600 in functional condition. The system further comprises a sorbent device 612, the tubes 613 of the fluid circuits and the weighing bag 614.

The FIG. 36 show an apparatus support 615 which may be modular and may be used as a luggage with rollers (as described thereafter). The apparatus support 615 may be configured to store the apparatus 601 into a cavity of the apparatus support 615 in transport condition. Optionally, the apparatus support 615 may be configured to support or to receive the apparatus on a surface of the apparatus support in functional condition.

The apparatus support 615 may further comprise a sorbent support 616 arranged on a side of the apparatus support and which may be retractable into the apparatus support. The apparatus support may comprise rollers, a planar surface and side doors.

The FIG. 37 shows another potential embodiment 700 having an apparatus 701, a display device 710, a door 704 allowing accessing to the cassette holder(s) and a heating compartment 705. In this embodiment, the loading system may move up and down the cassette holder with the door.

The FIG. 39 shows the system 700 in functional condition. The system further comprises a sorbent device 712, the tubes 713 of the fluid circuit and the weighing bag 714.

Loading System

Two distinct loading systems may be used for the apparatus (for example shown by the FIGS. 13 to 17). For both systems, the loading system 400 comprises at least one of a drive mechanism and a cassette holder 401 intended to removably receive a cassette. The cassette holder 401 is arranged into the housing of the apparatus. The aim of the loading system may be to enable the coupling between dedicated active elements 404 (also called components), 403, 402 of the apparatus and the cassette 106. Preferentially the dedicated active elements are the active elements which are intended to be operatively coupled to the cassette (for example to the coupling area and/or to the measurement area of the cassette) during the operating process (during the treatment, or a part of test process, for example). The dedicated active elements may be at least one of a sensor 402 (air, pressure, blood detector, . . . ), an actuator of the pump 404, a valve 403, and . . . . A part or all dedicated active element may be arranged on a support 406. Said support may be plate or a frame structured or/and intended to receive and/or to be in contact with or closer to an operative face of a cassette (in operating configuration). The operative face of the cassette is a face or a part of a face which comprises the measurement area (intended to cooperate with the pressure sensor of the apparatus) and/or the coupling area (intended to cooperate with the valve actuator, the pump mechanism or other actuator of the apparatus).

The drive mechanism is adapted to enable a first position wherein the cassette may be operatively coupled with the dedicated active elements of the apparatus and a second position wherein the cassette is not coupled with (for example spaced apart from) the dedicated active elements of the apparatus. The second position further allows charging the cassette into or removing the cassette from the cassette holder. When the loading system is in second position the opening and/or the cassette holder may be illuminated in order to inform the user that he can insert a cassette or remove the cassette. The illumination may be a specific color, for example a first color when the loading system is in a first position and a second color (different from the first) when the loading system is in a second position. Another indicator device may inform the patient about the position of the loading system, for example a sound, a voice, a movie, a text on the display device or on the additional display ora light illuminating a part of the dialyzer support.

The cassette holder 401 comprises at least one of a guiding means (for example rail or (linear) guiding element) adapted to cooperate with the cassette in order to allow a sliding (relative) movement (of the cassette relatively to at least one of the cassette holder, the components and the housing), a mechanical stop, and a sensor. The sensor may be adapted to detect an insertion of a cassette and/or a full insertion of the cassette. The sensor may be adapted to determine if the element inserted (into the opening) is a cassette or other (for example a finger, . . . ). For example the sensor may be an optical sensor connected to the processor of the apparatus. For example, a transmitter emits an (invisible infrared) light beam to a receptor. The processor detects a finger or other things when the receptor does not receive the (infrared) light beam. The cassette may be substantially transparent thus the receptor can recognize the cassette thanks to the dispersed light which is detected by a sensor. The sensor may be arranged near the opening and/or near the mechanical stop.

In one embodiment, a first sensor may be arranged close to a first end into the receiving compartment of the cassette holder (for example the opening) in order to detect the insertion of an object. A second sensor may be arranged close to another end into the receiving compartment of the cassette holder (for example an opposite end of the first end) and adapted to detect a cassette fully inserted. In this embodiment, the first sensor may be optional. When the loading system is in a second position, the display device may display a message so as to inform the user to insert the cassette. After a predetermined period of time, if the first sensor does not detect any passage then the display device may display a message so as to inform the user that no cassette has been detected and an audible alarm may be triggered. If the first sensor detects an object but the second sensor does not detect any object after a predetermined period of time, then the display device may display a message so as to inform the user that the cassette has not been fully inserted and an audible alarm may be triggered. If the first sensor and the second sensor (or at least the second sensor alone) detect the cassette then the processor may authorize the loading process (for example the passage from the second position to a first position, which also described thereafter) or may automatically initiate the drive mechanism (for example the change of position). A secure loading mechanism (as described thereafter) may check that both sensor or at least the second sensor detect the full insertion of the cassette and initiate the change of position when the user command the loading process (for example by pushing a button as described thereafter). If the user does not command the loading system, then the display device may display a message so as to prompt the patient to push the button (for example).

In brief, the method of insertion may comprise the steps of:
  Inserting the cassette through the opening of the apparatus;
  Detecting the cassette; and
  Allowing the activation of the loading system when the cassette is fully inserted.

In other terms, the processor, which operates with the loading system, is adapted to:
  Receive a signal of at least one sensor corresponding to a detection of a cassette in the cassette holder,
  Allow the activation of the loading system when the cassette is fully inserted, The processor may be further adapted to (as similarly described thereafter)
  Receive a signal corresponding to an activation of one or more button, said activation and allowance being verified by the security loading mechanism;
  Initiate the change of position of the loading system by activating the drive mechanism.

Before starting the treatment (for example before that a fluid wets the cassette), the system may be adapted to abort the treatment if requested by the user. Thus, the system may comprise a button (for example a cancel button) arranged on the housing or displayed on the display device allowing to stop the process and to save the unused cassette. In this case, the processor may control the drive mechanism so to change the position if needed (from the first position to the second position) and the user can remove the cassette in order to use it at another time.

The cassette holder comprises one or more specific area (hole, opening, . . . ) where the dedicated active elements are intended to be coupled with the cassette.

According to a first embodiment, the drive mechanism is adapted to move the cassette holder (also called movable holder of cassette) relatively to the apparatus (for example to at least one of the housing, to the opening, and the fixed support of components). The support 406 of the dedicated active elements 406 (also called fixed support of components) may be firmly secured into the apparatus and are not moved by the drive mechanism.

According to a second embodiment, the drive mechanism is adapted to move one or more dedicated active elements (for example the support (also called movable support of components)) relatively to apparatus (for example to at least one of the housing, to the opening and the fixed holder of the cassette). The cassette holder (also called fixed holder of the cassette) may be firmly secured into the apparatus and are not moved by the drive mechanism.

According to another embodiment, the drive mechanism is adapted to move one or more dedicated active elements and the cassette holder relatively to apparatus. Thus, the drive mechanism is used to bring the dedicated active elements and the cassette holder closer or to move away.

In all cases, preferentially, the opening(s) of the housing does (do) not move with the drive mechanism. In other terms, the opening(s) of the housing may be fixed and/or may have a fixed perimeter. Thus, according to the first embodiment described above, the openings of the cassette holder are aligned with the opening of the housing only when the loading system is in second position. According to the second embodiment described above, the (openings of the) cassette holder are aligned with the opening of the housing when the loading system is in first position and when the loading system is in second position. Thanks to this embodiment, there are no risk of pinching fingers.

Referring to the FIG. 13*a*, the first embodiment and the second embodiment may be used here. The loading system 400 is in open position allowing inserting the cassette into the cassette holder. The dedicated active elements are spaced apart from the specific area.

According to the FIG. 13*b*', the cassette holder is moved by the drive mechanism relatively to the dedicated active element in order to put the loading system (or the cassette holder) in a first position. According to the FIG. 13*b*'', the dedicated active elements (or the support) are moved by the drive mechanism relatively to the cassette holder in order to put the loading system (or the dedicated active element or the support 406) in a first position.

The FIG. 13c shows the loading system 400 in the first position wherein the cassette may be coupled to the dedicated active elements. This position is maintained during the operating process, for example during the treatment.

According to the FIG. 13d', the cassette holder is moved by the drive mechanism relatively to the dedicated active element in order to put the loading system (or the cassette holder) in a second position. According to the FIG. 13d", the dedicated active elements (or the support) are moved by the drive mechanism relatively to the cassette holder in order to put the loading system (or the dedicated active element or the support 406) in a second position.

The FIG. 13e shows the loading system 400 in the second position. The dedicated active elements are spaced apart from the specific area. The cassette can be removed from the cassette holder.

The FIG. 13f shows the loading system 400 in a first position but without cassette. The FIG. 13g shows the loading system 400 in a second position without cassette. The FIGS. 13f and 13g show a rest position which may be required when the apparatus is not used or is moved.

In one embodiment, an active element (such as (pinch) valve actuator or pumping mechanism) may act in an opposite direction of the drive mechanism and may induce a non-intentional displacement of the loading system. For example, when the valve actuator is actuated to close a fluid pathway, the valve actuator may push on the cassette and induce a non-intentional displacement of at least one of the movable holder of the cassette and the movable support of the components. A first solution may be a lock device configured lock the position of at least one of the movable holder of the cassette and the movable support of the components. A second solution may be that the component(s) which may induce such non-intentional displacement is not arranged on the movable support of the components. Thus, an embodiment may comprise a fixed support of the components and a movable support of the components. One or more component (such as valve actuator, sensor, pumping device or other) may be arranged on (fixed to) the fixed support of the components while one or more component (such as valve actuator, sensor, pumping device or other) may be arranged on (fixed to) the movable support of the components. The movable support may be configured to be moved by the drive mechanism in order to move the component or the movable support in a determined position. The fixed support may be fixed to at least one of the cassette holder, the (frame of the) apparatus and the housing and is configured not to be moved by the drive mechanism (or not to cooperate with the drive mechanism).

For example, in order to prevent or limit the hemolysis, the valve(s) of the blood line may be a pinch valve configured to pinch a flexible tube (for example of the (blood) cassette). This type of valve may induce a non-intentional displacement thus the pinch valve may be arranged on a fixed support while at least one other component (pumping device, sensor, other actuator, . . . ) may be arranged on a movable support. In this case, the pinch valve (and other components fixed to the fixed support) may have at least one of an actuated state (for example closing the fluid pathway when the loading system is in first position), a non-actuated state (for example opening the fluid pathway and/or when the loading system is in second position) and a disengage state (for example when the loading system is in second position).

The loading system 400 may comprise a lock system which locks the inserted cassette in order to prevent a movement of the cassette during the treatment. This lock system may be at least one pin which cooperates with at least one cavity (for example a hole) of the cassette. The lock system may be activated by the drive mechanism. Thus, when the drive mechanism puts the loading system in the first position, the pin enters into the cavity of the cassette. And when the drive mechanism puts the loading system in the second position, the pin is removed from the cavity of the cassette. The lock system may be used to perform a fine alignment of the cassette with the dedicated active element as a guiding element when the drive mechanism puts the loading system in the first position. The alignment of the cassette with the dedicated active element may be (fully or partially) insured by the shaft of the pump. The lock system may be the shaft of the pump when insert between the rollers.

The dialysate cassette holder may comprise a "dialysate" dedicated loading system and the blood cassette holder may comprise a "blood" dedicated loading system. Both dedicated loading systems may be substantially simultaneously activated or initiated. Or each dedicated loading system has to be separately activated or initiated. In case of dedicated loading system, each dedicated loading system may comprise a dedicated drive mechanism or both dedicated loading systems may be drove by a single drive mechanism.

The drive mechanism of the loading system (dedicated or not) may be automatically activated by the processor or may be enabled when the sensor of the cassette holder detects a full insertion of the cassette into the cassette holder. The drive mechanism may be activated by the user. The apparatus may comprise a secure loading mechanism which prevents a finger pinching when the user activates the drive mechanism. The secure loading mechanism may be software solution and/or a hardware solution. For example, the apparatus may comprise two distinct buttons arranged for example on the housing or on the touch screen. Both buttons may have to be substantially simultaneously activated by the user to initiate the change of position of the loading system (from the second position to the first position). Preferentially, the buttons are spaced far enough apart from each other in order to compel the user to use both hands (for example at least the average length of a child's hand). The button may be also spaced far enough apart from the opening(s), a safe distance may be equal to the length of a hand (for example at least the average length of a child's hand).

The secure loading mechanism may be adapted for preventing the patient from inadvertently initiating the change of position. For example, the secure loading mechanism may be configured to prevent the processor from initiating the change of position unless the user activates a button (arranged on the housing or spaced apart from the housing or on the touch screen) according to an activation sequence and the sensor detect a full insertion of the cassette. The activation sequence may compel the user to hold the button activated or pressed during a predetermined time period (for example until the loading system has reached the first position). Thus, if the user no longer presses the button, the secure loading mechanism may send a signal to the processor in order to stop the loading process and go back to the second position the loading system. Thus the loading process may comprise the following steps:

Receive (by the processor) a signal corresponding to an activation of one or more button according to an activation sequence by the user, said activation being verified by the security loading mechanism;

Initiate the change of position of the loading system (or initiate the loading of the cassette into an operating configuration) by activating the drive mechanism; and, Stop the drive mechanism or put the loading in an initial position (for example in the second position) by the secure loading mechanism in case of failure (for example if the user no longer presses the button according to an activation sequence).

The apparatus may comprise a sensor adapted to monitor or to detect at least one of first position and second position of the loading system 400. The sensor may be an optical sensor, a hall effect sensor, . . . . A first sensor may be intended to detect the first position and a second sensor may be intended to detect the second position.

In operating configuration, if the processor detects a change in the position, the processor may activate (temporarily or continuously) the drive mechanism in order to maintain the good position. In other embodiment, the cassette is maintained in the correct position throughout a treatment by friction. The loading system applies a residual force on the cassette (by design) and the processor does not apply any additional power to the drive mechanism.

The electrical load data (of the drive mechanism) is transmitted to the processor (also called processing unit). The electrical load data may be the voltage applies to the motor of the drive mechanism. When the voltage reaches a predetermined value, the processor may stop the motor. The electrical load data may be also used to detect a jam condition. In order to determine if a change (a peak or a threshold) of the electrical load data is caused by an end of the loading process or by a jam condition, the system may use data sent by the position sensor. For example, when the loading system moves from the second position to the first position, the second position sensor sends a signal to the processor for example so as to inform that the loading system is no longer at the second position (or, conversely, from the first to the second position, the first position sensor sends a signal to the processor). The processor monitors the electrical load data and if a predetermined threshold is reached before receiving a signal of the first sensor (for example for informing that the first position is reached), then the processor determines a jam condition. The processor triggers an alarm and the loading system goes back to the second position automatically. If a predetermined threshold is reached after receiving a signal of the first sensor (for example for informing that the first position is reached), then the processor determines that the first position is reached and stops the motor of the loading mechanism. The processor allows passing to the next step of the process.

In brief, the method of loading may comprise the steps of:
Initiating a change of position of the loading system (for example from the second to the first position or vice-versa);
Sensing a change of position (optional) (for example via the position sensor);
Sensing an electrical load data increase; and
Causing the stop of the loading process in jam condition or when the loading system has been reached the wanted position In other terms, the processor, which operates with the loading system, is adapted to:
Initiate (for example if all condition is ok as described above) the loading process (for example initiate the motor of loading mechanism)
Receive the signal of at least one position sensor (for example from the second position sensor),
Receive the electrical load data of the motor
Stop automatically the loading process (for example the motor) when a predetermined threshold has been reached (for example of the electrical load data)

If the processor receives a signal from the other position sensor (for example the first position sensor) before reaching a predetermined threshold then the processor determine that the wanted position has been reached and passes to the next step.

If the processor does not receive any signal from the other sensor (for example the first position sensor) while a predetermined threshold is reached then the processor determines a jam condition and optionally initiates the motor in a reverse mode so as to go back to the initial position.

The predetermined threshold of the jam condition may be higher than or smaller than or equal to the predetermined threshold of the end of the loading process.

This method describes more particularly the loading process but the same concept may be applied to the unloading process.

Figure 14:
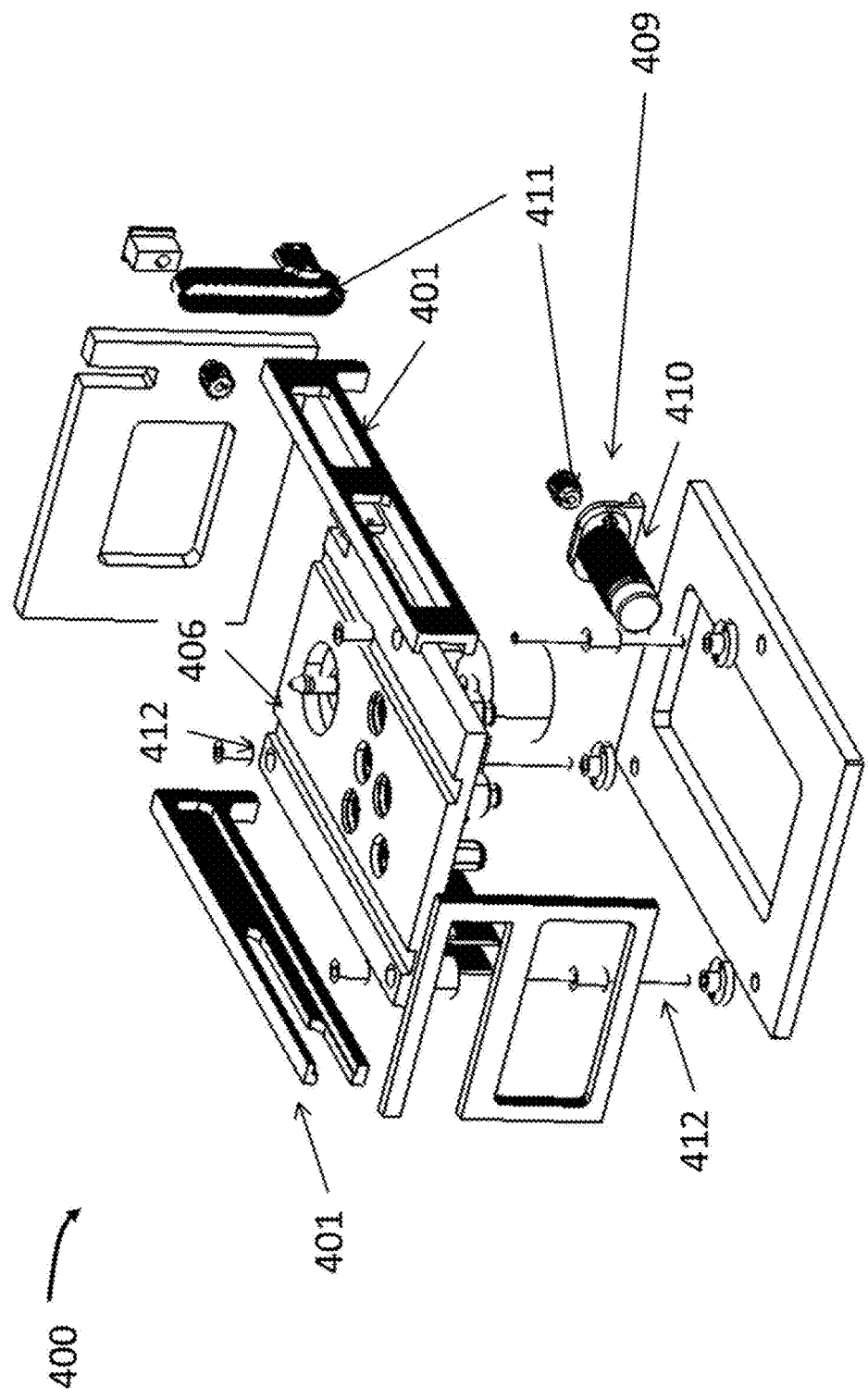
FIG. 14 shows an exploded view of one embodiment of the loading system.
Figure 15C:
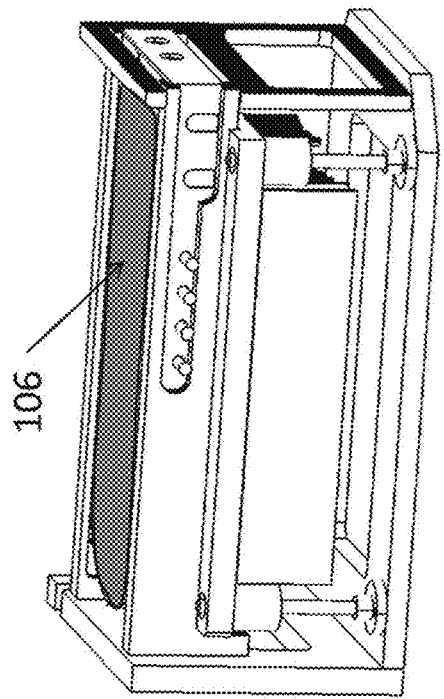
FIGS. 15a to 15d shows different positions of the loading system with or without cassette.
Figure 15D:
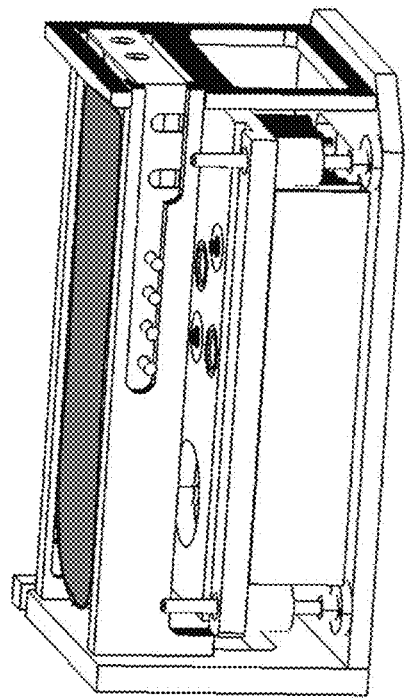
Figure 15A:
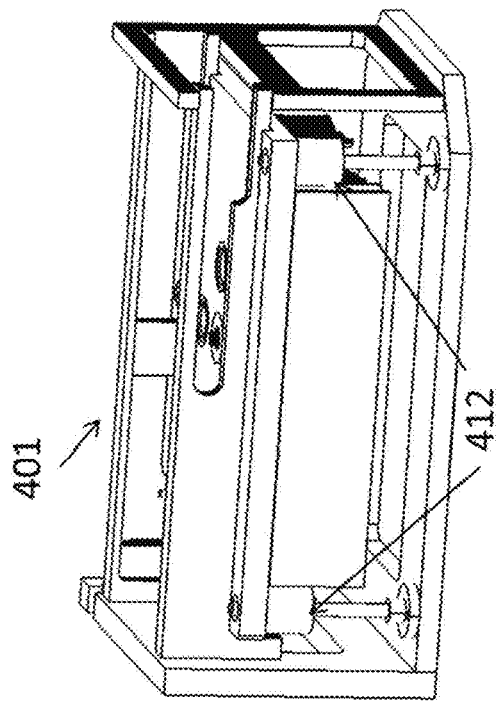
Figure 15B:
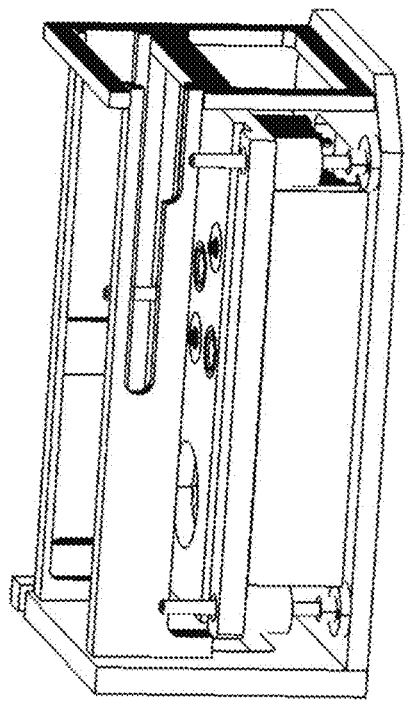

The FIG. 14 is an exploded view of a loading system 400. The loading system 400 comprises cassette holder 401, a support 406 (for example a movable support) of the dedicated active elements and a drive mechanism 409. In this embodiment, the drive mechanism may comprise an electric motor 410, a drive assembly 411 (for example a toothed drive assembly) and a guiding assembly 412. The guiding assembly 412 may comprise one or more linear guiding element (such as rod) rod (preferentially 2, more preferentially 3) and one or more sliding element (for example through holes (preferentially 2, more preferentially 3)) intended to slide along the rod. The sliding element may be arranged on or secured to the support of the dedicated active element.

The FIG. 15 show 3D views of one embodiment of the loading system in which the drive mechanism is adapted to move the support of the dedicated active elements relatively to the apparatus. The FIG. 15*a* shows the loading system in a first position without cassette, the FIG. 15*b* shows the loading system in a second position without cassette, the FIG. 15*c* shows the loading system in a first position with a cassette and the FIG. 15*d* shows the loading system in a second position with a cassette. In this figures, the cassette is inserted through a first opening of the cassette support, the cassette holder further comprises a second opening to pass the tubes of the cassette laterally (which is perpendicular to the first opening).

Figure 16:
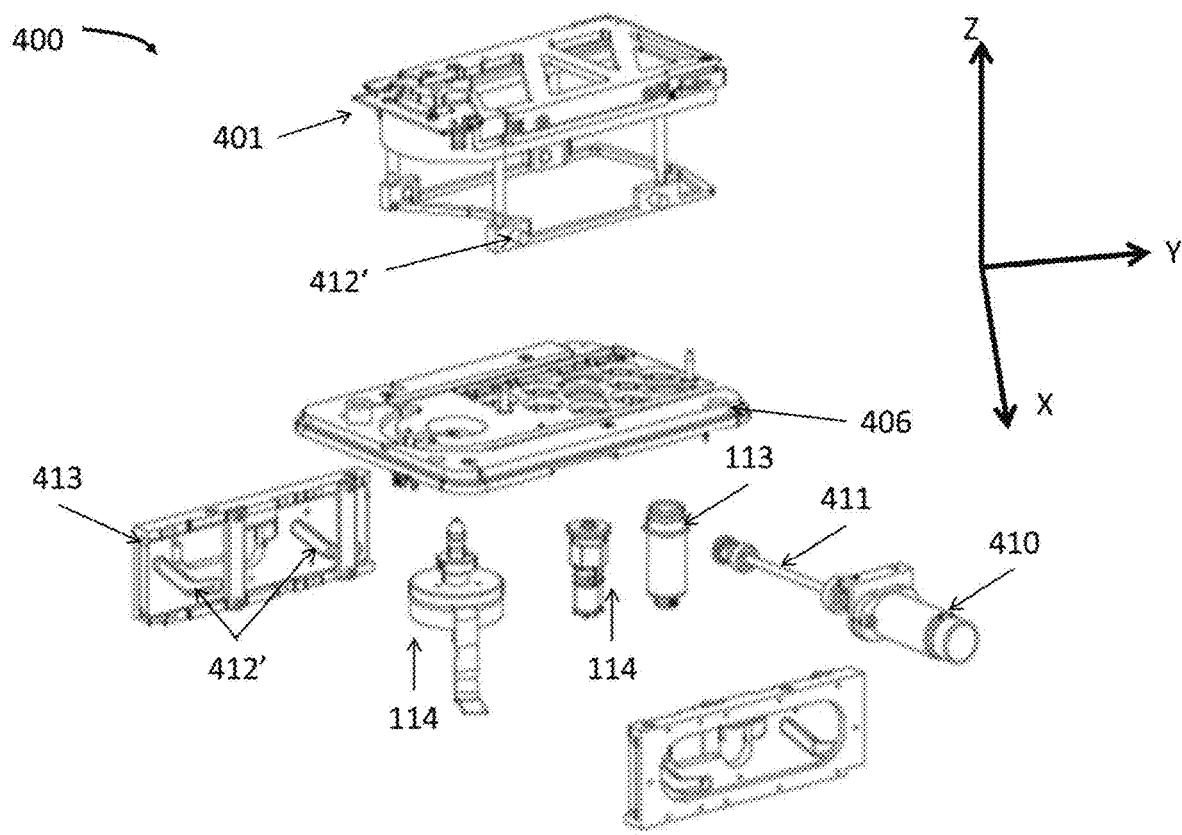
FIG. 16 shows an exploded view of one embodiment of the loading system.
Figure 17:
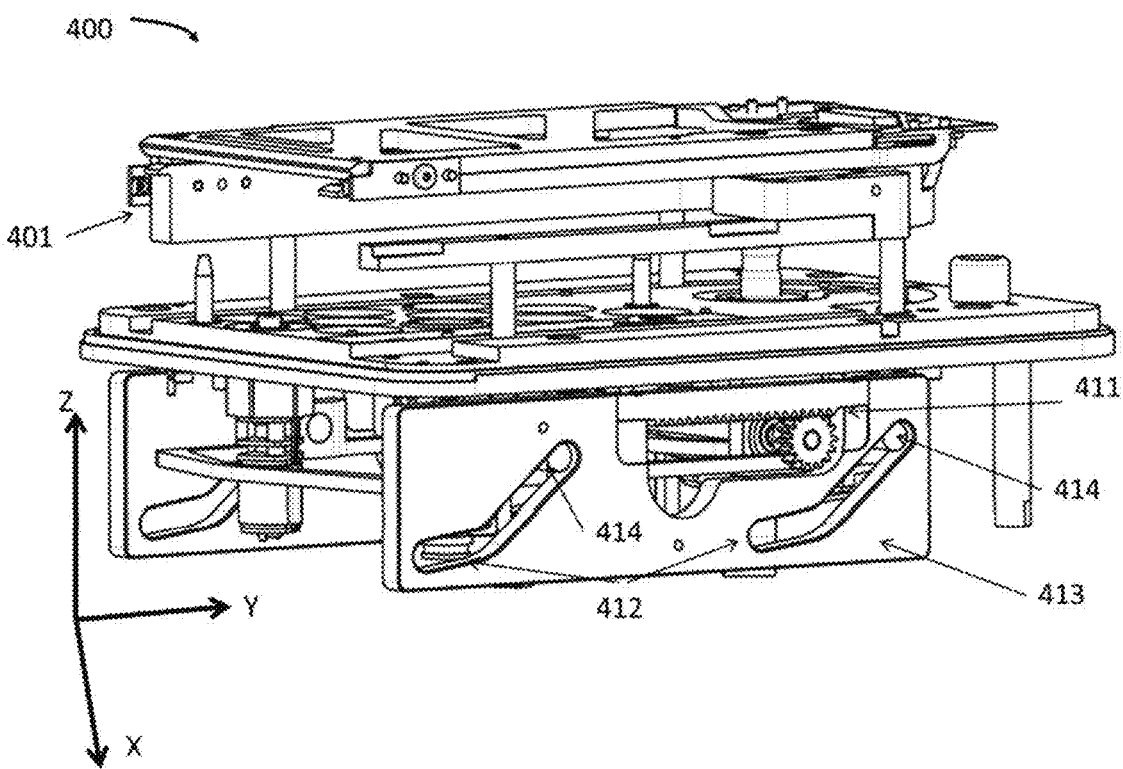
FIG. 17 shows a 3d view of one embodiment of the loading system.

The FIG. 16 discloses an exploded view of an example of the first embodiment of a loading system 400. The loading system 400 comprises cassette holder 401 (for example a movable holder of the cassette), a support 406 of the dedicated active elements and a drive mechanism 409. The drive mechanism may comprise an electric motor 410, a drive assembly 411 (for example a toothed drive assembly) and a guiding assembly. The guiding assembly may comprise one or more guiding element 412' (preferentially 2, more preferentially 4) and one or more sliding element 412' (such as pin (preferentially 2, more preferentially 4)) intended to slide along or against the guiding element.

The sliding element may be arranged on or secured to the support of the dedicated active element. The guiding elements are arranged on a support 413 (for example a plate or a frame) which moves relatively to the apparatus. The guiding elements are intended to transform a first axial movement into a second axial movement which is different from the first axial movement (for example perpendicularly). The guiding elements may have an opened L shape, a comma shape, . . . . The motor 410 is actuated in order to rotate a pinion gear which moves the guiding element support 413 in accordance with a Y axe. The loading system is designed in such a manner that the movement of guiding element support induces a movement of the cassette holder in accordance with a Z axe (which is perpendicular to the Y axe). For example, the cassette holder has a movement restrictor adapted to prevent movements other than Z axe movement. Thus, a Y axe movement of the guiding element induces a Z axe movement of the pin (relatively to the apparatus).

Door Device

In order to protect the active element(s) of the apparatus and/or to substantially obstruct the opening (with or without cassette), the system may comprise a door device comprising a door device (also called door) and/or a flexible element. For example the door may be a sliding door or a retractable door or a revolving door or swing door. For example the flexible element may be a sheet and may cover at least partially the opening. The flexible element may be adapted to be bend when the cassette is inserted into the opening or when tubes or handle protrude from the opening. An example of a flexible element 423 is shown in the FIG. 30g. In this case, the flexible element is fixed to the apparatus, for example to the apparatus body (such as the housing), or for example to a moveable part of the apparatus body (such as the housing).

The opening and/or the closing of the door device may be manual and/or automatic for example controlled by the processor. Preferentially, the door 415 is (initially) closed and may be open only in order to insert a cassette into the opening. The door may comprise two positions an open position which allows loading or unloading a cassette into/from the cassette holder and a closed position which substantially or at least partially obstructs the opening.

Figure 31A:
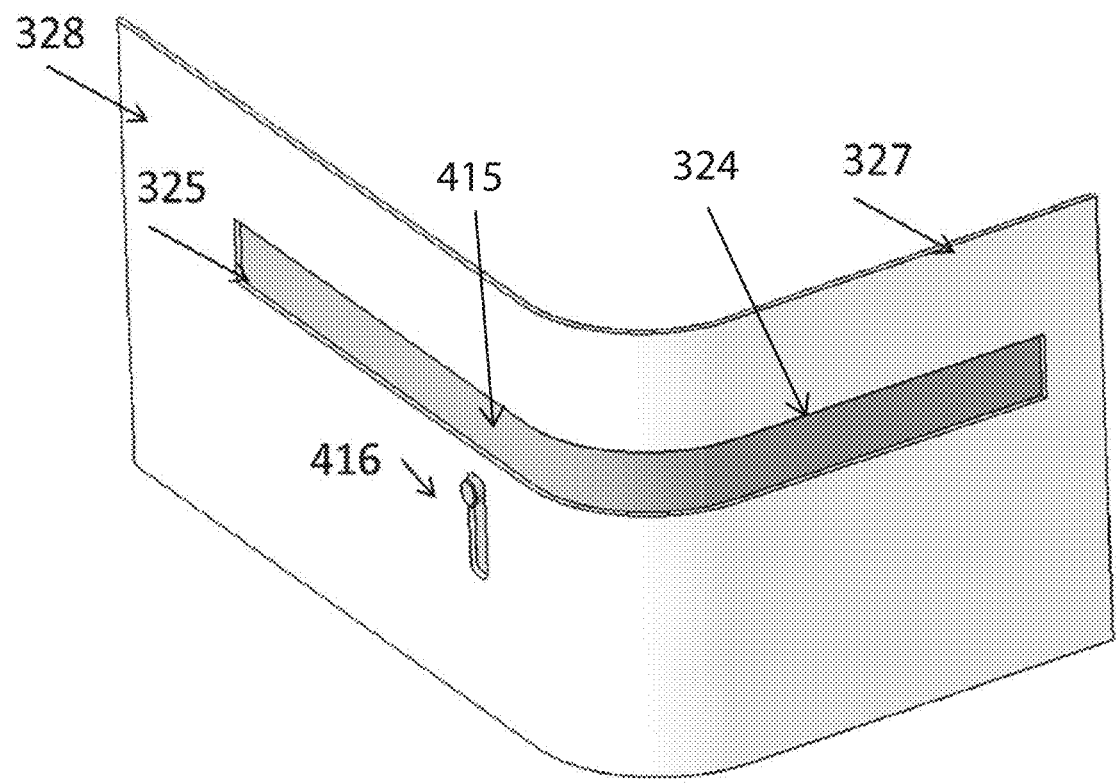
FIGS. 31a and 31b show two embodiments of the door device.
Figure 31B:
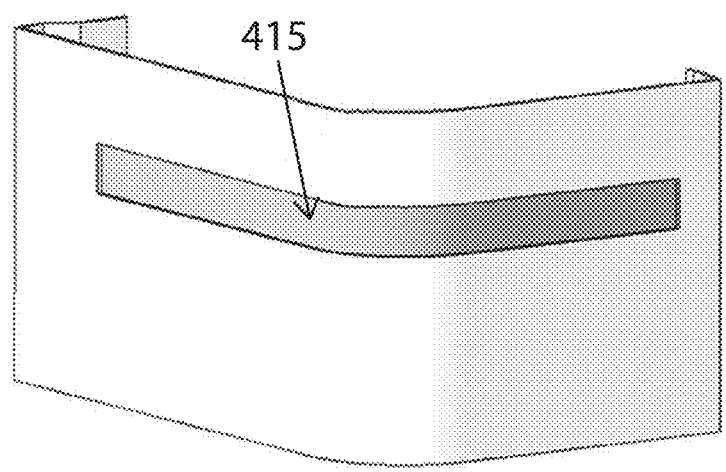

The FIGS. 31a and b show a part of the housing comprising a door device including a sliding door. The embodiment shown by the FIG. 31a further comprises a manual door actuator 416 configured to manually open and/or close the sliding door. The user can lower (or respectively pull up) the manual door actuator in order to slide the door so as to open or to close the door.

The door device may comprise a lock system 418 (for example as shown by the FIG. 32) and/or a constraint system 419 in order to maintain the door in a determined position, for example in an open position or in a closed position. At least a part of the lock system 418 and/or at least a part of the constraint system 419 may be rigidly fastened to a (rigid) body of the apparatus (for example a part of the housing).

Figure 32:
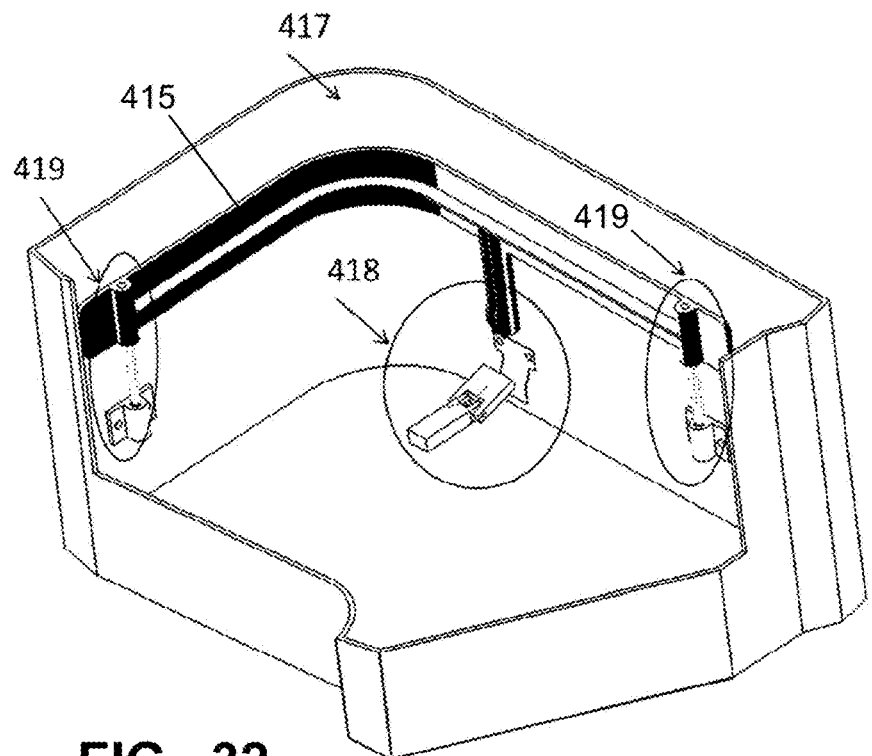
FIG. 32 is an interior view of the FIG. 31a or of the FIG. 31b.

The FIG. 32 is an interior view of a (rigid) body of the apparatus (for example a part of the housing), some elements are not shown in order to focus on the lock system 418 and the constraint system 419.

The door device may comprise a protrusion adapted to be removably coupled to the lock system 418 when the door is in a determined position (for example when the door is opened) such that the user can easily insert the cassette. The lock system may comprise elastic element (spring, elastic strip, . . . ) which constraints a retaining element (lug, clip, protrusion, anchor, . . . ) adapted to be coupled with the protrusion of the door. The lock system may be disabled by the user by pushing on the manual door actuator (for example). The lock system may be disabled by the processor via a dedicated (connected) actuator (not shown) or via the loading system. In the last case, the loading system may be adapted to disable the lock system when the loading system is actuated (when is moved from a first position to a second position and/or vice versa).

The door device may comprise a sliding element adapted to slide through a guiding element of the (rigid) body of the apparatus (for example a part of the housing) in order to restrict the movement of the door (or inversely, the apparatus body may comprise the sliding element and the door may comprise the guiding element). The sliding element may be a through hole or a protrusion of the door device and the guiding element may be a rod (for example steel rod) or a recess for example arranged on the (rigid) body of the apparatus (for example a part of the housing).

The constraint system 419 may exert a force against the door and against the (rigid) body of the apparatus (for example a part of the housing) so as to close the door or to force the door in a closed position. The constraint system 419 may comprise elastic element (spring, elastic strip, . . . ).

In a preferred embodiment, the door is opened thanks to the loading system and is closed by the constraint system. In this case, the door device and/or the loading system may comprise a coupling element 422 (as shown by the FIG. 30).

The coupling element 422 may be configured to mechanically cooperate with the loading system according to at least one dimension. The coupling element may comprise a protrusion arranged on at least one of the movable support 406 and the door device 415. The coupling device may further comprise an associated device (such as a contact space, a sliding element, a hole, a slot or a groove) configured to cooperate with the protrusion (for example by contact or slip). The coupling device may cooperate with the loading system when the loading system moves the movable support in at least one direction (for example from the first position to the second position and/or vice versa).

Thus, for example, when the loading system is moved to the second position, the loading system pushes the door device down in order to open the door (and the constraint system may be compressed). When the loading system is moved to the first position, the constraint system may push up the door in order to close the door and the coupling device or the inserted cassette may limit the displacement of the door. When the The coupling element may be disabled by the processor (via for example an actuator) or via a button pushed by the user (as disclosed by the FIG. 31a) thus even if the loading is in second position, the door may be closed by disabling the coupling element.

In one embodiment, when the loading system moves in a second position, the loading system opens the door via the coupling element and then a lock system maintains the door in open position. The coupling element or the lock system may be disable in order to close the door (even if the loading system is in the first or second position) by the processor or the user as disclosed above.

The FIG. 30a shows a door 415 in closed position and the loading system in a first position without cassette. The system comprises an elastic element 421 which may be a spring or an elastic strip or arm which constraints the door 415 in a closed position. The door and/or the loading system further comprises a coupling element 422 configured to (only) allow the loading system to move the door up to an open position (for example: from a closed position to an open position) as shown in the FIG. 30b. The FIGS. 30c and 30d show the embodiment with an inserted cassette. The cassette 106 is inserted and the loading system is in a first position. In the FIG. 30c, the door is no longer maintained in open position by the loading system but by the cassette. The door may be used to block the cassette inserted when the loading system is in first position. In the FIG. 30d, the door is in closed position with an inserted cassette.

The door device may comprise several parts of door such that a first part of the door device may fully close the opening (for example: where the cassette does not comprise any protrusion which extends outside the apparatus (no tube no handle)) and such that a second part of the door device may maintain in a open position or in a partial closed or open position (for example: where the elements of the cassette protrudes and extends outside the apparatus (such as handle, tubes, . . . ))

The FIGS. 30e to 30h discloses another embodiment where the loading system moves the cassette holder, for example such embodiment may be adapted for the apparatus shown in the FIG. 37. In this embodiment, the loading system may move the container receiver or the top housing up and down (and have a sliding door as described above). The FIGS. 30e to 30h show the last case. The system comprises a sliding door 415, a top housing 420', a (movable) cassette holder 401 and a (fixed) element support 406. The loading system is configured to move the cassette holder. The sliding door is maintained in a first position by an elastic element (spring or other similar element).

Figure 30E:
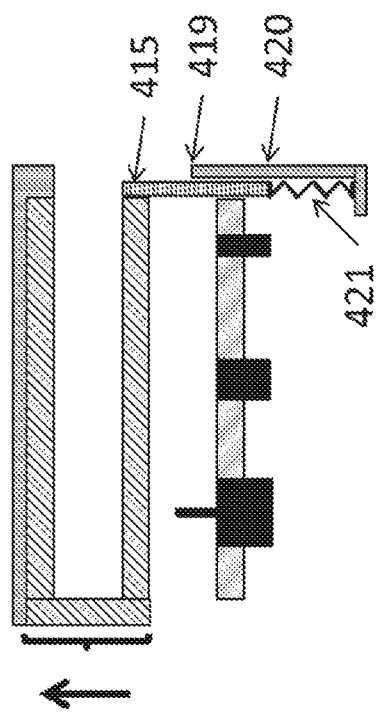
Figure 30G:
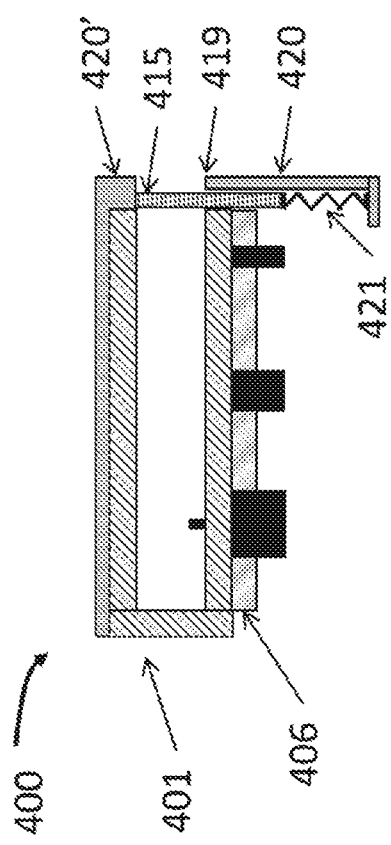
Figure 30F:
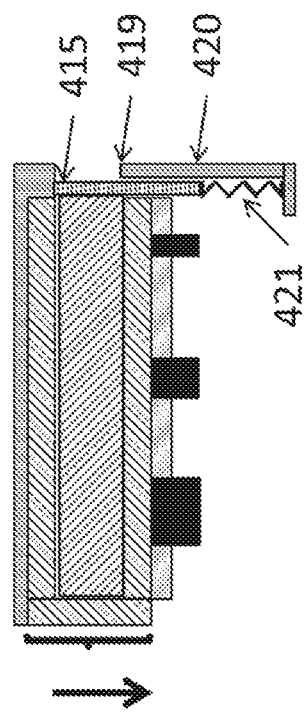
Figure 30H:
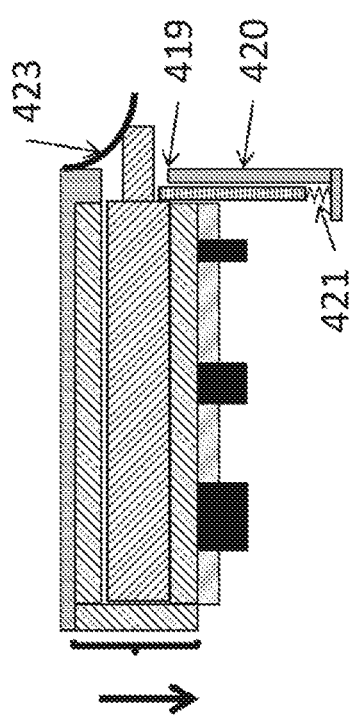

When the loading system is in first position without cassette, the sliding door 415 is maintained in the first position by the elastic element such that the door closes the opening. In FIG. 30f, the loading system moves in the second position, the sliding door is substantially in a same previous position (a mechanical stop may maintain the sliding door in a first position) but the cassette holder is in an open position. In FIGS. 30g and h, a cassette has been inserted and the loading system is in first position. Referring to the FIG. 30g, an element of the cassette protrudes from the opening and the door is maintained by this element in the open position or in an intermediary position for example in a partial close or partial open position. Referring to the FIG. 30h, the cassette is inserted and the door is closed.

In another potential embodiment, the door device may comprise a swing door which is opened on top or laterally.

Drip Chamber Support

Figure 18:
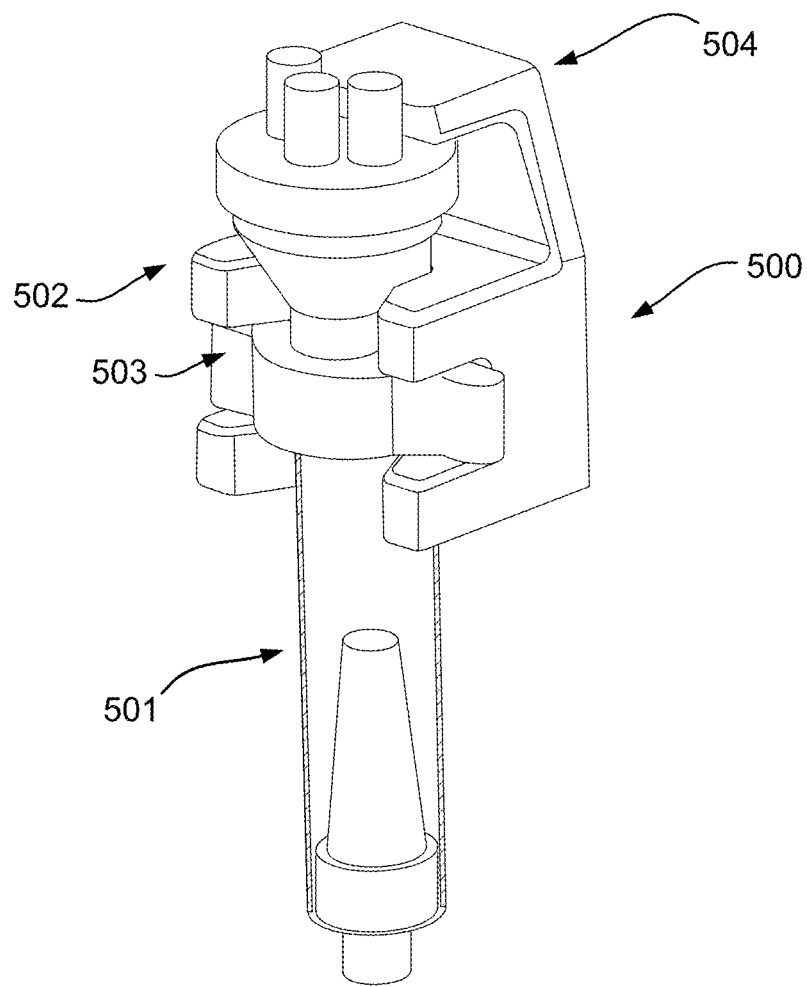
FIG. 18 shows a drip chamber and its support.

As shown by the FIG. 18, the drip chamber 501 is used to remove air bubble from the blood circuit. The support 500 of the drip chamber 501 is used to removably fix the drip chamber to the apparatus. The drip chamber support 500 may be arranged on a face of the apparatus housing or in the pole. The FIG. 18 shows an embodiment of the drip chamber support 500 with a drip chamber 501. The drip chamber support may comprise a body 502 secured to the apparatus and a level sensor. The level sensor may be an optical sensor, a wave sensor or a capacitive sensor. The level sensor is preferentially arranged into the body of the drip chamber support. The drip chamber support may further comprise a mechanical coding system 504 intended to maintain or insure a good/required position of the drip chamber relative to the drip chamber support or to the level sensor. The coding system 504 is designed in order to compel the position of the drip chamber relatively to the drip chamber support. For example, the drip chamber support may have a protrusion. The protrusion may be adapted to adjust the vertical position of the drip chamber in accordance with the level sensor. The drip chamber support may have a lock system 503.

Luggage

In order to improve the travel experience, the system may comprise an apparatus support (such as a bag or a luggage or a movable furniture) adapted to store the apparatus, for example a hand luggage, during the travel. The apparatus (housing with or without container support, with or without dialyzer support, . . . ) may be sized in order to be smaller than the bag (hand luggage), at least one dimension smaller than 31 cm, another dimension smaller than 51 cm and/or another dimension smaller than 61 cm.

Figure 19:
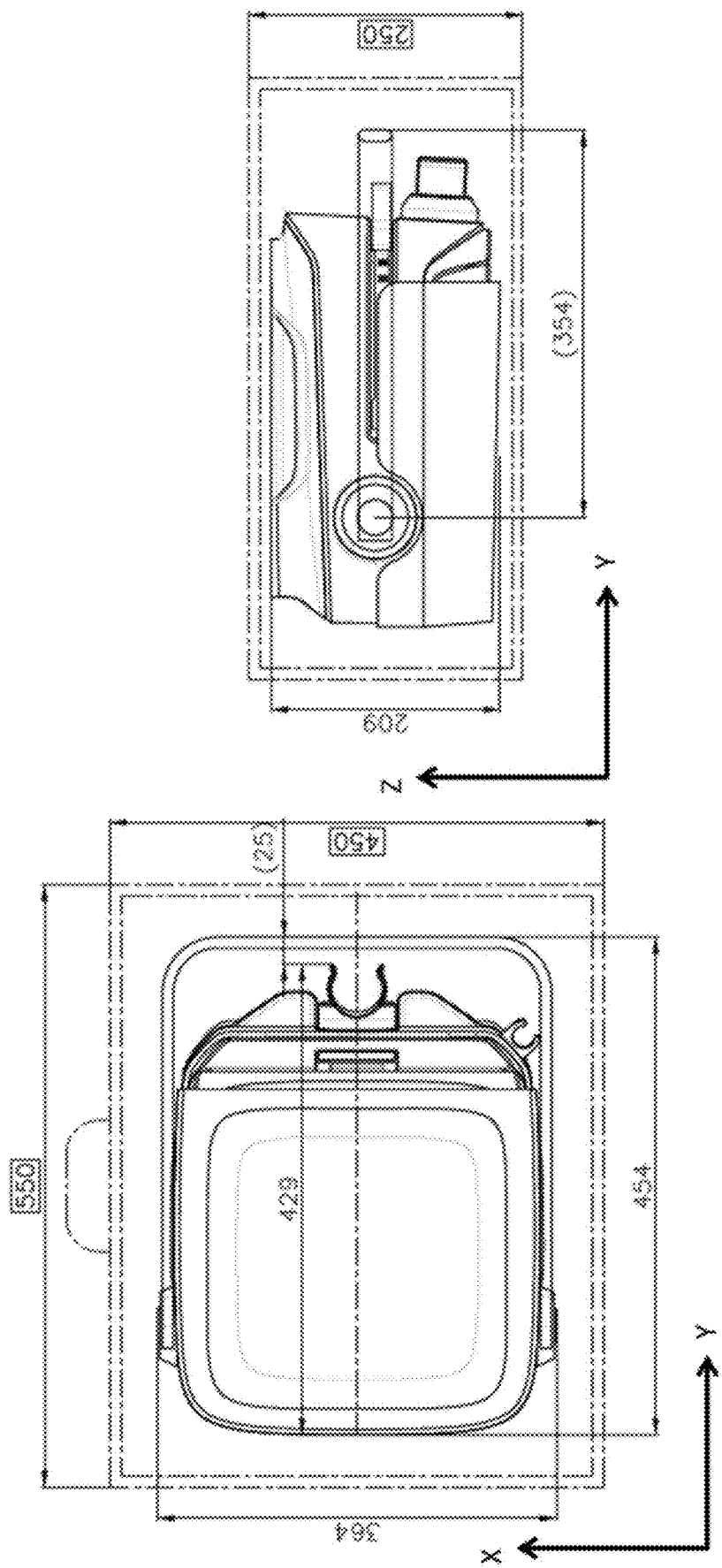
FIG. 19 shows a dialysis system stored in a hand luggage.

The FIG. 19 shows an apparatus stored in hand luggage. The hand luggage is drawn in dotted line and comprises a handle. The size shown in this figure is done as an example. The bag may comprise at least two distinct housing cavities, a first housing cavity intended to receive the apparatus and a second housing cavity intended to receive the display device 302 (for example a tablet).

The hand luggage may comprise a door having an open position and a closed position. The open position of the door allows placing the apparatus into the hand luggage (for example into a dedicated housing cavity) and the closed position allows moving the hand luggage in a secure manner. The hand luggage may further comprise rigid part (for example the side wall or the upper wall or the lower wall of the hand luggage) designed to protect the apparatus.

The hand luggage may be used as an apparatus support which may comprise a platform configured to support the apparatus in operating configuration.

The hand luggage may comprise retractable handle and/or retractable rollers (or wheels).

The FIG. 36 illustrates an other embodiment of the apparatus support.

The invention claimed is:
1. A dialysis system comprising:
a dialyzer having a blood compartment;
a blood circuit in fluid communication with the blood compartment of the dialyzer, including,
 an arterial line,
 an venous line,
 a valve configured to occlude at least a part of the blood circuit, and
 a blood pump configured to move a fluid through the blood circuit and to be actuated in at least one of a normal pump direction through the blood circuit and a reverse pump direction through the blood circuit, oppositely to the normal pump direction;
a cassette including a portion of the blood circuit;
a subsystem configured to control a dialysis treatment having a processor, a sensor, and a blood pumping mechanism configured to cooperate with the blood pump of the blood circuit;
a housing in which the subsystem is arranged, the housing having an opening configured to insert the cassette;
a movable support arranged in the housing and configured to hold the sensor and/or the blood pumping mechanism of the subsystem;
a cassette holder configured to removably receive the cassette; and
a loading system configured to move the movable support by an axial movement to a first position and to a second position relatively to the housing while the cassette holder is fixedly arranged in the housing, the loading system having an electric motor controlled by the processor, a drive assembly coupled to the electric motor, and a guiding assembly configured to cooperate with the drive assembly.

2. The system according to claim 1, further comprising:
- a fluid subsystem having a first storing compartment configured to store at least one of a priming solution, a solution compatible with blood, a rinsing solution, and/or
- a second storing compartment in fluid communication with the blood circuit,
- wherein the arterial line includes an arterial connector and the venous line includes an venous connector.

3. The system according to claim 2, wherein the fluid subsystem includes a first line in fluid communication with the first storing compartment and connected to the arterial line, a second line in fluid communication with the first storing compartment and connected to the venous line, and a third line configured to be removably connected to at least one of the arterial connector and/or the venous connector and to be in fluid communication with the first storing compartment.

4. The system according to claim 2, wherein the fluid subsystem includes a first line in fluid communication with the first storing compartment and connected to the arterial line, a second line in fluid communication with the first storing compartment and connected to the venous line, and a third line configured to be removably connected to at least one of the arterial connector and/or the venous connector and to be in fluid communication with the second storing compartment.

5. The system according to claim 2, wherein the first storing compartment and/or the second storing compartment of the fluid system is initially empty.

6. The system according to claim 2, wherein the processor is operatively connected to at least one of the valve, and/or the blood pump,
and is configured to carry out at least one operating sequence.

7. The system according to claim 1 wherein the first position is required for an operating configuration and the second position permits an insertion and/or a removal of the cassette.

8. The system according to claim 1, further comprising:
an indicator device configured to inform a user about a current position of the movable support.

9. The system according to claim 1, wherein the blood pumping mechanism includes a shaft and the cassette includes a roller assembly configured to be operatively coupled with the shaft and to at least partially align the cassette relative to the movable support, such that the sensor is aligned with a dedicated area of the cassette, when the movable support is in the first position.

10. The system according to claim 1, wherein the opening of the housing includes a sliding door.

11. The system according to claim 10, wherein the sliding door is mechanically coupled to at least one of the movable support and/or the loading system to open the sliding door when the movable support is moved to the second position.

12. The system according to claim 1, wherein the cassette holder includes a detection sensor configured to send a signal to the processor when the cassette is inserted into the cassette holder.

13. The system according to claim 12, wherein the processor is configured to initiate a displacement of the movable support depending on the signal of the detection sensor.

14. The system according to claim 1, further comprising:
a coding element configured to prevent an insertion of other types of cassettes.

15. The system according to claim 1 further comprising:
a locking system configured to cooperate with the cassette to prevent a withdrawal of the cassette when the movable support is in the first position.

16. The system according to claim 1, further comprising:
a sensor configured to monitor or to detect at least one of the first position and/or the second position of the loading system.

17. The system according to the claim 1, wherein the guiding assembly is configured to transform a motion of the electric motor into an axial motion of the movable support.

18. The system according to the claim 1, wherein the guiding assembly includes a guiding element and a sliding element.

* * * * *